US012565671B2

(12) United States Patent
Church et al.

(10) Patent No.: US 12,565,671 B2
(45) Date of Patent: **\*Mar. 3, 2026**

(54) METHODS OF COMBINING THE DETECTION OF BIOMOLECULES INTO A SINGLE ASSAY USING FLUORESCENT IN SITU SEQUENCING

(71) Applicant: President and Fellows of Harvard College, Cambridge, MA (US)

(72) Inventors: George M. Church, Brookline, MA (US); Evan R. Daugharthy, Cambridge, MA (US); Richard C. Terry, Carlisle, MA (US)

(73) Assignee: President and Fellows of Harvard College, Cambridge, MA (US)

( \* ) Notice: Subject to any disclaimer, the term of this patent is extended or adjusted under 35 U.S.C. 154(b) by 744 days.

This patent is subject to a terminal disclaimer.

(21) Appl. No.: 17/884,808

(22) Filed: Aug. 10, 2022

(65) Prior Publication Data

US 2023/0146821 A1 May 11, 2023

Related U.S. Application Data

(63) Continuation of application No. 16/288,200, filed on Feb. 28, 2019, now Pat. No. 11,447,807, which is a continuation of application No. PCT/US2017/049641, filed on Aug. 31, 2017.

(60) Provisional application No. 62/381,997, filed on Aug. 31, 2016.

(51) Int. Cl.
| | |
|---|---|
| *C12P 19/34* | (2006.01) |
| *A61L 27/50* | (2006.01) |
| *C12N 15/10* | (2006.01) |
| *C12Q 1/682* | (2018.01) |
| *C12Q 1/6834* | (2018.01) |
| *C12Q 1/6874* | (2018.01) |
| *G01N 33/68* | (2006.01) |

(52) U.S. Cl.
CPC .............. *C12P 19/34* (2013.01); *A61L 27/50* (2013.01); *C12N 15/1093* (2013.01); *C12Q 1/682* (2013.01); *C12Q 1/6834* (2013.01); *C12Q 1/6874* (2013.01); *G01N 33/6842* (2013.01); *A61L 2400/16* (2013.01); *B01L 2300/0636* (2013.01)

(58) Field of Classification Search
None
See application file for complete search history.

(56) References Cited

U.S. PATENT DOCUMENTS

| | | | |
|---|---|---|---|
| 4,123,610 A | 10/1978 | Summerton et al. |
| 4,844,617 A | 7/1989 | Kelderman et al. |
| 4,886,741 A | 12/1989 | Schwartz |
| 4,981,985 A | 1/1991 | Kaplan et al. |
| 5,151,189 A | 9/1992 | Hu et al. |
| 5,424,413 A | 6/1995 | Hogan et al. |
| 5,563,056 A | 10/1996 | Swan et al. |
| 5,594,235 A | 1/1997 | Lee |
| 5,635,352 A | 6/1997 | Urdea et al. |
| 5,695,940 A | 12/1997 | Drmanac et al. |
| 5,830,708 A | 11/1998 | Naughton |
| 5,834,758 A | 11/1998 | Trulson et al. |
| 5,871,921 A | 2/1999 | Andegren et al. |
| 6,068,979 A | 5/2000 | Akhavan-Tafti |
| 6,083,726 A | 7/2000 | Mills, Jr. et al. |
| 6,194,148 B1 | 2/2001 | Hori et al. |
| 6,232,067 B1 | 5/2001 | Hunkapiller et al. |
| 6,306,597 B1 | 10/2001 | Macevicz |
| 6,534,266 B1 | 3/2003 | Singer |
| 6,586,176 B1 | 7/2003 | Trnovsky et al. |
| 6,632,655 B1 | 10/2003 | Mehta et al. |
| 7,255,994 B2 | 8/2007 | Lao |
| 7,323,305 B2 | 1/2008 | Leamon et al. |
| 7,427,479 B2 | 9/2008 | Karger et al. |
| 7,473,767 B2 | 1/2009 | Dimitrov |
| 7,534,991 B2 | 5/2009 | Miller et al. |
| 7,555,155 B2 | 6/2009 | Levenson et al. |
| 7,655,898 B2 | 2/2010 | Miller |
| 7,745,129 B1 | 6/2010 | Schatz |
| 7,771,949 B2 | 8/2010 | Kramer |
| 7,906,285 B2 | 3/2011 | Drmanac |
| 7,910,304 B2 | 3/2011 | Drmanac |
| 7,941,279 B2 | 5/2011 | Hwang et al. |

(Continued)

FOREIGN PATENT DOCUMENTS

| | | |
|---|---|---|
| BR | 112015013784 A2 | 7/2017 |
| BR | 112015013785 A2 | 7/2017 |

(Continued)

OTHER PUBLICATIONS

Thomas, et al. (1998) "A Computer-controlled Nanosecond Laser System", Computers in Chemistry, 22(6): 491-98. (Year: 1998).\*
Sachidanandam, et al. (2001) "A map of the human genome sequence variation containing 1.42 million single nucleotide polymorphisms", Nature, 409(6822): 928-33. (Year: 2001).\*
Eid, et al. (2009) "Real-time DNA sequencing from single polymerase molecules", Science, 323(5910): 133-38. (Year: 2009).\*
Weibrecht, Irene et al., "Simultaneous Visualization of Both Signaling Cascade Activity and End-Point Gene Expression in Single Cells", PLOS ONE, vol. 6, No. 5, May 25, 2011 (May 25, 2011).
Larsson, Chatarina; Grundberg, Ida; Sbderberg, Ola; Nilsson, Mats: 11 In situ detection and genotyping of individual mRNA molecules, Nature Methods, vol. 7, No. 5 Apr. 11, 2010 (Apr. 11, 2010), pp. 395-397, XP055035168, DOI: 10.1038/nmeth.1448 Retrieved from the Internet: URL:http://www.nature.com/nmeth/journal/v7/n5/pdf/nmeth.1448.pdf [retrieved on Aug. 9, 2012].

(Continued)

*Primary Examiner* — Robert M Kelly
(74) *Attorney, Agent, or Firm* — Banner & Witcoff, Ltd.

(57) ABSTRACT

The present disclosure provides methods that combine RNA fluorescent in situ sequencing (FISSEQ) with other molecular detection modalities, forming an integrated panomic detection platform. In various embodiments, the present disclosure provides systems and methods to prepare a biological sample to preserve the spatial relationships of biomolecules of interest within the biological sample for FISSEQ detection.

20 Claims, 4 Drawing Sheets
(3 of 4 Drawing Sheet(s) Filed in Color)

(56)                 References Cited

U.S. PATENT DOCUMENTS

| | | |
|---|---|---|
| 7,989,166 B2 | 8/2011 | Koch et al. |
| 8,013,134 B2 | 9/2011 | Fredriksson |
| 8,124,751 B2 | 2/2012 | Pierce et al. |
| 8,199,999 B2 | 6/2012 | Hoyt et al. |
| 8,268,554 B2 | 9/2012 | Schallmeiner |
| 8,329,404 B2 | 12/2012 | McKernan et al. |
| 8,330,087 B2 | 12/2012 | Domenicali |
| 8,415,102 B2 | 4/2013 | Geiss et al. |
| 8,431,691 B2 | 4/2013 | McKernan et al. |
| 8,460,865 B2 | 6/2013 | Chee et al. |
| 8,462,981 B2 | 6/2013 | Determan et al. |
| 8,501,459 B2 | 8/2013 | Chen et al. |
| 8,519,115 B2 | 8/2013 | Webster et al. |
| 8,551,710 B2 | 10/2013 | Bernitz et al. |
| 8,658,361 B2 | 2/2014 | Wu et al. |
| 8,697,359 B1 | 4/2014 | Zhang |
| 8,871,445 B2 | 10/2014 | Cong et al. |
| 8,906,616 B2 | 12/2014 | Zhang et al. |
| 8,932,814 B2 | 1/2015 | Cong et al. |
| 8,946,389 B2 | 2/2015 | Gao et al. |
| 8,986,926 B2 | 3/2015 | Ferree et al. |
| 8,993,233 B2 | 3/2015 | Zhang et al. |
| 8,999,641 B2 | 4/2015 | Zhang et al. |
| 9,017,992 B2 | 4/2015 | Winther et al. |
| 9,201,063 B2 | 12/2015 | Sood et al. |
| 9,217,151 B2 | 12/2015 | Yin et al. |
| 9,257,135 B2 | 2/2016 | Ong et al. |
| 9,267,135 B2 | 2/2016 | Church et al. |
| 9,273,349 B2 | 3/2016 | Nguyen et al. |
| 9,371,563 B2 | 6/2016 | Geiss et al. |
| 9,371,598 B2 | 6/2016 | Chee |
| 9,376,717 B2 | 6/2016 | Gao et al. |
| 9,541,504 B2 | 1/2017 | Hoyt |
| 9,551,032 B2 | 1/2017 | Landegren et al. |
| 9,714,446 B2 | 7/2017 | Webster et al. |
| 9,714,937 B2 | 7/2017 | Dunaway |
| 9,727,810 B2 | 8/2017 | Fodor et al. |
| 9,778,155 B2 | 10/2017 | Gradinaru et al. |
| 9,783,841 B2 | 10/2017 | Nolan et al. |
| 9,896,720 B2 | 2/2018 | Raj et al. |
| 9,909,167 B2 | 3/2018 | Samusik et al. |
| 10,030,261 B2 | 7/2018 | Frisen et al. |
| 10,032,064 B2 | 7/2018 | Hoy |
| 10,126,242 B2 | 11/2018 | Miller et al. |
| 10,138,509 B2 | 11/2018 | Church et al. |
| 10,227,639 B2 | 3/2019 | Levner et al. |
| 10,246,700 B2 | 4/2019 | Dunaway et al. |
| 10,266,888 B2 | 4/2019 | Daugharthy et al. |
| 10,267,808 B2 | 4/2019 | Cai |
| 10,309,879 B2 | 6/2019 | Chen et al. |
| 10,317,321 B2 | 6/2019 | Tillberg et al. |
| 10,364,457 B2 | 7/2019 | Wassie et al. |
| 10,370,698 B2 | 8/2019 | Nolan et al. |
| 10,415,080 B2 | 9/2019 | Dunaway et al. |
| 10,457,980 B2 | 10/2019 | Cai et al. |
| 10,465,235 B2 | 11/2019 | Gullberg et al. |
| 10,494,662 B2 | 12/2019 | Church et al. |
| 10,494,667 B2 | 12/2019 | Chee |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,526,649 B2 | 1/2020 | Chen et al. |
| 10,545,075 B2 | 1/2020 | Deisseroth et al. |
| 10,580,128 B2 | 3/2020 | Miller |
| 10,640,816 B2 | 5/2020 | Beechem et al. |
| 10,669,569 B2 | 6/2020 | Gullberg et al. |
| 10,746,981 B2 | 8/2020 | Tomer et al. |
| 10,774,372 B2 | 9/2020 | Chee et al. |
| 10,774,374 B2 | 9/2020 | Frisen et al. |
| 10,794,802 B2 | 10/2020 | Gradinaru et al. |
| 10,802,262 B2 | 10/2020 | Tomer et al. |
| 10,815,519 B2 | 10/2020 | Husain et al. |
| 10,844,426 B2 | 11/2020 | Daugharthy et al. |
| 10,872,679 B2 | 12/2020 | Cai et al. |
| 10,964,001 B2 | 3/2021 | Miller |
| 11,021,737 B2 | 6/2021 | Church et al. |
| 11,078,520 B2 | 8/2021 | Church et al. |
| 11,111,521 B2 | 9/2021 | Church et al. |
| 11,118,220 B2 | 9/2021 | Daugharthy et al. |
| 11,293,051 B2 | 4/2022 | Church et al. |
| 11,293,052 B2 | 4/2022 | Church et al. |
| 11,293,054 B2 | 4/2022 | Levner et al. |
| 11,566,277 B2 | 1/2023 | Church et al. |
| 11,639,518 B2 | 5/2023 | Church et al. |
| 2002/0015952 A1 | 2/2002 | Anderson et al. |
| 2002/0029979 A1 | 3/2002 | Freund et al. |
| 2002/0155989 A1 | 10/2002 | Efimov et al. |
| 2002/0172950 A1 | 11/2002 | Kenny et al. |
| 2003/0148335 A1 | 8/2003 | Shen et al. |
| 2003/0165852 A1 | 9/2003 | Schueler et al. |
| 2004/0077014 A1 | 4/2004 | Becker |
| 2004/0081979 A1 | 4/2004 | Knezevic et al. |
| 2004/0248144 A1 | 12/2004 | Mir |
| 2004/0259190 A1 | 12/2004 | Naughton |
| 2005/0064435 A1 | 3/2005 | Su et al. |
| 2005/0106629 A1 | 5/2005 | McGrath et al. |
| 2005/0147981 A1 | 7/2005 | Yamakawa et al. |
| 2005/0191687 A1 | 9/2005 | Wang et al. |
| 2005/0233318 A1 | 10/2005 | Chee et al. |
| 2006/0024711 A1 | 2/2006 | Lapidus et al. |
| 2006/0077536 A1 | 4/2006 | Bromage et al. |
| 2006/0177833 A1 | 8/2006 | Brenner |
| 2006/0183107 A1 | 8/2006 | Melkonyan et al. |
| 2006/0216339 A1 | 9/2006 | Ambron et al. |
| 2006/0228733 A1 | 10/2006 | Pierce et al. |
| 2006/0234261 A1 | 10/2006 | Pierce et al. |
| 2006/0248349 A1 | 11/2006 | Rathjen et al. |
| 2006/0292611 A1 | 12/2006 | Berka et al. |
| 2007/0020650 A1 | 1/2007 | Kahvejian |
| 2007/0087362 A1 | 4/2007 | Church et al. |
| 2007/0117109 A1 | 5/2007 | Rothemund |
| 2007/0117177 A1 | 5/2007 | Luo et al. |
| 2007/0190543 A1 | 8/2007 | Livak |
| 2007/0206275 A1 | 9/2007 | Hemmer et al. |
| 2007/0231823 A1 | 10/2007 | McKeman et al. |
| 2007/0292877 A1 | 12/2007 | Dimitrov |
| 2008/0050718 A1 | 2/2008 | Gesteland et al. |
| 2008/0176769 A1 | 7/2008 | Rank et al. |
| 2008/0180790 A1 | 7/2008 | Tafas et al. |
| 2008/0269068 A1 | 10/2008 | Church et al. |
| 2009/0005259 A1 | 1/2009 | Drmanac |
| 2009/0105082 A1 | 4/2009 | Chetverin et al. |
| 2009/0208965 A1 | 8/2009 | Tafas et al. |
| 2009/0220968 A1 | 9/2009 | Issadore et al. |
| 2009/0246879 A1 | 10/2009 | Drmanac et al. |
| 2009/0280559 A1 | 11/2009 | McCarthy |
| 2010/0009868 A1 | 1/2010 | Yan et al. |
| 2010/0047924 A1 | 2/2010 | Webster et al. |
| 2010/0049448 A1 | 2/2010 | Doyle et al. |
| 2010/0076057 A1 | 3/2010 | Sontheimer et al. |
| 2010/0087325 A1 | 4/2010 | Buermann |
| 2010/0151472 A1 | 6/2010 | Nolan et al. |
| 2010/0223276 A1 | 9/2010 | Al-Shameri et al. |
| 2010/0238442 A1 | 9/2010 | Heng et al. |
| 2010/0268478 A1 | 10/2010 | Andregg et al. |
| 2011/0020291 A1 | 1/2011 | Banerjee et al. |
| 2011/0033520 A1 | 2/2011 | Mather et al. |
| 2011/0086774 A1 | 4/2011 | Dunaway |
| 2011/0092376 A1 | 4/2011 | Colston, Jr. et al. |
| 2011/0104693 A1 | 5/2011 | Seligmann |
| 2011/0189776 A1 | 8/2011 | Terns et al. |
| 2011/0208040 A1 | 8/2011 | Carmi et al. |
| 2011/0216953 A1 | 9/2011 | Callahan et al. |
| 2011/0223585 A1 | 9/2011 | Gullberg et al. |
| 2011/0223638 A1 | 9/2011 | Wiedenheft et al. |
| 2011/0245111 A1 | 10/2011 | Chee |
| 2011/0257031 A1 | 10/2011 | Bodeau et al. |
| 2011/0294135 A1 | 12/2011 | Carlson |
| 2012/0040397 A1 | 2/2012 | Luo et al. |
| 2012/0122712 A1 | 5/2012 | Goldstein |
| 2012/0126142 A1 | 5/2012 | Matsui et al. |
| 2012/0252686 A1 | 10/2012 | Umbarger et al. |
| 2012/0270214 A1 | 10/2012 | Bernitz et al. |

(56)     References Cited

U.S. PATENT DOCUMENTS

| | | |
|---|---|---|
| 2012/0330636 A1 | 12/2012 | Albou |
| 2013/0017229 A1 | 1/2013 | Mooney et al. |
| 2013/0130248 A1 | 5/2013 | Haurwitz et al. |
| 2013/0245096 A1 | 9/2013 | Abitbol |
| 2013/0253040 A1 | 9/2013 | Miller et al. |
| 2013/0288249 A1 | 10/2013 | Gullberg et al. |
| 2013/0323729 A1 | 12/2013 | Landegren et al. |
| 2014/0049632 A1 | 2/2014 | Hemmer |
| 2014/0068797 A1 | 3/2014 | Doudna et al. |
| 2014/0087378 A1 | 3/2014 | Chatre et al. |
| 2014/0087427 A1 | 3/2014 | Bujnicki et al. |
| 2014/0179006 A1 | 6/2014 | Zhang |
| 2014/0179770 A1 | 6/2014 | Zhang et al. |
| 2014/0200146 A1 | 7/2014 | Xie et al. |
| 2014/0220578 A1 | 8/2014 | Bohannon et al. |
| 2014/0220587 A1 | 8/2014 | Green, Jr. et al. |
| 2014/0270435 A1 | 9/2014 | Dunn |
| 2014/0273226 A1 | 9/2014 | Wu |
| 2014/0273233 A1 | 9/2014 | Chen et al. |
| 2014/0310830 A1 | 10/2014 | Zhang et al. |
| 2014/0315985 A1 | 10/2014 | May et al. |
| 2014/0342457 A1 | 11/2014 | Mali et al. |
| 2015/0004598 A1 | 1/2015 | Gao et al. |
| 2015/0005188 A1 | 1/2015 | Levner et al. |
| 2015/0098126 A1 | 4/2015 | Keller et al. |
| 2015/0133319 A1 | 5/2015 | Fu et al. |
| 2015/0247150 A1 | 9/2015 | Zhang et al. |
| 2015/0267251 A1 | 9/2015 | Cai et al. |
| 2016/0002704 A1 | 1/2016 | Diehl et al. |
| 2016/0024524 A1 | 1/2016 | Joung et al. |
| 2016/0024555 A1 | 1/2016 | Church et al. |
| 2016/0108458 A1 | 4/2016 | Frei et al. |
| 2016/0153006 A1 | 6/2016 | Zhang et al. |
| 2016/0160210 A1 | 6/2016 | Mali et al. |
| 2016/0253584 A1 | 9/2016 | Fodor et al. |
| 2016/0265046 A1 | 9/2016 | Zhang et al. |
| 2016/0289740 A1 | 10/2016 | Fu et al. |
| 2016/0305856 A1 | 10/2016 | Boyden et al. |
| 2016/0340662 A1 | 11/2016 | Zhang et al. |
| 2016/0355795 A1 | 12/2016 | Ran et al. |
| 2016/0358326 A1 | 12/2016 | Sarachan et al. |
| 2016/0376642 A1 | 12/2016 | Landegren et al. |
| 2017/0009278 A1 | 1/2017 | Soderberg et al. |
| 2017/0010672 A1 | 1/2017 | Tanaka et al. |
| 2017/0067096 A1 | 3/2017 | Wassie et al. |
| 2017/0081489 A1 | 3/2017 | Rodriques et al. |
| 2017/0176338 A1 | 6/2017 | Wu et al. |
| 2017/0191078 A1 | 7/2017 | Zhang et al. |
| 2017/0212983 A1 | 7/2017 | Cai et al. |
| 2017/0220733 A1 | 8/2017 | Zhuang et al. |
| 2017/0253918 A1 | 9/2017 | Kohman |
| 2017/0262984 A1 | 9/2017 | Barnes et al. |
| 2018/0010166 A1 | 1/2018 | Pierce et al. |
| 2018/0051322 A1 | 2/2018 | Church et al. |
| 2018/0052081 A1 | 2/2018 | Kohman |
| 2018/0080876 A1 | 3/2018 | Rockel et al. |
| 2018/0208967 A1 | 7/2018 | Larman et al. |
| 2018/0237864 A1 | 8/2018 | Imler et al. |
| 2018/0282787 A1 | 10/2018 | Walter et al. |
| 2019/0017106 A1 | 1/2019 | Frisen et al. |
| 2019/0032128 A1 | 1/2019 | Chen et al. |
| 2019/0119735 A1 | 4/2019 | Deisseroth et al. |
| 2019/0203275 A1 | 7/2019 | Frisen et al. |
| 2019/0264270 A1 | 8/2019 | Zhuang et al. |
| 2019/0271028 A1 | 9/2019 | Khafizov et al. |
| 2019/0276881 A1 | 9/2019 | Zhuang et al. |
| 2020/0010891 A1 | 1/2020 | Beechem et al. |
| 2020/0034347 A1 | 1/2020 | Selly |
| 2020/0090786 A1 | 3/2020 | Quiroz Zarate et al. |
| 2020/0140920 A1 | 5/2020 | Pierce et al. |
| 2020/0239946 A1 | 7/2020 | Dewal |
| 2020/0354782 A1 | 11/2020 | Dewal |
| 2021/0017587 A1 | 1/2021 | Cai et al. |
| 2021/0115504 A1 | 4/2021 | Cai et al. |

FOREIGN PATENT DOCUMENTS

| | | | |
|---|---|---|---|
| BR | 112015008708 A2 | 9/2017 |
| BR | 112015012375 A2 | 9/2017 |
| BR | 112015014425 A2 | 10/2017 |
| BR | 112015022061 A2 | 11/2017 |
| CA | 2891347 A1 | 6/2014 |
| CN | 1580283 A | 2/2005 |
| CN | 1959384 A | 5/2007 |
| CN | 101553306 A | 10/2009 |
| CN | 105392898 A | 3/2016 |
| EP | 2878671 A1 | 6/2015 |
| JP | H04-268359 A | 9/1992 |
| JP | 2007-526772 A | 9/2007 |
| JP | 2009-538123 A | 11/2009 |
| JP | 2012-170337 A | 9/2012 |
| JP | 2014-506472 A | 3/2014 |
| JP | 2014-513523 A | 6/2014 |
| JP | 2015-090458 A | 5/2015 |
| KR | 20080003402 A | 1/2008 |
| WO | 9746704 A1 | 12/1997 |
| WO | 98/56955 A1 | 12/1998 |
| WO | 0126708 A1 | 4/2001 |
| WO | 01/37266 A1 | 5/2001 |
| WO | 2003044229 A1 | 5/2003 |
| WO | 2004/104645 A2 | 12/2004 |
| WO | 2006/138257 A2 | 12/2006 |
| WO | 2007/001986 A2 | 1/2007 |
| WO | 2007076128 A2 | 7/2007 |
| WO | 2007086900 A2 | 8/2007 |
| WO | 2007121489 A2 | 10/2007 |
| WO | 2007/123744 A2 | 11/2007 |
| WO | 2007/149696 A1 | 12/2007 |
| WO | 2008069973 A2 | 6/2008 |
| WO | 2008/108989 A2 | 9/2008 |
| WO | 2008157696 A2 | 12/2008 |
| WO | 2009/046348 A1 | 4/2009 |
| WO | 2009046149 A1 | 4/2009 |
| WO | 2010/054108 A2 | 5/2010 |
| WO | 2010080134 A1 | 7/2010 |
| WO | 2010/087325 A1 | 8/2010 |
| WO | 2010104533 A2 | 9/2010 |
| WO | 2011/143124 A2 | 11/2011 |
| WO | 2011143583 A1 | 11/2011 |
| WO | 2012005595 A2 | 1/2012 |
| WO | 2012058638 A2 | 5/2012 |
| WO | 2012/110899 A2 | 8/2012 |
| WO | 2012150035 A1 | 11/2012 |
| WO | 2012/164565 A1 | 12/2012 |
| WO | 2013055995 A2 | 4/2013 |
| WO | 2013096851 A1 | 6/2013 |
| WO | 2013/098244 A1 | 7/2013 |
| WO | 2013/126794 A1 | 8/2013 |
| WO | 2013119827 A1 | 8/2013 |
| WO | 2013/141680 A1 | 9/2013 |
| WO | 2013/142578 A1 | 9/2013 |
| WO | 2013176772 A1 | 11/2013 |
| WO | 2014/022702 A2 | 2/2014 |
| WO | 2014/048083 A1 | 4/2014 |
| WO | 2014/065596 A1 | 5/2014 |
| WO | 2014/089290 A1 | 6/2014 |
| WO | 2014/093595 A1 | 6/2014 |
| WO | 2014/093622 A2 | 6/2014 |
| WO | 2014/093661 A2 | 6/2014 |
| WO | 2014/093694 A1 | 6/2014 |
| WO | 2014099744 A1 | 6/2014 |
| WO | 2014/113493 A1 | 7/2014 |
| WO | 2014/144288 A1 | 9/2014 |
| WO | 2014/150624 A1 | 9/2014 |
| WO | 20140163886 A1 | 10/2014 |
| WO | 2014182528 A2 | 11/2014 |
| WO | 2014/191518 A1 | 12/2014 |
| WO | 2014/197568 A2 | 12/2014 |
| WO | 2015/127183 A2 | 8/2015 |
| WO | 2015118029 A1 | 8/2015 |
| WO | 2016007839 A1 | 1/2016 |
| WO | 2016081740 A1 | 5/2016 |
| WO | 2017/027367 A1 | 2/2017 |
| WO | 2017079382 A1 | 5/2017 |

(56)                    References Cited

FOREIGN PATENT DOCUMENTS

| WO | 2017079406 A1 | 5/2017 |
| WO | 2017143155 A2 | 8/2017 |
| WO | 2017/161251 A1 | 9/2017 |
| WO | 2017189525 A1 | 11/2017 |

OTHER PUBLICATIONS

Nuovo: "Co-labeling Using In Situ PCR: A Review " Journal of Histochemistry & Cytochemistry, vol. 49, No. 11, Nov. 1, 2001 (Nov. 1, 2001), pp. 1329-1339, XP055164942, ISSN: 0022-1554, DOI: 10.1177/002215540104901101.

Mitra R. D. et al: 11 In situ localized amplification and contact replication of many individual DNA molecules 11 Nucleic Acids Research, Information Retrieval Ltd, GB, vol. 27, No. 24, Dec. 15, 1999 (Dec. 15, 1999), page e34, XP002292358, ISSN: 0305-1048, DOI: 10.1093/NAR/27.24.E34.

Ke et al: 11 In situ sequencing for RNA analysis in preserved tissue and cells 11 Nature Methods, vol. 10, No. 9, Jul. 14, 2013 (Jul. 14, 2013), pp. 857-860, XP055163946, ISSN: 1548-7091, DOI: 10.1038/nmeth.2563.

Lee et al: "Highly Multiplexed Subcellular RNA Sequencing in Situ", Science, vol. 343, No. 6177, Feb. 27, 2014 (Feb. 27, 2014), pp. 1360-1363, XP055305772, us ISSN: 0036-8075, DOI: 10.1126/science.1250212.

Clausson et al: "Compaction of rolling circle amplification products increases signal integrity and signal-to-noise ratio", Scientific Reports, vol. 5, Jul. 23, 2015 (Jul. 23, 2015), p. 12317, XP055305777, DOI: 10.1038/srep12317.

Nadji et al., "Photochemically and Photoenzymatically Cleavable DNA," J. Am. Chem. Soc. 1992, 114, 9266-9269.

Extended European Search Report and Written Opinion issued Dec. 17, 2019 for EP 19180827.8.

Supplementary European Search Report and Written Opinion issued Mar. 18, 2020.

Chen et al., "Expansion microscopy," Science, vol. 347, No. 6221, pp. 543-548 (Jan. 30, 2015).

Chozinski et al., "Expansion microscopy with conventional antibodies and fluorescent proteins," Nature Methods, vol. 13, No. 6, pp. 485-488 (Jun. 1, 2016).

Chen et al., "Nanoscale imaging of RNA with expansion microscopy," Nature Methods, vol. 13, No. 8, pp. 679-684 (Aug. 1, 2016).

Supplementary European Search Report issued Apr. 9, 2020 for EP 17847555.

Amasino, "Acceleration of nucleic acid hybridization rate by polyethylene glycol," Analytical Biochemistry, vol. 152, No. 2, pp. 304-307 (Feb. 1, 1986).

Bouché et al., "The effect of spermidine on endonuclease inhibition by agarose contaminants," Analytical Biochemistry, vol. 115, No. 1, pp. 42-45 (Jul. 15, 1981).

Kuznetsova et al., "What Macromolecular Crowding Can Do to a Protein," Int. J. Mol. Sci., vol. 15, No. 12, pp. 23090-23140 (Dec. 1, 2014).

Oupicky et al., "Laterally stabilized complexes of DNA with linear reducible polycations: Strategy for triggered intracellular actication of DNA delivery vectors," Journal of the American Chemical Society, vol. 124, No. 1, pp. 8-9 (Jan. 9, 2002).

Nguyen, Son C., "Strategies for Studying Chromatin Regulation and Organization," Doctoral Dissertation, Harvard University (May 1, 2018); retrieved from https://dash.harvard.edu/bitstream/handle/1/33493431/NGUYEN-DISSERTATION-2016.pdf?sequence=4&isAllowed=y on Apr. 8, 2020.

Zhou et al. "In Situ Detection of Messenger RNA Using Digoxigenin-Labeled Oligonucleotides and Rolling Circle Amplification" Experimental and Molecular Pathology 70, 281-288 (2001).

May 29, 2020—Examination Report issued for EP 18173059.9.

Jun. 1, 2020—Examination Report issued for GB 1809029.0.

Wright et al., "Dynamic closed-loop system for focus tracking using a spatial light modulator and a deformable membrane mirror," Optics Express, vol. 14, No. 1, pp. 222-228 (Jan. 9, 2006).

Wang et al., "The method of axial drift compensation of laser differential confocal microscopy based on zero-tracking," Proc. of SPIE, vol. 9618, 96180X (2015).

Ohata et al., "Confocal Imaging Analysis of Intracellular Ions in Mixed Cellular Systems or in Situ Using Two Types of Confocal Microscopic Systems," Methods in Enzymology, vol. 307, pp. 425-441 (1999), particularly p. 437.

Supplemental Material for Schweitzer et al. (PNAS 2000; 97(18):10113-10119) (Year: 2000).

Aug. 3, 2020—(US) Non-Final Office Action—U.S. Appl. No. 16/157,243.

Aug. 3, 2020 (US) Non-Final Office Action—U.S. Appl. No. 16/393,215.

Jul. 2, 2020—(US) Non-Final Office Action—U.S. Appl. No. 16/255,920.

Aug. 10, 2020—(GB) Examination Report—GB App. No. 1809029.0.

Sep. 24, 2020—(US) Final Office Action—U.S. Appl. No. 15/772,652.

Markaki et al. "Fluorescence In Situ Hybridization Applications for Super-Resolution 3D Structured Illumination Microscopy" Methods in Microbiology, Jan. 2013.

Achim et al. "High-throughput spatial mapping of single-cell RNA-seq data to tissue of origin" Nature Biotechnology, Apr. 13, 2015.

Sep. 25, 2020—(US) Non-Final Office Action—U.S. Appl. No. 16/386,337.

Aug. 25, 2020—(JP) Notice of Reasons for Rejection—App. No. 2018-522985.

PI: Piezo Nano Positioning, 2008 (online), retrieved on Aug. 12, 2020, pp. 1-6 <https://www.pi-usa.us/fileadmin/user_upload/pi_us/files/product_datasheets/N725_Piezo_Focus_Positioner.pdf>.

Sep. 14, 2020—(CA) Examination Report—App. No. 2,850,509.

Mali, P. et al. RNA-Guided Human Genome Engineering Via Cas9. Science. Jan. 3, 2013, vol. 339; pp. 823-826; abstract; p. 823, second column, second to third paragraph; p. 823, third column, second paragraph to third paragraph; figure 1; Supplementary material, p. 4, first paragraph; p. 7, first paragraph; Supplementary figures S1, S3. DOI: 10.1126/science.1232033.

Tiley, LS et al. The VP16 Transcription Activation Domain Is Functional When Targeted to a Promoter-Proximal RNA Sequence. Genes and Development. 1992. vol. 6; pp. 2077-2087; abstract; p. 2077, first column, first paragraph.

Trafton, A. Editing The Genome With High Precision [online]. MIT News office. Jan. 3, 2013 [retrieved on Dec. 4, 2014. Retrieved from the Internet: <URL:http:/1newsoffice. Trafton .edut20 13/editing-the-genome-with-high-precision-01 03 >;pp. 1-3; p. 3, third paragraph.

Leman, Ar et al. The Replication Forie Understanding The Eukaryotic Replication Machinery and the Challenges to Genome Duplication. Genes. Jan. 29, 2013. vol. 4; pp. 1-32; figure 1; DOI: 10.3390/genes4010001.

Qi, L et al. Repurposing CRISPR as an RNA-Guided Platform For Sequence-Specific Control of Gene Expression. Cell. Feb. 28, 2013. vol. 152; pp. 1173-1183; figures 2, 4. DOI: 10.1 016/j.cell.2013.02.022.

Gasiunas, G et aL Cas9-crRNA Ribonucleoprotein Complex Mediates Specific DNA Cleavage for Adaptive Immunity in Bacteria. PNAS. Sep. 4, 2012. vol. 109, No. 39; pp. E2579-E2586; p. E2583, first column, first paragraph. DOI: 10.1073/pnas.1208507109.

Cong, Let al. Multiplex Genome Engineering Using CRISPR/Cas Systems. Science. Jan. 3, 2013, vol. 339; pp. 819-823; abstract; p. 821, third column; p. 822, first column, first paragraph; figure 4. DOI: 10.1126/science.1231143.

Jinek, M et al. A Programmable Dual-RNA-Guided DNA Endonuclease in Adaptive Bacterial Immunity. Science. Jun. 28, 2012. vol. 337; pp. 816-821; DOI: 10.1126/science.1225829.

CRISPR in The Lab: A Practical Guide [online]. Addgene. Sep. 4, 2014. Retrieved on Dec. 4, 2014. Retrieved from the Internet: <URL: https://www.addgene.org/CRISPR/guide/>.

(56) References Cited

OTHER PUBLICATIONS

Cheng, AW et al. Multiplexed Activation of Endogenous Genes By CRISP R-on, An RNA-Guided Transcriptional Activator System. Cell Research. Aug. 27, 2013. vol. 23; pp. 1163-1171. DOI: 10.1038/cr.2013.122.

Mali, P. et al. CAS9 Transcriptional Activators For Target Specificity Screening and Paired Nickases for Cooperative Genome Engineering. Nature Biotechnology. Aug. 1, 2013. vol. 31; pp. 833-838; entire document. DOI: 10.1038/nbt.2675.

Ran, FA et al. Double Nicking By RNA-Guided CRISPR Cas9 for Enhanced Genome Editing Specificity. Cell. Sep. 12, 2013. vol. 154; pp. 1380-1389. DOI: 10.1016/j.cell.2013.08.021.

International Search Report and Written Opinion issued in corresponding International Application No. PCT/US14/40868, mailed Dec. 31, 2014.

Stougaard et al. "In situ detection of non-polyadenylated RNA molecules using Turtle Probes and target primed rolling circle PRINS" BMC Biotechnology; 7:69; Oct. 18, 2007; pp. 1-10.

Nakano et al. "Effects of Molecular Crowding on the Structures, Interactions, and Functions of Nucleic Acids" Chemical Reviews; 2014; 114; pp. 2733-2758.

Zenklusen, Daniel and Singer, Robert H. "Analyzing mRNA Expression Using Single mRNA Resolution Fluorescent in Situ Hybridization" Methods in Enzymology, vol. 470, <https://www.ncbi.nlm. nih.gov/pmc/articles/PMC3162037/>, pp. 1-17, Mar. 1, 2010.

Zenklusen, Daniel and Singer, Robert H. "Analyzing mRNA Expression Using Single mRNA Resolution Fluorescent in Situ Hybridization" Methods in Enzymology, 2010, vol. 470, pp. 641-659.

Weibrecht, I. et al In situ detection of individual mRNA molecules and protein complexes or post-translational modifications using padlock probes combined with the in situ proximity ligation assay (2013) Nature Protocols 8(2): 355-372 (Year: 2013).

Drmanac et al. "Human Genome Sequencing Using Unchained Base Reads on Self-Assembling DNA Nanoarrays" Science; vol. 327; pp. 78-81; Jan. 1, 2010.

Islam et al. "Characterization of the single-cell transcriptional landscape by highly multiplex RNA-seq" Genome Research; vol. 21; May 4, 2011; pp. 1160-1167.

Larsson et al. "In situ detection and genotyping of individual mRNA molecules" Nature Methods; vol. 7; No. 5; May 2010; pp. 395-397.

Shendure et al. "Accurate Multiplex Polony Sequence of an Evolved Bacterial Genome" Science; vol. 309; Sep. 9, 2005; pp. 1728-1732.

Al-Attar et al., Clustered Regularly Interspaced Short Palindromic Repeats (CRISPRs ): The Hallmark of an Ingenious Antiviral Defense Mechanism in Prokaryotes, Bioi Chern. (20 11) vol. 392, Issue 4, pp. 277-289.

Carroll, "A CRISPR Approach to Gene Targeting" 20(9) Molecular Therapy 1658-1660 (Sep. 2012).

Jinek , et al. 'RNA-programmed genome editing in human cells.' eLite 2013;2:e00471 . [retrieved 1-3, 6, 7, 10-12 on Jun. 3, 2014). Retrieved from the Internet. <URL: http://elife .elifesciences.org/ content/2/e00471 >. entire document.

Hale et al., Essential Features and Rational Design of CRISPR RNAs That Function With the Cas RAMP Module Complex to Cleave RNAs, Molecular Cell, (20 12) vol. 45, Issue 3, 292-302.

Hatoum-Aslan, et al. 'Mature clustered, regularly interspaced, short palindromic repeats RNA 5,9, 14 (crRNA) length is measured by a ruler mechanism anchored at the precursor processing site.' Proceedings of the National Academy of Sciences. vol. 108, No. 52. pp. 21218-21222. Dec. 2011. entire document.

Makarova et al., "Evolution and classification of the CRISPR-Cas systems" 9(6) Nature Reviews Microbiology 467-477 (1-23) (Jun. 2011).

Rho, Mina et al. 'Diverse CRISPRs Evolving in Human Microbiomes.' PLoS Genetics. vol. 8, No. 6. 1-14 pp. 1-12. Jun. 2012. entire document.

Sontheimer Erik, Project 7: Establishing RNA-Directed DNA Targeting in Eukaryotic Cells; Project dates: Nov. 16, 2011 to Dec. 31, 2012 (Feb. 4, 2012).

Wiedenheft et al., "RNA-guided genetic silencing systems in bacteria and archaea" 482 Nature 331-338 (Feb. 16, 2012).

Liu et al., Cell-Penetrating Peptide-Mediated Delivery of TALEN Proteins via Bioconjugation for Genome Engineering, PLOS ONE, 2014, vol. 9(1), pp. 1-7.

Ramakrishna et al., Gene disruption by cell-penetrating peptide-mediated delivery of Cas9 protein and guide RNA, Genome Res. published online Apr. 2, 2014, pp. 1-20 plus figures.

The Delivery Problem, Nature Biotechnology, 2006, vol. 24(3), pp. 305-306.

Ansari et al., Riboactivators: Transcription activation by non-coding RNA, Grit Rev Biochem Mol Bioi. 2009 ; 44(1 ): 50-61.

Sapranauskas et alb (Nucleic Acids Research, 2011, 39:9275-9282).

U.S. Appl. No. 61/794,422, filed Mar. 15, 2013, Davis, G. et al.

U.S. Appl. No. 61/781,598, filed Mar. 14, 2013, Haurwitz, R.

Gilbert, Luke A., et al., "CRISPR-Mediated Modular RNA-Guided Regulation of Transcription in Eukaryotes," Cell, vol. 154, No. 2, Jul. 1, 2013 (Jul. 1, 2013), pp. 442-451.

Mali, P. et al., "Supplementary Materials for RNA-Guided Human Genome Engineering via Cas9," Science, vol. 339, No. 6121, Jan. 3, 2013 (Jan. 3, 2013), pp. 1-36.

Maeder, Morgan L., et al.,"Robust, synergistic regulation of human gene expression using TALE activators," HHS Public Access Author Manuscript, vol. 10, No. 3, Feb. 10, 2013 (Feb. 10, 2013), pp. 243-245.

Perez-Pinera, Pablo, et al., "Synergistic and tunable human gene activation by combinations of synthetic transcription factors," Nature Methods, vol. 10. No. 3, Feb. 3, 2013 (Feb. 3, 2013), pp. 239-242.

Preliminary Office Action issued by Brazilian Patent Office on Apr. 7, 2020.

Official Notification issued May 24, 2020 for IL 242959.

Jun. 2, 2020—(JP) Notice of Reasons for Rejection for App. No. 2019-039027.

Jul. 3, 2020—(AU) Examination Report for App. No. 20202039777.

Aug. 19, 2020—(MX) Office Action—App. No. MX/a/2015/ 016798.

Sep. 10, 2020—(CA) Office Action—App. No. 2,914,638.

Sep. 21, 2020—(NZ) First Examination Report—App. No. 715280.

Sep. 21, 2020—(NZ) First Examination Report—App. No. 753950.

Fu et al., "Improving CRISPR-Cas nuclease specificity using truncated guide RNAs," Nature Biotechnology, vol. 32, op. 249-284 (Jan. 26, 2014).

Lin et al., "CRISPR/Cas9 systems have off-target activity with insertions or deletions between target DNA and guide RNA sequences," Nucleic Acids Research, vol. 42, No. 11, pp. 7473-7485 (May 16, 2014).

Sep. 21, 2020—(NZ) First Examination Report—App. No. 753951.

Sep. 25, 2020—(RU) Office Action—App. No. 2019114706.

DiCarlo et al., "Genome engineering in Saccharomyces cerevisiae using CRISPR-Cas systems," Nucleic Acids Research, vol. 41, No. 7, pp. 4336-4343 (2013).

Gusev et al. "Rolling Circle Amplification: A New Approach to Increase Sensitivity for Immunohistochemistry and Flow Cyometry" American Journal of Pathology, vol. 159, No. 1, Jul. 2001, pp. 63-69.

Nov. 10, 2020—(US) Non-Final Office Action—U.S. Appl. No. 16/285,292.

Pihlak et al. "Rapid genome sequencing with short universal tiling probes" Nature Biotechnology, vol. 26, No. 6, Jun. 2008, pp. 676-684.

Lizardi "Next-generation sequencing-by-hybridization" Nature Biotechnology, vol. 26, No. 6, Jun. 2008, pp. 649-650.

Mignardi et al. "Fourth-generation sequencing in the cell and the clinic" Genome Medicine, 2014, 6:31.

Dec. 24, 2020 (US)—Notice of Allowance—U.S. Appl. No. 16/393,215.

Terry R, Porreca G, McCarthy K, Church GM. 2008. Polonator Instrument https://web.archive.org/web/20080807155459/http://www. polonator.org/index.htm; Wayback Machine (Aug. 7, 2008) "Open, Affordable, Sequencing . . . ".

Terry R, Porreca G, McCarthy K, Church GM. 2008. Polonator Instrument https://web.archive.org/ web/20080807155600/http:// www.polonator.org;/vision.aspx; Wayback Machine (Aug. 7, 2008) "The Vision".

(56) References Cited

OTHER PUBLICATIONS

Terry R, Porreca G, McCarthy K, Church GM. 2008. Polonator Instrument https://web.archive.org/web/20080807155250/http://www.polonator.org/ecosystem; Wayback Machine (Aug. 7, 2008) "The Polonator Ecosystem".

Terry R, Porreca G, McCarthy K, Church GM. 2008. Polonator Instrument https://web.archive.org/web/20080807155759/http://www.polonator.org/instrument; Wayback Machine (Aug. 7, 2008) "Instrument Overview".

Terry R, Porreca G, McCarthy K, Church GM. 2008. Polonator Instrument https://web.archive.org/web/20080807155857/http://www.polonator.org; Wayback Machine (Aug. 7, 2008) "Protocols".

Terry R, Porreca G, McCarthy K, Church GM. 2008. Polonator Instrument https://web.archive.org/web/2008090513362/http://www.polonator.org/protocols/pet.aspx; Wayback Machine (Sep. 5, 2008) "PET (Paired End-Tag) Genomic Shotgun Library Construction Protocol".

Terry R, Porreca G, McCarthy K, Church GM. 2008. Polonator Instrument https://web.archive.org/web/20080905133855/http://www.polonator.org/protocols/pcr.aspx; Wayback Machine (Sep. 5, 2008) "Emulsion PCR Protocol".

Terry R, Porreca G, McCarthy K, Church GM. 2008. Polonator Instrument https://web.archive.org/web/20080905133913/http://www.polonator.org; Wayback Machine (Sep. 5, 2008) "Emulsion Breaking Protocol".

Terry R, Porreca G, McCarthy K, Church GM. 2008. Polonator Instrument https://web.archive.org/web/20080905133837/http://www.polonator.org/protocols/beadenrichment.aspx; Wayback Machine (Sep. 5, 2008) "Bead Enrichment Protocol".

Terry R, Porreca G, McCarthy K, Church GM. 2008. Polonator Instrument https://web.archive.org/web/20080905133372/http://www.polonator.org/protocols.beadcapping.aspx; Wayback Machine (Sep. 5, 2008) "Bead Capping Protocol".

Terry R, Porreca G, McCarthy K, Church GM. 2008. Polonator Instrument https://web.archive.org/web/20080905133372/http://www.polonator.org/protocols/coverslip.aspx; Wayback Machine (Sep. 5, 2008) "Coverslip Aminosilanation and Arraying Protocol".

Terry R, Porreca G, McCarthy K, Church GM. 2008. Polonator Instrument https://web.archive.org/web/20080905133800/http://www.polonator.org; Wayback Machine (Sep. 5, 2008) "Polony Sequence by Ligation Protocol".

Terry R, Porreca G, McCarthy K, Church GM. 2008. Polonator Instrument https://web.archive.org/web/20080705172604/http://www.polonator.org; Wayback Machine (Jul. 5, 2008) "Polony Sequence Protocols".

Terry R, Porreca G, McCarthy K, Church GM. 2008. Polonator Instrument https://web.archive.org/web/20080905133818/http://www.polonator.org; Wayback Machine (Sep. 5, 2008) "Help Wanted".

Terry R, Porreca G, McCarthy K, Church GM. 2008. Polonator Instrument https://web.archive.org/web/20080807155529/http://www.polonator.org/software.aspx; Wayback Machine (Aug. 7, 2008) "Software".

Terry R, Porreca G, McCarthy K, Church GM. 2008. Polonator Instrument https://web.archive.org/web/20080807155404/http://www.polonator.org; Wayback Machine (Aug. 7, 2008) "Reagent Kits".

Terry R, Porreca G, McCarthy K, Church GM. 2008. Polonator Instrument https://web.archive.org/web/20080905133541/http://www.polonator.org/reagentkits/run.aspx; Wayback Machine (Sep. 5, 2008) "Run Kits".

Terry R, Porreca G, McCarthy K, Church GM. 2008. Polonator Instrument https://web.archive.org/web/20080905133601/http://www.polonator.org/reagentkits.pairedtag.aspx; Wayback Machine (Sep. 5, 2008) "Paired-Leg Library Kits".

Terry R, Porreca G, McCarthy K, Church GM. 2008. Polonator Instrument https://web.archive.org/web/20080905133741/http://www.polonator.org/reagentkits.emulsion.aspx; Wayback Machine (Sep. 5, 2008) "Emulsion PCR/Bead Capping Kits".

Terry R, Porreca G, McCarthy K, Church GM. 2008. Polonator Instrument https://web.archive.org/web/20080905133702/http://www.polonator.org/reagentkits/enrichment.aspx; Wayback Machine (Sep. 5, 2008) "Enrichment Kits".

Terry R, Porreca G, McCarthy K, Church GM. 2008. Polonator Instrument https://web.archive.org/web/20080807155316/http://www.polonator.org/flowcells.aspx; Wayback Machine (Aug. 7, 2008) "Flow Cells".

Church GM. 2006. "Genomes for all" Sci Am 294: 46-54.

De Bakker PI, Yelensky R, Pe'er I, Gabriel SB, Daly MJ, Altshuler D. 2005. "Efficiency and power in genetic association studies" Nat Genet 37: 1217-23.

Dixon AL, Liang L, Moffatt MF, Chen W, Heath S, Wong KC, Taylor J, Burnett E, Gut I, Farrall M, Lathrop GM, Abecasis GR, Cookson WO. 2007. "A genome-wide association study of global gene expression" Nat Genet 39: 1202-7.

Emilsson V, Thorleifsson G, Zhang B, Leonardson AS, Zink F, Zhu J, Carlson S, Helgason A, Walters GB, Gunnarsdottir S, Mouy M, Steinthorsdottir V, Eiriksdottir GH, Bjornsdottir G, Reynisdottir I, Gudbjartsson D, Helgadottir A, Jonasdottir A, Jonasdottir A, Styrkarsdottir U, Gretarsdottir S, Magnusson KP, Stefansson H, Fossdal R, Kristjansson K, Gislason HG, Stefansson T, Leifsson BG, Thorsteinsdottir U, Lamb JR, Gulcher JR, Reitman ML, Kong A, Schadt EE, Stefansson K. 2008; "Genetics of gene expression and its effect on disease" Nature 452: 423-8.

Risch N, Merikangas K. 1996. "The future of genetic studies of complex human diseases" Science 273: 1516-7.

Schadt EE, Monks SA, Drake TA, Lusis AJ, Che N, Colinayo V, Ruff TG, Milligan SB, Lamb JR, Cavet G, Linsley PS, Mao M, Stoughton RB, Friend SH. 2003. "Genetics of gene expression surveyed in maize, mouse and man" Nature 422: 297-302.

Altshuler D, Daly MJ, Lander ES. 2008. "Genetic mapping in human disease" Science 322: 881-8.

Cookson W, Liang L, Abecasis G, Moffatt M, Lathrop M. 2009. "Mapping complex disease traits with global gene expression" Nat Rev Genet 10: 184-94.

International HapMap C. 2005. "A haplotype map of the human genome" Nature 437: 1299-320. PMC Id: PMC1880871.

Klein RJ. 2007. "Power analysis for genome-wide association studies" BMC Genet 8: 58. PMC Id: PMC2042984.

Kwan T, Benovoy D, Dias C, Gurd S, Provencher C, Beaulieu P, Hudson TJ, Sladek R, Majewski J. 2008. "Genome-wide analysis of transcript isoform variation in humans" Nat Genet 40: 225-31.

McCarroll SA. 2008. "Extending genome-wide association studies to copy-number variation" Hum Mol Genet 17: R135-42.

Eberwine J, Kacharmina JE, Andrews C, Miyashiro K, McIntosh T, Becker K, Barrett T, Hinkle D, Dent G, Marciano P. 2001. "mRna expression analysis of tissue sections and single cells" J Neurosci 21: 8310-4.

Kolb HC, Finn MG, B. SK. 2001. "Click Chemistry: Diverse Chemical Function from a Few Good Reactions" Angew. Chem. Int. 40: 2004-21.

Kwiatkowski M, Fredriksson S, Isaksson A, Nilsson M, Landegren U. 1999. "Inversion of in situ synthesized oligonucleotides: improved reagents for hybridization and primer extension in DNA microarrays" Nucleic Acids Res 27: 4710-4. PMC Id: PMC148770.

Li JB, Gao Y, Aach J, Zhang K, Kryukov GV, Xie B, Ahlford A, Yoon J-K, Rosenbaum AM, Wait-Zaranek A, LeProust E, Sunyaev S, Church GM. 2009. "Multiplex padlock capture and sequencing reveal human hypermutable CpG variations" Genome Res in press.

Mitra RD, Butty VL, Shendure J, Williams BR, Housman DE, Church GM. 2003. "Digital genotyping and haplotyping with polymerase colonies" Proc Natl Acad Sci U S A 100: 5926-31. PMC Id: PMC156303.

Pan X, Urban AE, Palejev D, Schulz V, Grubert F, Hu Y, Snyder M, Weissman SM. 2008. "A procedure for highly specific, sensitive, and unbiased whole-genome amplification" Proc Natl Acad Sci U S A 105: 15499-504. PMC Id: PMC2563063.

Stougaard M, Lohmann JS, Zajac M, Hamilton-Dutoit S, Koch J. 2007. "In situ detection of non-polyadenylated RNA molecules using Turtle Probes and target primed rolling circle PRINS" BMC Biotechnol 7: 69. PMC Id: PMC2203993.

(56)                    References Cited

OTHER PUBLICATIONS

Wang Z, Gerstein M, Snyder M. 2009. "RNA-Seq: a revolutionary tool for transcriptomics" Nat Rev Genet 10: 57-63.

Wu J, Zhang S, Meng Q, Cao H, Li Z, Li X, Shi S, Kim DH, Bi L, Turro NJ, Ju J. 2007. "3'-O-modified nucleotides as reversible terminators for pyrosequencing" Proc Natl Acad Sci U S A 104: 16462-7. PMC Id: PMC2034218.

Zhang K, Li JB, Gao Y, Egli D, Xie B, Deng J, Li Z, Lee J, Aach J, Leproust E, Eggan K, Church GM. 2009. "Digital RNA Allelotyping Reveals Tissue-specific and Allele-specific Gene Expression in Human" (submitted to Nature Methods).

Bakal C, Aach J, Church G, Perrimon N. 2007. "Quantitative morphological signatures define local signaling networks regulating cell morphology" Science 316: 1753-6.

Office Action issued for corresponding European Patent Application No. 12780609.9, dated Sep. 23, 2015.

Seo, et al. Four-color DNA sequencing by synthesis on a chip using photocleavable fluorescent nucleotides. Proceeding of the National Academy of Sciences, Apr. 2005, 102 (17) 5926-5931.

Brenner, et al. "Gene expression analysis by massively parallel signature sequencing (MPSS) on microbead arrays". Nature Bio-technology vol. 18, pp. 630-634 (2000) doi: 10.1038/76469.

Dec. 18, 2014 (PCT) International Preliminary Report—App PCT/US2013/044241.

Shendure Jay et al., "Accurate multiplex polony sequencing of an evolved bacterial genome," Science, American Association for the Advancement of Science, Washington, DC; US, vol. 309, No. 5741, Sep. 1, 2005, pp. 1728-1732, XP002427180, ISSN: 0036-8075, DOI: 10.1126/SCIENCE.1117839.

Extended European Seach Report issued in corresponding European Application No. 12860433.7, dated Aug. 13, 2015.

International Search Report and Written Opinion issued in corresponding International Application No. PCT/US2012/071398, mailed Apr. 8, 2013.

Benner et al. "Gene Expression analysis by massively parallel signature sequencing (MPSS) on microbead arrays". Nature Bio-technology, vol. 18, pp. 630-634 (Jun. 31, 2000).

Han et al. "Quantum-dot-tagged microbeads for multiplexed optical coding of biomolecules". Nature Biotechnology, vol. 19, 99. 631-635 (Jul. 31, 2001).

Lee, JH et al. Highly Multiplexed Subcellular RNA Sequencing In Situ. Science. Mar. 21, 2014, vol. 343, No. 6177; pp. 1360-1363; abstract; p. 1360, second column, second paragraph to third column, first paragraph; p. 1361, first column, first paragraph; p. 1363, first column, second paragraph to second column, first paragraph; DOI: 10.1126/science.1250212.

Ascano, M et al. Identification of RNA-Protein Interaction Net-works Using PAR-CLIP. Wiley Interdiscip Rev RNA. Mar. 2012, vol. 3, No. 2; pp. 159-177; p. 3, third paragraph; p. 16, figure 1; p. 25, figure 6; DOI: 10.1002/wrna. 1103.

Ginart, P et al. RNA Sequencing In Situ. Nat Biotechnol. Jun. 2014, vol. 32, No. 6; pp. 543-544; DOI: 10.1038/nbt.2921.

Saliba, AE et al. Single-Cell RNA-Seq: Advances and Future Challenges. Nucleic Acids Res. Jul. 22, 2014, vol. 42, No. 14; pp. 8845-8860; DOI: 10.1093/nar/gku555.

Eliscovich et al. mRNA on the move: The road to its biological destiny. Journal of Biological Chemistry, vol. 288, No. 28, pp. 20361-20368, Jul. 2013, in press May 2013 (Year: 2013).

Weis et al. Protein targeting to subcellular organelles via mRNA localization. Biochimica et Biophysica Acta, vol. 1833, pp. 260-273, 2013, available online Apr. 2012 (Year: 2012).

Jambhekar et al. Cis-acting determinants of asymmetric, cytoplas-mic RNA transport. RNA, vol. 13, pp. 625-642, 2007 (Year: 2007).

Singer-Kruger et al. Here, there, everywhere. RNA Biology, vol. 11, No. 8, pp. 1031-1039, Aug. 2014. (Year: 2014).

Matlin et al. Spatial expression of the genome: the signal hypothesis at forty. Nature Reviews. Molecular Cell Biology, vol. 12, No. 5, pp. 333-340, May 2011, Epub Apr. 2011. (Year: 2011).

Polidoros et al. Rolling circle amplification-RACE: a method for simultaneous isolation of 5' and 3' cDNA ends from amplified cDNA templates. Bio Techniques, vol. 41, No. 1, pp. 35, 36, 38 and 40, Jul. 2006, including p. 1/1 of Supplementary Material. (Year: 2006).

Tsaftaris et al. Isolation of three homologous AP1-like MADS-box genes in crocus (Crocus sativus L.) and characterization of their expression. Plant Science, vol. 166, No. 5, pp. 1235-1243, May 2004. (Year: 2004).

Meeks et al. Characterization of genes encoding poly(A) polymerases in plants: Evidence for duplication and functional specialization. PLoS ONE, vol. 4, No. 11, e8082, Nov. 2009, printed as pp. 1/10-10/10. (Year: 2009).

Kalivas et al. famRCA-RACE: A rolling circle amplification RACE for isolating a family of homologous cDNAs in one reaction . . . Preparative Biochemistry and Biotechnology, vol. 40, No. 3, pp. 177-187, Jul. 2010. (Year: 2010).

Thisse et al. "High-Resolution in situ hybridization to whole-mount zebrafish embryos" 2008. Nature Protocols. vol. 3 No. 1 pp. 59-69. Doi:10.1038/nprot.2007.514.

Grompe (1993) Nature Genetics DOI: 10.1038/ng1093-111.

Thisse et al. 2008 Nature protocols vol. 3 No. 1 pp. 59-69. Doi: 10.1038/nprot.2007.514.

Doillon et al. "Actin Filaments in Normal Dermis and During Wound Healing" The American Journal of Pathology, vol. 126 Issue 1 (1987): pp. 164-170; p. 164 col 1 para 1, p. 170 col 1 para 2, fig. 4A-C.

International Search Report and Written Opinion based on PCT/US2018/027583 issued Jun. 29, 2018.

Soderberg, Ola et al., "Direct observation of individual endogenous protein complexes in situ by proximity ligation," Nature Methods, Dec. 2006, pp. 995-1000, vol. 3, No. 12, Nature Publishing Group.

Schweitzer, Barry et al., "Immunoassays with rolling circle DNA amplification: A versatile platform for ultrasensitive antigen detec-tion" PNAS, Aug. 29, 2000, pp. 10113-10119, vol. 97, No. 18.

Cao, Yi et al.,"In-situ immuno-PCR to detect antigens," The Lancet, Sep. 16, 2000, pp. 1002-1003, vol. 356.

Sano, Takeshi et al. "Immuno-PCR: Very Sensitive Antigen Detec-tion by Means of Specific Antibody-DNA Conjugates," Science, Oct. 2, 1992, pp. 120-122, vol. 258.

Dasari, Vivek et al., "Platform for Spatial Molecular Data by Vivek Dasari 1-7 Sig nature redacted Thesis Supervisor", Aug. 20, 2015 (Aug. 20, 2015), XP055559164, Retreived from the Internet: URL:http://dspace.mit.edu/bitstream/handle/1721.1/107103/971494098-MIT.pdf?sequence=1 [retreived on Feb. 20, 2019].

Extended European Search Report issued May 13, 2019 for EP Application No. 16862929.3.

Lee, Je Hyuk et al., "Fluorescent in situ sequencing (FISSEQ) or RNA for gene expression profiling in intact cells and tissues", Nature Protocols, vol. 10, No. 3, Feb. 12, 2015 (Feb. 12, 2015), pp. 442-458. XP055272042, GB ISSN: 1754-2189, DOI: 10.1038/nprot. 2014.191.

Extended European Search Report issued May 21, 2019 for Euro-pean Application No. 16862945.9.

Choi, Harry M.T. et al., "Next-Generation in Situ Hybridization Chain Reaction: Higher Gain, Lower Cost, Greater Durability" ACS Nano, vol. 8, No. 5, May 27, 2014 (May 27, 2014), pp. 4284-4294, XP055409053, US.

Ravan, Hadi, et al. "Isothermal RNA detection through the forma-tion of DNA concatemers contiaining HRP-mimicking DNAzymes on the surface of gold nanoparticles", Biosensors and Bioelectron-ics, Elsevier Science Ltd. UK, Amsterdam, NL, vol. 80, Jan. 18, 2016 (Jan. 18, 2016), pp. 67-73, XP029441324.

Extended European Search Report issued for EP Application No. 17790240.0 on Sep. 4, 2019.

Brown et al., Review Article : In situ Hybridization with Riboprobes : An Overview for Veterinary Pathologists. Veterinary Pathology 35 : 159-167 (Year: 1998).

Choi et al.,Programmable in situ amplification for multiplexed imaging of mRNA expression. Nature Biotechnology 28 (11): 1208 (Year: 2010).

Choi & Love et al., Immuno-Hybridization Chain Reaction for Enhancing Detection of Individual Cytokine-Secreting Human Periph-eral Mononuclear Cells. Analytical Chemistry 83 : 6890-6895 (Year: 2011).

(56)　　　　References Cited

OTHER PUBLICATIONS

Hansen et al., Sensitive ligand-based protein quantification using immuno-PCR: A critical review of single-probe and proximity ligation assays. Biotechniques 56:217-228 (Year: 2014).

Kuimelis et al., Cleavage properties of an oligonucleotide containing a bridged internucleotide 5-phosphorothioate RNA linkage. Nucleic Acids Research 23 (23) : 4753-4760 (Year: 1999).

Mag et al., Synthesis and selective cleavage of an oligodeoxynucleotide containing a bridged internucleotide 5'-phosphorothioate linkage. Nucleic Acids Research 19(7): 1437 (Year: 1991).

Richardson et al., Experimental and Theoretical Studies of Light-to-Heat Conversion and Collective Heating Effects in Metal Nanoparticle Solutions. Nano Letters 9(3) : 1139-1146 (Year: 2009).

Song et al., Hybridization chain reaction-based aptameric system for the highly selective and sensitive detection of protein. Analyst 137: 1396 (Year: 2012).

Xiao et al., Single-step electronic detection of femtomolar DNA by target-induced strand displacement in an electrode-bound duplex. PNAS 103(45): 16677-16680 (Year: 2006).

Zhang et al., Dynamic DNA nanotechnology using strand-displacement reactions. Nature Chemistry 3 : 103-113 (Year: 2011).

Zhao et al., An electrochemical aptasensor based on hybridization chain reaction with enzyme-signal amplification for Interferon-gamma detection. Biosensors and Bioelectronics 36: 129-134 (Year: 2012).

Srinivas et al., On the biophysics and kinetics of toehold-mediated DNA strand displacement. Nucleic Acids Research 41 (22) : 10641-10658 (Year: 2013).

Li JB, Levanon EY, Yoon J-K, Aach J, Xie B, LeProust E, Zhang K, Gao Y, G.M. C. 2009. "Genome-wide Identification of Human RNA Editing Sites by Parallel DNA Capturing and Sequencing" Science in press.

Meng Q, Kim DH, Bai X, Bi L, Turro NJ, Ju J. 2006. "Design and synthesis of a photocleavable fluorescent nucleotide B'-O-allyl-dGTP-PC-Bodipy-FL-510 as a reversible terminator for DNA sequencing by synthesis" J Org Chem 71: 3248-52.

Mitra RD, Shendure J, Olejnik J, Edyta Krzymanska O, Church GM. 2003. "Fluorescent in situ sequencing on polymerase colonies" Anal Biochem 320: 55-65.

Porreca GJ, Shendure J, Church GM. 2006. "Polony DNA sequencing" Curr Protoc Mol Biol Chapter 7: Unit 7 8.

Porreca GJ, Zhang K, Li JB, Xie B, Austin D, Vassallo SL, LeProust EM, Peck BJ, Emig CJ, Dahl F, Gao Y, Church GM, Shendure J. 2007. "Multiplex amplification of large sets of human exons" Nat Methods 4: 931-6.

Shendure J, Mitra RD, Varma C, Church GM. 2004. "Advanced sequencing technologies: methods and goals" Nat Rev Genet 5: 335-44.

Shendure JA, Porreca GJ, Church GM. 2008. "Overview of DNA sequencing strategies" Curr Protoc Mol Biol Chapter 7: Unit 7 1.

Tang F, Barbacioru C, Wang Y, Nordman E, Lee C, Xu N, Wang X, Bodeau J, Tuch BB, Siddiqui A, Lao K, Surani MA. 2009. "mRNA-Seq whole-transcriptome analysis of a single cell" Nat Methods 6: 377-82.

Vigneault F, Sismour AM, Church GM. 2008." Efficient microRNA capture and bar-coding via enzymatic oligonucleotide adenylation" Nat Methods 5: 777-9.

Zhang K, Martiny AC, Reppas NB, Barry KW, Malek J, Chisholm SW, Church GM. 2006. "Sequencing genomes from single cells by polymerase cloning" Nat Biotechnol 24: 680-6.

Zhang K, Zhu J, Shendure J, Porreca GJ, Aach JD, Mitra RD, Church GM. 2006. "Long-range polony haplotyping of individual human chromosome molecules" Nat Genet 38: 382-7.

Church et al.; Center for Casual Consequences of Variation (CCV) "An NHGRI Center for Excellence in Genomic Science" https://web.archive.org/web/20110703211120/http://ccv.med.harvard.edu/; Wayback Machine (Jul. 3, 2011).

Church et al.; Center for Casual Consequences of Variation (CCV) "Our four Specific Aims" https://web.archive.org/web/

20110813071548//http://ccv.med.harvard.edu/specific_aims.htm; Wayback Machine (Aug. 13, 2011).

Church; "Proposal for a Center for the determination of the Casual Transcriptional Consequences of Human Genetic Variation (CTCHGV)" http://ccv.med.harvard.edu/CEGS09_Complete_Proposal_minus_Admin_Sections.09May21.final.pdf; Wayback Machine (Aug. 13, 2011).

J. H. Lee, M.D. Ph.D. presentation entitled "Population-wide Tissue-specific Functional Analysis of Human iPS Cells Using Single-Cell In Situ Sequencing" George Church Laboratory, Wyss Institute for Biology Inspired Engineering, Harvard Medical School, Boston, Jan. 10, 2010.

May 17, 2021 (US) Notice of Allowance—Appln No. 17/122,168.

Jun. 18, 2021 (US) Non-Final Office Action—Appln No. U.S. Appl. No. 15/772,652.

May 8, 2021—(CN) Office Action—App. No. 201680077501.7.

Jul. 2, 2021—(US) Non-Final Office Action—Appln No. U.S. Appl. No. 17/238,642.

Jul. 21, 2021 (US) Non-Final Office Action—U.S. Appl. No. 16/693,611.

Ho et al. "Sequencing by ligation variation with endonuclease V digestion and deoxyinosine-containing query oligonucleotides" BMC Genomics, 2011, 12:598.

Jiang et al. "Solar thermal polymerase chain reaction for smartphone-assisted molecular diagnostics" Scientific Reports, 4:4137, 2014.

Ju et al. "Four-color DNA sequencing by synthesis using cleavable fluorescent nucleotide reversible terminators" PNAS, Dec. 26, 2006, vol. 103, No. 52, pp. 19635-19640.

Lubeck et al. "Single cell in situ RNA profiling by sequential hybridization" Nature Methods, Apr. 2014, 11(4), pp. 360-361.

Parinov et al. "DNA sequencing by hybridization to microchip octa- and decanucleotides extended by stacked pentanucleotides" Nucleic Acids Research, 1996, vol. 24, No. 15, pp. 2998-3004.

Schouten et al. "Relative quantification of 40 nucleic acid sequences by multiplex ligation-dependent probe amplification" Nucleic Acids Research, 2002, vol. 30, No. 12, e57.

Jul. 23, 2021 (US) Non-Final Office Action—U.S. Appl. No. 16/170,751.

Aug. 16, 2021—(US) Non-Final Office Action—Appln No. U.S. Appl. No. 17/363,097.

Guo et al. "Target-driven DNA association to initiate cyclic assembly of hairpins for biosensing and logic gate operation" Chemical Science, 2015, 6, pp. 4318-4323.

Aug. 10, 2021—(GB) Examination Report—App. No. 1904335.5.

Tillberg et al., "Protein-retention expansion microscopy of cells and tissues labeled using standard fluorescent proteins and antibodies," Nat Biotechnol., vol. 34, No. 9, pp. 987-992 (2016).

Chen et al., "Nanoscale imaging of RNA with expansion microscopy," Nature Methods, vol. 133, No. 8, pp. 679-684 (Aug. 1, 2016).

Jul. 6, 2021—(JP) Notice of Reasons for Rejection—App. No. 2019-511929.

Oct. 5, 2021—(EP) Summons to Oral Proceedings—App. No. 17790240.0.

Wang et al. "Rapid and Sensitive Detection of Severe Acute Respiratory Syndrome Coronavirus by Rolling Circle Amplification" Journal of Clinical Microbiology, vol. 43, No. 5, May 2005, pp. 2339-2344.

Nov. 1, 2021—(US) Final Office Action—U.S. Appl. No. 16/830,372.

Oct. 5, 2021—(JP) Notice of Reasons for Rejection—App. No. 2019-511921.

Goransson et al. "A single molecule array for digital targeted molecular analyses" Nucleic Acids Research, 2009, vol. 37, No. 1, e7, doi:10.1093/nar/gkn921.

Dirks et al. "Triggered amplificaiton by hybridization chain reaction" PNAS; Oct. 26, 2004; vol. 101, No. 43, pp. 15275-15278.

Lubeck et al. "Single cell systems biology by super-resolution imaging and combinatorial labeling" Nature Methods; 9 (7); pp. 743-748; 2012.

Nov. 23, 2021 (US)—Non-Final Office Action—U.S. Appl. No. 17/392,325.

Nov. 30, 2021—(US) Final Office Action—U.S. Appl. No. 15/772,652.

Chen et al. "Functional organization of the human 4D Nucleome" PNAS, vol. 112, No. 26, Jun. 15, 2015, pp. 8002-8007.

(56) References Cited

OTHER PUBLICATIONS

Jarvius et al. "Digital quantification using amplified single-molecule detection" Nature Methods, vol. 3, No. 9, Sep. 2006, pp. 725-727.
Jan. 25, 2022—(US) Non-Final Office Action—Appl No. 17/266,151.
Dec. 16, 2021—(CN) Office Action—App. No. 201780039335.6.
Jan. 28, 2022—(US) Non-Final Office Action—Appl No. 17/366,127.
Dirks et al. "Triggered amplification by hybridization chain reaction" PNAS; Oct. 26, 2004; vol. 101, No. 43, pp. 15275-15278.
Feb. 18, 2022 (US)—Final Office Action—U.S. Appl. No. 16/170,751.
Mar. 4, 2022—(US) Non-Final Office Action—U.S. Appl. No. 17/395,534.
Christian et al. "Detection of DNA point mutations and mRNA expression levels by rolling circle amplification in individual cells" PNAS; vol. 98; No. 25; Nov. 27, 2001; pp. 14238-14243.
"TCS-SP5 Ver2.0 Manual," Leica Microsystems, Inc., Feb. 21, 2011, pp. 1-11, 15, 24-26, 153.
"LSM 710 and ConfoCor 3 Operating Manual," Carl Zeiss MicroImaging GmbH, Apr. 2009, pp. 7-13, 44-47, 73-74, 77-81.
Douse et al. "Multiplexed and Reiterative Fluorescence Labeling via DNA Circuitry" Bioconjug Chem. Dec. 15, 2010,21 (12):2327-31. doi: 10.1021/bc100348q. Epub Nov. 16, 2010. (Supporting Information).
Douse et al. "Multiplexed and Reiterative Fluorescence Labeling via DNA Circuitry" Bioconjug Chem. Dec. 15, 2010;21 (12):2327-31. doi: 10.1021/bc100348q. Epub Nov. 16, 2010.
Choi et al. "Programmable in situ amplification for multiplexed bioimaging" Nature Biotechnology 28: 1208-1212, Oct. 2010, Supplementary Information.
Muller et al. "Towards unlimited colors for fluorescence in-situ hybridization (FISH)" Chromosome Research; 10: 223-232, 2002.
Feb. 8, 2022—(JP) Notice of Reasons for Rejection—App. No. 2021-028931.
Mar. 22, 2022—(US) Final Office Action—U.S. Appl. No. 17/392,325.
Bibikova et al. "Quantitative Gene Expression Profiling in Formalin-Fixed, Paraffin-Embedded Tissues Using Universal Bead Arrays" American Journal of Pathology, vol. 165, No. 5, Nov. 2004.
Capodieci et al. "Gene expression profiling in single cells within tissue" Nature Methods, Sep. 14, 2005, 2(9) pp. 663-665.
Conze et al. "Single molecule analysis of combinatorial splicing" Nucleic Acids Research, Jun. 29, 2010, vol. 38, No. 16; e163.
Femino et al. "Visualization of Single RNA Transcripts in Situ" Science, Apr. 24, 1998, vol. 280, pp. 585-590.
Gavrilovic et al. "Automated Classification of Multicolored Rolling Circle Products in Dual-Channel Wide-Field Fluroescence Microscopy" Cytometry Part A, Jul. 2011, 79(7), pp. 518-527.
Geiss et al. "Direct multiplexed measurement of gene expression with color-coded probe pairs" Nature Biotechnology, vol. 26, No. 3, Mar. 2008, pp. 317-325.
Gunderson et al. "Decoding Randomly Ordered DNA Arrays" Genome Research, May 2004, 14(5), pp. 870-877.
Han et al. "Quantum-dot-tagged microbeads for multiplexed optical coding of biomolecules" Nature Biotechnology, Jul. 2001, vol. 19, No. 7, pp. 631-635.
Itzkovitz et al. "Validating Transcripts with Probes and Imaging Technology" Nature Methods, Apr. 2011, 8(4 Suppl): S12-S19.
Itzkovitz et al. "Single molecule transcript counting of stem cell markers in the mouse intestine" Nat Cell Biol., Nov. 2011, 14(1), pp. 106-114.
Lagunavicius et al. "Novel application of Phi29 DNA polymerase: RNA detection and analysis in vitro and in situ by target RNA-primed RCA" RNA, May 2009, 15(5), pp. 765-771.
Levsky et al. "Fluorescence in situ hybridization: past, present and future" Journal of Cell Science, Jul. 15, 2003, 116 (Pt 14), pp. 2833-2838.
Levsky et al. "Single-Cell Gene Expression Profiling" Science, Aug. 2, 2002, 297(5582), pp. 836-840.
Maierhofer et al. "Multicolor Deconvolution Microscopy of Thick Biological Specimens" American Journal of Pathology, vol. 162, No. 2, Feb. 2003, pp. 373-379.

Meade et al. "Multiplexed DNA detection using spectrally encoded porous" Analytical Chemistry, Apr. 1, 2009, 81(7), pp. 2618-2625.
Meade et al. "Multiplexed DNA detection using spectrally encoded porous SiO2 phtonic crystal particles" Analytical Chemistry, Apr. 1, 2009, 81(7), pp. 2618-2625.
Raj et al. "Imaging individual mRNA molecules using multiple singly labeled probes" Nature Methods, Oct. 2009, 5 (10), pp. 877-879.
Sun et al. "Composite Organic-Inorganic Nanoparticles as Raman Labels for Tissue Analysis" Nano Letters, Feb. 2007, vol. 7, No. 2, pp. 351-356.
Wahlby et al. "Sequential Immunofluorescence Staining and Image Analysis for Detection of Large Numbers of Antigens in Individual Cell Nuclei" Cytometry, Jan. 1, 2002, 47(1), pp. 32-41.
Weibrecht et al. "Simultaneous Visualization of Both Signaling Cascade Activity and End-Point Gene Expression in Single Cells" PLoS One, May 2011, vol. 6, Issue 5, e20148.
Wilson et al. "Encoded Microcarriers For High-Throughput Multiplexed Detection" Angewandte Chemie International Edition, Sep. 18, 2006, 45(37), pp. 6104-6117.
Zhao et al. "Advances of multiplex and high throughput biomolecular detection technologies based on encoding microparticles" Science China Chemistry, Aug. 2011, vol. 54, No. 8, pp. 1185-1201.
Jun. 14, 2022—(US) Non-Final Office Action—U.S. Appl. No. 17/584,959.
Jun. 1, 2022—(EP) Examination Report—App. No. 16862929.3.
Ng et al., "Surface-based mapping of gene expression and probabilistic expression maps in the mouse cortex," Methods, vol. 50, No. 1, pp. 55-62 (Feb. 1, 2010).
Jun. 29, 2022—(US) Non-Final Office Action—U.S. Appl. No. 17/671,803.
Jul. 5, 2022—(JP) Notice of Reasons for Rejection—App. No. 2019-511921.
Leuchowius et al. "Parallel visualization of multiple protein complexes in individual cells in tumor tissue" Molecular & Cellular Proteomics; vol. 12; No. 6; pp. 1563-1571; Jun. 2013; published online Feb. 22, 2013.
Marblestone et al. "Rosetta Brains: A strategy for molecularly-annotated connectomics" arXiv:1404.5103v1 -q-bio.NC], https://doi.org/10.48550/arXiv.1404.5103, pp. 1-18; Apr. 21, 2014.
Jul. 21, 2022—(US) Non-Final Office Action—U.S. Appl. No. 16/200,831.
Schubert et al. "Analyzing proteome topology and function by automated multidimensional fluorescence microscopy" Nature Biotechnology; Oct. 1, 2006; 24(10); pp. 1270-1278.
Chen, et al. "Spatially resolved, highly multiplexed RNA profiling in single cells". Science. Apr. 24, 2015;348(6233):aaa6090, pp. 1-14.
Tam, et al. A microfluidic platform for correlative live-cell and super-resolution microscopy. PloS one. Dec. 29, 2014;9 (12):e115512, pp. 1-20.
Bálint, et al. Correlative live-cell and superresolution microscopy reveals cargo transport dynamics at microtubule intersections. Proceedings of the National Academy of Sciences. Feb. 26, 2013;110(9): pp. 3375-3380.
Manders, et al. Direct imaging of DNA in living cells reveals the dynamics of chromosome formation. The Journal of cell biology. Mar. 8, 1999;144(5):813-822.
Larsson et al. "In situ genotyping individual DNA molecules by target-primed rolling-circle amplification of padlock probes" Nature Methods, vol. 1; No. 3; Dec. 2004; pp. 227-232.
Crosetto: "Spatially resolved ranscriptomics and beyond", Nature Review Genetics, Jan. 1, 2015 (Jan. 1, 2015), pp. 57-66, XP055284555, DOI: 10.1038/nrg3832 Retrieved from the Internet: URL:http://www.nature.com/nrg/journal/v16/n1/pdf/nrg3832.pdf [retrieved on Jun. 29, 2016.
Sekar et al. "Fluorescence resonance energy transfer (FRET) microscopy imaging of live cell protein localizations" Journal of Cell Biology; vol. 160; No. 5; Mar. 3, 2003; pp. 629-633.
Morley M, Molony CM, Weber TM, Devlin JL, Ewens KG, Spielman RS, Cheung VG. 2004. "Genetic analysis of genome-wide variation in human gene expression" Nature 430: 743-7.

(56)         References Cited

OTHER PUBLICATIONS

Schadt EE, Molony C, Chudin E, Hao K, Yang X, Lum PY, Kasarskis A, Zhang B, Wang S, Suver C, Zhu J, Millstein J, Sieberts S, Lamb J, GuhaThakurta D, Derry J, Storey JD, Avila-Campillo I, Kruger MJ, Johnson JM, Rohl CA, van Nas A, Mehrabian M, Drake TA, Lusis AJ, Smith RC, Guengerich FP, Strom SC, Schuetz E, Rushmore TH, Ulrich R. 2008. "Mapping the genetic architecture of gene expression in human liver" PLoS Biol 6: e107. PMC ID: PMC2365981.

Serre D, Gurd S, Ge B, Sladek R, Sinnett D, Harmsen E, Bibikova M, Chudin E, Barker DL, Dickinson T, Fan JB, Hudson TJ. 2008. "Differential allelic expression in the human genome: a robust approach to identify genetic and epigenetic cis-acting mechanisms regulating gene expression" PLoS Genet 4: e1000006. PMC ID: PMC2265535.

Ball MP, Li JB, Gao Y, Lee J, LeProust E, Park I-H, Xie B, Daley GQ, Church GM. 2009. "Targeted and whole-genome methylomics reveals gene-body signatures in human cell lines" Nat Biotechnol 27: 361-8.

Brenner S, Williams SR, Vermaas EH, Storck T, Moon K, McCollum C, Mao JI, Luo S, Kirchner JJ, Eletr S, DuBridge RB, Burcham T, Albrecht G. 2000. "In vitro cloning of complex mixtures of DNA on microbeads: physical separation of differentially expressed cDNAs" Proc Natl Acad Sci U S A 97: 1665-70. PMC ID: PMC26493.

Chiang DY, Getz G, Jaffe DB, O'Kelly MJ, Zhao X, Carter SL, Russ C, Nusbaum C, Meyerson M, Lander ES. 2009. "High-resolution mapping of copy-number alterations with massively parallel sequencing" Nat Methods 6: 99-103. PMC ID: PMC2630795.

Choy E, Yelensky R, Bonakdar S, Plenge RM, Saxena R, De Jager PL, Shaw SY, Wolfish CS, Slavik JM, Cotsapas C, Rivas M, Dermitzakis ET, Cahir-McFarland E, Kieff E, Hafler D, Daly MJ, Altshuler D. 2008. "Genetic analysis of human traits in vitro: drug response and gene expression in lymphoblastoid cell lines" PLoS Genet 4: e1000287. PMC ID: PMC2583954.

Christian AT, Pattee MS, Attix CM, Reed BE, Sorensen KJ, Tucker JD. 2001. "Detection of DNA point mutations and RNA expression levels by rolling circle amplification in individual cells" Proc Natl Acad Sci U S A 98: 14238-43. PMC ID: PMC64666.

Church GM, Porreca GJ, Terry RC, Lares M. 2008. "High Speed Imaging for DNA Sequencing" Biophotonics (<http://www.photonics.com/Content/ReadArticle.aspx?ArticleID=33989>).

Peng J, Shoemaker R, Xie B, Gore A, LeProust EM, Antosiewicz-Bourget J, Egli D, Maherali N, Park IH, Yu J, Daley GQ, Eggan K, Hochedlinger K, Thomson J, Wang W, Gao Y, Zhang K. 2009. "Targeted bisulfite sequencing reveals changes in DNA methylation associated with nuclear reprogramming" Nat Biotechnol 27: 353-60.

Bang D, Church GM. 2008. "Gene synthesis by circular assembly amplification" Nat Methods 5: 37-9.

Bell J. 2004. "Predicting disease using genomics" Nature 429: 453-6.

Harris TD, Buzby PR, Babcock H, Beer E, Bowers J, Braslavsky I, Causey M, Colonell J, Dimeo J, Efcavitch JW, Giladi E, Gill J, Healy J, Jarosz M, Lapen D, Moulton K, Quake SR, Steinmann K, Thayer E, Tyurina A, Ward R, Weiss H, Xie Z. 2008. "Single-molecule DNA sequencing of a viral genome" Science 320: 106-9.

Kim JB, Porreca GJ, Song L, Greenway SC, Gorham JM, Church GM, Seidman CE, Seidman JG. 2007. "Polony multiplex analysis of gene expression (PMAGE) in mouse hypertrophic cardiomyopathy" Science 316: 1481-4.

Kurimoto K, Yabuta Y, Ohinata Y, Saitou M. 2007. "Global single-cell cDNA amplification to provide a template for representative high-density oligonucleotide microarray analysis" Nat Protoc 2: 739-52.

* cited by examiner

1. Analyze *in situ* 'omics' data
   * FISSEQ
   * Protein
   * epigenome

2. Integrate with spatial analysis
   * morphology
   * cell interactions
   * tissue architecture

METHODS OF COMBINING THE DETECTION OF BIOMOLECULES INTO A SINGLE ASSAY USING FLUORESCENT IN SITU SEQUENCING

RELATED APPLICATION DATA

This application is a continuation application which claims priority to U.S. application Ser. No. 16/288,200 and filed Feb. 28, 2019; which is a continuation application which claims priority to PCT Application No. PCT/US17/49641 designating the United States and filed Aug. 31, 2017; which claims the benefit of U.S. Provisional Application No. 62/381,997 and filed Aug. 31, 2016 each of which are hereby incorporated by reference in their entireties.

STATEMENT OF GOVERNMENT RIGHTS

This invention was made with government support under HG005550 and HG008525 awarded by National Institutes of Health (NIH) and under 1144152 awarded by National Science Foundation (NSF). The government has certain rights in this invention.

BACKGROUND OF THE INVENTION

The transcriptome is an important mediator of cellular phenotype. Cellular RNA reflects the state of the genome, and also generates all the proteins that comprise the primary material manifestation of the cell. Therefore, it is believed that detecting RNA molecules generates tremendous insight into cellular phenotype. Detecting RNA, however, only allows making inferences about the state of the genome, the proteome, the metabolome, and the dimensions of molecular state space. There remains a need for methods that combine RNA fluorescent in situ sequencing (FISSEQ) with other molecular detection modalities, forming an integrated panomic detection platform.

SUMMARY OF THE INVENTION

In one aspect, the present disclosure provides a system for use in detection or identification of one or more biomolecules of a biological sample. The system may comprise: a container comprising (i) said biological sample comprising said one or more biomolecules, and (ii) a swelling agent and attachment moieties, wherein said swelling agent is activatable upon application of a stimulus to increase in volume to yield a three-dimensional matrix comprising said biomolecules, wherein said stimulus is an electromagnetic stimulus, an electrochemical stimulus, or a thermal stimulus, wherein said one or more biomolecules are coupled to said three-dimensional matrix via said attachment moieties, and wherein said three-dimensional matrix preserves an absolute or relative spatial relationship of said biomolecules within the biological sample.

In another aspect, the present disclosure also provides a system for use in detection or identification of one or more biomolecules of a biological sample. The system may comprise: a container comprising (i) said biological sample comprising said one or more biomolecules, and (ii) a swelling agent and attachment moieties, wherein said swelling agent is activatable upon application of a stimulus to yield a three-dimensional matrix comprising said biomolecules, wherein said stimulus is not a liquid, wherein said one or more biomolecules are coupled to said three-dimensional matrix via said attachment moieties, and wherein said three-dimensional matrix preserves an absolute or relative spatial relationship of said biomolecules within the biological sample.

In some embodiments, said three-dimensional matrix comprises said biological sample comprising said biomolecules. In some embodiments, the system further comprises a source of said stimulus operatively coupled to said container, wherein application of said stimulus to said swelling agent activates said swelling agent to form said three-dimensional polymer matrix, which three-dimensional polymer matrix preserves an absolute or relative spatial relationship of said biomolecules within said biological sample. In some embodiments, the system further comprises one or more computer processors operatively coupled to said source of said stimulus, wherein said one or more computer processors are individually or collectively programmed to direct said source of said stimulus to apply said stimulus to said swelling agent, thereby activating said swelling agent to form said three-dimensional polymer matrix. In some embodiments, said biological sample is a cell or derivative thereof. In some embodiments, said biomolecules are ribonucleic acid molecules (RNA), deoxyribonucleic acid molecules (DNA), or RNA and DNA. In some embodiments, said electrochemical stimulus is an electrochemical reaction. In some embodiments, said swelling agent is further configured to act as a contracting agent. In some embodiments, said contracting agent is a light activated contracting agent, an electrochemically activated contracting agent, or a thermally activated contracting agent. In some embodiments, said swelling agent comprises chelation functionality. In some embodiments, said swelling agent comprises ethylenediaminetetraacetic acid (EDTA). In some embodiments, said EDTA is an ortho-nitrobenzyl caged EDTA or a quinone-ester protected EDTA. In some embodiments, the three-dimensional matrix is configured to swell by a factor of between 1.1 and 10 upon activation of the swelling agent. In some embodiments, the absolute or relative spatial relationship of said one or more biomolecules is preserved upon swelling of the three-dimensional matrix. In some embodiments, the attachment moieties comprise, or are operably coupled to a reactive group. In some embodiments, the attachment moieties comprise an amine, thiol, azide, alkyne, or a click reactive group. In some embodiments, the attachment moieties comprise a polymerizeable group.

In some embodiments, the present disclosure provides a method of using said three-dimensional matrix described herein, comprising: swelling the three-dimensional matrix via light, electrochemically, or thermally. In some embodiments, the method further comprises flowing reagents for fluorescent in situ sequencing (FISSEQ) into the three-dimensional matrix subsequent to said swelling. In some embodiments, the method further comprises contracting the three-dimensional matrix via light, electrochemically, or thermally.

In another aspect, a method for use in in situ detection or identification of biomolecules within a biological sample is provided. The method comprises: providing a container comprising (i) said biological sample comprising said biomolecules, and (ii) a swelling agent and attachment moieties, wherein said swelling agent is activatable upon application of a stimulus to yield a three-dimensional matrix comprising said biomolecules, wherein said stimulus is an electromagnetic stimulus, an electrochemical stimulus, or a thermal stimulus; and applying said stimulus to said swelling agent, thereby activating said swelling agent to yield the three-dimensional matrix comprising said biomolecules, wherein said biomolecules are coupled to said three-dimensional matrix via said attachment moieties, which three-dimensional matrix preserves an absolute or relative spatial relationship of said biomolecules within the biological sample.

In another aspect, the present disclosure also provides a method for use in in situ detection or identification of biomolecules within a biological sample. The method comprises: providing a container comprising (i) said biological sample comprising said biomolecules, and (ii) a swelling agent and attachment moieties, wherein said swelling agent is activatable upon application of a stimulus to yield a three-dimensional matrix comprising said biomolecules, wherein said stimulus is not a liquid; and applying said stimulus to said swelling agent, thereby activating said swelling agent to yield a three-dimensional matrix comprising said biomolecules, wherein said biomolecules are coupled to said three-dimensional matrix via said attachment moieties, which three-dimensional matrix preserves an absolute or relative spatial relationship of said biomolecules within the biological sample.

In some embodiments, said three-dimensional matrix comprises said biological sample comprising said biomolecules. In some embodiments, said biological sample is a cell or derivative thereof. In some embodiments, the method further comprises detecting at least a subset of said biomolecules in said three-dimensional matrix. In some embodiments, the method further comprises applying a source of said stimulus, wherein said source is operatively coupled to said container, wherein said applying activates said swelling agent to form said three-dimensional polymer matrix, which three-dimensional polymer matrix preserves an absolute or relative spatial relationship of said biomolecules within said biological sample. In some embodiments, said applying said source comprises directing said source of said stimulus to said swelling agent with aid of one or more computer processors individually or collectively programmed to direct said source.

In some embodiments, said swelling agent is further configured to act as a contracting agent.

In some embodiments, the method further comprises contracting the three-dimensional matrix via light, electrochemically, or thermally.

In another aspect, the present disclosure provides a polymerized three-dimensional matrix for identifying one or more biomolecules. The polymerized three-dimensional matrix comprises: a three-dimensional polymer comprising a backbone; and attachment moieties coupled to the backbone of the three-dimensional polymer, wherein the attachment moieties are configured to preserve an absolute or relative spatial relationship of the one or more biomolecules within the three-dimensional polymer, wherein the polymerized three-dimensional matrix does not comprise probes for identifying the one or more biomolecules.

In some embodiments, the attachment moieties are configured to capture the probes. In some embodiments, the three-dimensional polymer matrix is configured to capture the probes. In some embodiments, the polymerized three-dimensional matrix further comprises a biological sample integrated with the three-dimensional polymer, and wherein the attachment moieties are configured to preserve an absolute or relative spatial relationship of the one or more biomolecules within the biological sample. In some embodiments, the attachment moieties are configured to capture the probes which are coupled to said one or more biomolecules. In some embodiments, the backbone is a poly (ethylene glycol) backbone. In some embodiments, the attachment moieties are coupled to the backbone in a bottle brush topology. In some embodiments, the attachment moieties comprise a reactive group. In some embodiments, the attachment moieties comprise an amine, thiol, azide, alkyne, or a click reactive group. In some embodiments, the attachment moieties comprise a polymerizeable group.

In another aspect, the present disclosure also provides a method of detecting biomolecules using the polymerized three-dimensional matrix described herein comprising: providing the polymerized three-dimensional matrix; flowing in said probes to the polymerized three-dimensional matrix; and capturing the probes in the polymerized three-dimensional matrix. In some embodiments, the method further comprises detecting the probes. In some embodiments, the method further comprises sequencing a target sequence via the probes. In some embodiments, said flowing in the probes comprises flowing in the probes which are coupled to biomolecules to be detected by the probes. In some embodiments, said capturing said probes comprises capturing said probes via said attachment moieties.

In another aspect, the present disclosure provides a method for identifying one or more biomolecules. The method comprises: providing a container comprising said one or more biomolecules and a polymerized three-dimensional matrix comprising (i) a three-dimensional polymer comprising a backbone, and (ii) attachment moieties coupled to the backbone of the three-dimensional polymer, wherein the attachment moieties are configured to preserve an absolute or relative spatial relationship of the one or more biomolecules within the three-dimensional polymer, and wherein said three-dimensional matrix does not comprise probes for identifying said one or more biomolecules molecules; and directing said probes through said polymerized three-dimensional matrix.

In some embodiments, said one or more biomolecules are included in a cell or derivative thereof. In some embodiments, said one or more biomolecules are included in a cellular matrix derived from said cell. In some embodiments, the method further comprises capturing said probes within said polymerized three-dimensional matrix. In some embodiments, capturing said probes comprises capturing said probes via said attachment moieties. In some embodiments, said probes are coupled to said one or more biomolecules. In some embodiments, the method further comprises detecting said one or more biomolecules. In some embodiments, the method further comprises sequencing said one or more biomolecules. In some embodiments, the backbone is a poly (ethylene glycol) backbone. In some embodiments, the attachment moieties are coupled to the backbone in a bottle brush topology. In some embodiments, the attachment moieties comprise a reactive group. In some embodiments, the attachment moieties comprise an amine, thiol, azide, alkyne, or a click reactive group. In some embodiments, the attachment moieties comprise a polymerizeable group.

In another aspect, the present disclosure provides a method of detecting a plurality of biomolecules of a biological sample, comprising: providing said biological sample comprising a plurality of biomolecules of at least two different types; modifying said plurality of biomolecules in situ to comprise attachment moieties; linking said attachment moieties to a three-dimensional polymer matrix in situ, wherein said attachment moieties are configured to preserve an absolute or relative spatial relationship of said plurality of biomolecules within said biological sample; and detecting at least a subset of said plurality of biomolecules in situ.

In some embodiments, said biomolecules are detected optically. In some embodiments, said biomolecules are detected via fluorescence. In some embodiments, said biological sample is a cell or derivative thereof. In some embodiments, said biological sample is a cellular matrix derived from said cell. In some embodiments, the biomolecules comprise deoxyribonucleic acid (DNA), proteins, and small molecules. In some embodiments, the biomolecules comprise a protein, and said detecting comprises sequencing said protein. In some embodiments, sequencing said protein comprises: enzymatically cleaving an N-terminal residue of said protein, and binding an affinity binder bearing a detectable label to said protein in situ. In some embodiments, said affinity binder is an N-terminal amino acid binding protein.

In some embodiments, said detectable label are configured to provide signal amplification via cyclic hybridization chain reaction (HCR) or DNA points accumulation for imaging in nanoscale topography (PAINT). In some embodiments, said at least two different types of biomolecules comprise ribonucleic acid (RNA), deoxyribonucleic acid (DNA), proteins, and small molecules. In some embodiments, the method further comprises detecting a molecular interaction amongst the different classes of biomolecules. In some embodiments, detecting different classes of biomolecules within a proximity of one another signals the molecular interaction. In some embodiments, the method further comprises measuring a spatial distance between the two or more different classes of biomolecules. In some embodiments, said detecting comprises detecting presence of a first type of biomolecule via expression of a second type of biomolecule. In some embodiments, the first type of biomolecule comprises a small molecule. In some embodiments, said second type of biomolecule is a nucleic acid. In some embodiments, the nucleic acid is a ribonuclease acid (RNA), wherein the transcript of the RNA is regulated by the small molecule through transcriptional repression or activation. In some embodiments, the abundance or presence of the nucleic acid indicates the abundance or presence of the small molecule.

In some embodiments, said detecting said one or more biomolecules is accomplished using fluorescent in situ sequencing (FISSEQ). In some embodiments, the attachment moieties comprise a reactive group. In some embodiments, the attachment moieties comprise an amine, thiol, azide, alkyne, or a click reactive group. In some embodiments, the attachment moieties comprise a polymerizeable group.

In another aspect, the present disclosure provides a method of detecting a plurality of biomolecules of a biological sample. The method comprises: providing said biological sample comprising a plurality of biomolecules, which plurality of biomolecules comprises a first biomolecule that is indicative of a presence or absence of a second biomolecule of said biological sample; modifying said first biomolecule in situ to comprise an attachment moiety; linking said attachment moiety to a three-dimensional polymer matrix in situ, wherein said attachment moiety is configured to preserve an absolute or relative spatial relationship of said first biomolecule within said biological sample; detecting said first biomolecule; and identifying said presence or absence of said second biomolecule upon detecting said first biomolecule.

In some embodiments, the method further comprises modifying said second biomolecule in situ to comprise an additional attachment moiety, and linking said additional attachment moiety to said three-dimensional polymer matrix in situ, wherein said additional attachment moiety is configured to preserve an absolute or relative spatial relationship of said second biomolecule within said biological sample. In some embodiments, the first type of biomolecule comprises a small molecule. In some embodiments, said small molecule is a metabolite. In some embodiments, the nucleic acid is a ribonuclease acid (RNA), wherein the transcript of the RNA is regulated by the small molecule through transcriptional repression or activation. In some embodiments, the abundance or presence of the nucleic acid indicates the abundance or presence of the small molecule.

In another aspect, the present disclosure provides a method of in situ detection of two or more classes of biomolecules in a single reaction vessel. The method comprises: providing a plurality of biomolecules comprising biomolecules of said two or more classes of biomolecules from a biological sample in said single reaction vessel; forming a polymer matrix in situ with said plurality of biomolecules, wherein said polymer matrix preserves an absolute or relative spatial relationship of said plurality of biomolecules in said biological sample; and detecting at least a subset of said plurality of biomolecules.

In some embodiments, the biomolecules are modified to include an attachment moiety for each biomolecule. In some embodiments, the attachment moiety is capable of linking to the polymer matrix. In some embodiments, the method further comprises providing a primer or probe comprising an attachment moiety, wherein the attachment moiety is capable of linking to the polymer matrix. In some embodiments, the biomolecules include two or more molecules of genomic DNA or fragments thereof, and wherein the attachment moiety is further used to preserve the absolute or relative spatial relationships of the DNA molecules. In some embodiments, a genomic DNA FISSEQ library is formed with the polymer matrix. In some embodiments, the biomolecules include two or more molecules of protein species or fragments thereof, and wherein each of the protein molecules comprises an attachment moiety that is further used to preserve the absolute or relative spatial relationships of the protein molecules. In some embodiments, the method further comprises attaching a DNA barcode to the polymer matrix or incorporating the DNA barcode into the polymer matrix formed in situ. In some embodiments, the biomolecules include small molecules. In some embodiments, each of the small molecules comprises an attachment moiety that is further used to preserve the absolute or relative spatial relationships of the metabolite and small molecules. In some embodiments, two or more molecular probes are used for detection of a molecular interaction in situ, wherein each of the two or more molecular probes comprises a DNA barcode sequence. In some embodiments, said detection further comprises cytological and/or histological staining. In some embodiments, the polymer matrix can be expanded for super-resolution detection for panomic FISSEQ. In some embodiments, said detection further comprises utilizing computational analysis.

In some embodiments, the two or more classes of biomolecules described herein comprise RNA, DNA, protein, lipid, and small molecule.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Overview

Figure 1A:
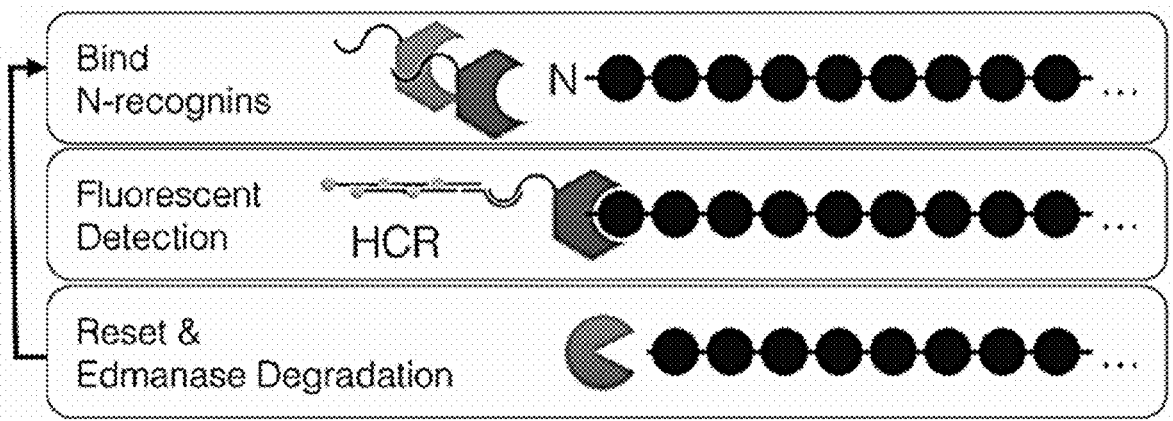
FIGS. 1A-1C depicts a schematic of direct single-protein sequencing, in accordance with embodiments.

The current disclosure provides systems and methods related to processing of a sample so that biomolecules of interest are fixed in a 3-dimensional matrix. As used herein, a 3-dimensional matrix may refer to a hydrogel, or a gel. The 3-dimensional matrix may be polymerized and/or expanded using various stimuli, such as an electromagnetic stimulus, an electrochemical stimulus, or a thermal stimulus. In some embodiments, the 3-dimensional matrix can expand or shrink/contract with an external stimulus such as an electromagnetic stimulus, an electrochemical stimulus, or a thermal stimulus. In some instances, the three-dimensional matrix may be polymerized, and subsequently probes comprising a label may be flown into the matrix for detection of the biomolecules of interest. The sample can be used and/or re-used to detect different classes of biomolecules in situ in a single assay. In some instances, the sample may (the same sample) may be processed or assayed multiple times for detection of different types or classes of biomolecules. One of the advantages of the systems and methods of the present disclosure, for example, is to use a single sample for different biomolecule detections. In some embodiments, the sample is processed by a reagent (e.g. hydrogel forming monomers) so that a hydrogel can be formed in situ. In some embodiments, the biomolecules of interest can be nucleic acids, proteins, and/or small molecules. In various cases, the biomolecules of interest are linked to the hydrogel via an attachment moiety. In various embodiments, the reagents for preparing the hydrogel are provided. In various embodiments, the methods to attach different biomolecules of interest to the hydrogel are provided. In some instances, a container may be provided as a part of the systems described herein. The container may be any container configured to contain biological samples, biomolecules, swelling agents, attachment moieties, reagents, etc. The container may be configured to receive a stimulus from a source of said stimulus in some instances.

RNA & DNA FISSEQ

Fluorescent in situ sequencing (FISSEQ) can refer to a method to detect or sequence 3-dimensionally arranged targets in situ within a matrix, wherein the detection signal is a fluorescent signal. Sequencing methods that can be employed by FISSEQ can be sequencing-by-synthesis, sequencing by ligation, or sequencing by hybridization. The targets detected or sequenced in FISSEQ can be a biomolecule of interest or a probe bound to the biomolecule of interest.

The present disclosure may provide methods or systems for RNA and/or DNA fluorescent in situ sequencing (FISSEQ). Any components utilized for FISSEQ may be a part of the systems described herein. For example, the disclosure may provide a primer comprising an attachment moiety. The attachment moiety may be utilized for FISSEQ. The attachment moiety in some instances may be utilized to link biomolecules of interest to a hydrogel. Optionally, the attachment moieties may comprise a polymerizeable group. In some embodiments, the attachment moiety comprises a free radical polymerizeable group. In some embodiments, the attachment moiety comprises an amine, a thiol, an azide, an alkyne, or a click reactive group. In various embodiments, the attachment moiety may be subsequently linked to a hydrogel. Optionally, the attachment moiety, or moieties may be linked to the hydrogel in situ. In various embodiments, a hydrogel is formed in situ, incorporating the attachment moiety. In various embodiments, the attachment moiety is further used to preserve the absolute or relative spatial relationships among two or more molecules or fragments of genomic DNA within a sample. The method according to the present disclosure may comprise forming a hydrogel in situ, incorporating a primer comprising an attachment moiety. The method according to the present disclosure may further comprise the step of annealing the primer to a target nucleic acid. In some cases, the method according to the disclosure further comprises the step of reverse transcription from the primer. In some other cases, the method according to the disclosure further comprises the step of polymerase chain reaction from the primer. The method according to the disclosure comprises the step of ligation using either 3' or 5' ends of the primer, or using both.

Genome FISSEQ

Next-generation sequencing technologies can be used for resequencing various sources of variation between organisms, e.g., for personalized medicine, as well as for other genome sequencing applications, such as inferring phylogeny, as these may not require information about the spatial organization of the DNA sequence. However, genomic FISSEQ can be used to obtain a number of exceptionally valuable information within a biological sample.

For example, it may not be the case that each somatic cell within an organism has an identical genome sequence. Extensive copy number variation (CNV) can be observed in somatic tissues. See e.g., O'Huallachain, Maeve, et al. "Extensive genetic variation in somatic human tissues." *Proceedings of the National Academy of Sciences* 109.44 (2012): 18018-18023. More than 30 Mendelian diseases can be associated with somatic mosaicism. See e.g., Fabio Candotti. "Somatic mosaicism in primary immune deficiencies." *Current opinion in allergy and clinical immunology* 8.6 (2008): 510-514. Somatic mutations may be a primary initiator of autoimmune disease. See e.g., Ross, Kenneth Andrew. "Coherent somatic mutation in autoimmune disease." *PloS one* 9.7 (2014): e101093. Somatic evolution may in some instances diversify the genome of cancerous cells and also generates spatial and temporal heterogeneity within the organism and within the tumor. See e.g., Schmitt, Michael W., Marc J. Prindle, and Lawrence A. Loeb. "Implications of genetic heterogeneity in cancer." *Annals of the New York Academy of Sciences* 1267.1 (2012): 110-116. Somatic variation among cancer cells may allow rare cells bearing drug-resistant genotypes to cause recurrence after treatment. See e.g., Schmitt, Michael W., Lawrence A. Loeb, and Jesse J. Salk. "The influence of subclonal resistance mutations on targeted cancer therapy." *Nature reviews Clinical oncology* 13.6 (2016): 335-347.

Even in normal immune cells, V(D)J recombination may create diversity in immunoglobulins (Igs) and T-cell receptors (TCRs) that enables the adaptive immune system. See e.g., Market, Eleonora, and F. Nina Papavasiliou. "V(D)J recombination and the evolution of the adaptive immune system." *PLOS Biol* 1.1 (2003): e16. Within microbial populations, such as biofilms, the distinct genomic sequences of the diverse species may be organized spatially. See e.g., Cutler, Nick A., et al. "The spatial organization and microbial community structure of an epilithic biofilm." *FEMS microbiology ecology* 91.3 (2015): fiu027. Moreover, every sufficiently large organism may be composed of a number of ecosystems—the microbiomes, such as gut and skin, which can be populated with the genomes of diverse organisms from all kingdoms of life, either symbiotically or pathogenically. Although certain implementations of DNA next generation sequencing (NGS) have single cell resolution (see e.g., Zong, Chenghang, et al. "Genome-wide detection of single-nucleotide and copy-number variations of a single human cell." Science 338.6114 (2012): 1622-1626; Burton, Joshua N., et al. "Species-Level Deconvolution of Metagenome Assemblies with Hi-C-Based Contact Probability Maps." *G3: Genesl Genomesl Genetics* 4.7 (2014): 1339-1346), the ability to localize the sequence data may remain limited.

Within individual cells, the genome is organized spatially into nucleosomes (see e.g., Lee, William, et al. "A high-resolution atlas of nucleosome occupancy in yeast." *Nature genetics* 39.10 (2007): 1235-1244), into heterochromatin, euchromatin or a growing number of other chromatin states (see e.g., Baker, Monya. "Making sense of chromatin states." *Nature methods* 8.9 (2011): 717-722), by trans-acting sequences such as enhancer-loops (Heidari, Nastaran, et al. "Genome-wide map of regulatory interactions in the human genome." *Genome research* 24.12 (2014): 1905-1917; Rao, Suhas S P, et al. "A 3D map of the human genome at kilobase resolution reveals principles of chromatin looping." *Cell* 159.7 (2014): 1665-1680), into topologically-associated domains (TADs) (Dixon, Jesse R., et al. "Topological domains in mammalian genomes identified by analysis of chromatin interactions." *Nature* 485.7398 (2012): 376-380; Nora, Elphège P., et al. "Spatial partitioning of the regulatory landscape of the X-inactivation centre." *Nature* 485.7398 (2012): 381-385; Sexton, Tom, et al. "Three-dimensional folding and functional organization principles of the Drosophila genome." *Cell* 148.3 (2012): 458-472), and with respect to a wide array of other biomolecules, such as proteins (Jothi, Raja, et al. "Genome-wide identification of in vivo protein-DNA binding sites from ChIP-Seq data." *Nucleic acids research* 36.16 (2008): 5221-5231), and RNA (Chu, Ci, et al. "Genomic maps of long noncoding RNA occupancy reveal principles of RNA-chromatin interactions." *Molecular cell* 44.4 (2011): 667-678). Methods of using NGS to detect chromatin conformation measure the relative contact frequencies, which reflects proximity, of loci both in cis and trans with 0.2~1 kb resolution. See e.g., Dekker, Job, et al. "Capturing chromosome conformation." *science* 295.5558 (2002): 1306-1311; Lieberman-Aiden, Erez, et al. "Comprehensive mapping of long-range interactions reveals folding principles of the human genome." *science* 326.5950 (2009): 289-293. (For a review of chromosome conformation capture technologies, (see Sati, Satish, and Giacomo Cavalli. "Chromosome conformation capture technologies and their impact in understanding genome function." *Chromosoma* (2016): 1-12.) However, these methods may only measure the relative organization of genomic sequences, not the absolute organization, which is also related to activation state (see e.g., Schneider, Robert, and Rudolf Grosschedl. "Dynamics and interplay of nuclear architecture, genome organization, and gene expression." *Genes & development* 21.23 (2007): 3027-3043), nor the shape or size of the loci (see e.g., Beliveau, Brian J., et al. "Single-molecule super-resolution imaging of chromosomes and in situ haplotype visualization using Oligopaint FISH probes." *Nature communications* 6 (2015)). Chromatin conformation capture methods have also traditionally had poor sensitivity, requiring millions of input cells to capture millions of locus-locus co-localization events, i.e., detecting only a few events per cell in order to create a population average conformation. The input amounts can be scaled to single cells, although at the cost of a significant reduction in sensitivity. See e.g., Nagano, Takashi, et al. "Single-cell Hi-C for genome-wide detection of chromatin interactions that occur simultaneously in a single cell." Nature protocols 10.12 (2015): 1986-2003.

Super-resolution imaging of fluorescent in situ hybridization (FISH) can be used to detect sequence-level variation (see e.g., Kallioniemi, Anne, et al. "Gene Copy Number Analysis by Fluorescence in Situ Hybridization and Comparative Genomic Hybridization." *Methods* 9.1 (1996): 113-121) as well as the absolute or relative spatial organization of genomic loci (see e.g., Beliveau, Brian J., et al. "Single-molecule super-resolution imaging of chromosomes and in situ haplotype visualization using Oligopaint FISH probes." *Nature communications* 6 (2015)). FISSEQ may enable direct measurement of the spatial organization of genomic sequences within single cells. Therefore, direct in situ sequencing of the genome can reveal the spatial relationship between sequences with fine resolution, even down to hundreds or tens of bases, and with sensitivity to rare localization events proportional to the number of cells in the assay. Moreover, when combined with information from in situ RNA sequencing or protein detection, single-cell heterogeneity in epigenetic state may be uncovered, and it may be possible to understand the mechanisms underlying the regulation of gene expression.

Epigenetics

Antibodies or other markers can be applied for epigenetic modifications alongside genomic detection, such as by using DNA-conjugated antibodies alongside OligoPaint, OligoFISSEQ, capture by circularization methods, or direct in situ genomic sequencing. Factors for which antibodies are available and that play prominent roles in gene regulation, transcription, replication, and/or DNA damage and repair, include globally acting factors such as cohesins, condensins, RNAPII, CTCF, histone variants (e.g., H2A.Z, H2A.X, H3K4me3, H3K27ac, H3K27me3, H3K9me2/3), components of the PRC1, PRC2, SIN3, NuRD, and co-REST chromatin complexes, as well as factors involved in the establishment of pluripotency, such as Oct4, Sox2, and Nanog. As genome FISSEQ enables visual distinction of homologous chromosomes, we can investigate X-inactivation, imprinting, and monoallelic expression. Importantly, while other homolog-sensitive methods are restricted to repetitive portions of the genome or RNA molecules, and thus are inappropriate for single-copy or silenced regions, the methods provided herein can target single nucleotide polymorphisms (SNPs), enabling genome-wide discovery.

The genome FISSEQ can be a powerful strategy for simultaneously measuring the genotype, epigenetic state, and 3D organization of the genome in single cells. As with RNA FISSEQ, genomic FISSEQ may be inherently limited by the spatial constraint on the number of physically discrete (non-overlapping) and resolvable fluorescent signals that can be measured within a nucleus. This may limit the number of loci that can be detected at any one time, and also the detection of spatially co-localized sequences (e.g., enhancer loops). However, many applications, such as targeted genome FISSEQ or ensemble genomic resequencing using a large number of cells, can operate within this spatial constraint. For example, each nucleosome, corresponding to approximately 150 base pairs of sequence, is roughly $10 \times 10 \times 20$ nanometers in size, may be resolvable by ExM using a linear expansion factor of only 8~10×, or other techniques known to a skilled artisan in the field of super-resolution microscopy techniques.

Overall, as with RNA FISSEQ, the accessibility of the nucleic acid to library construction biochemistry may actually encode additional information into the library. In this way, FISSEQ can provide information not only on the spatial organization and sequence variation of the genome, but also insights into the epigenetic state. Epigenetic features, such as chromatin state, can reveal mechanisms of genome regulation and be used to distinguish between cellular phenotypic states ("cell types"). Genomic FISSEQ may be combined with RNA FISSEQ and FISSEQ detection of proteins and other biomolecules, which may empower correlative analysis to fundamentally reveal the mechanisms of genome regulation.

To perform genomic FISSEQ, genomic DNA can be linked to a hydrogel matrix and processed in situ for FISSEQ detection. Various genomic information can be determined using the hydrogel treated biological sample. In various embodiments, genomic DNA can be linked to the hydrogel matrix by an attachment moiety, e.g., as described herein. The attachment moiety can be reacted with a reactive group on the hydrogel through conjugation chemistry. In some embodiments, the attachment moiety can be linked to target of interest through conjugation chemistry. In some embodiments, the attachment moiety can be directly linked to a functional group (or reactive group) on the native nucleic acid molecule. In some embodiments, the attachment moiety can be indirectly linked to a target through an intermediate chemical or group. The conjugation strategies described herein are not limited to nucleic acid targets and can be used for protein or small molecule targets as well.

As used herein, the term "reactive group" means any moiety on the monomer or polymer of the hydrogel that is capable of reacting chemically with a functional group (or another reactive group, or an attachment moiety) on a different compound (i.e., the substrate of interest or the target) to form a covalent or ionic linkage. Reactive group and functional group as used herein may be used interchangeably. Attachment moiety used herein can comprise a reaction group. Examples of suitable reactive groups include electrophiles or nucleophiles that can form a covalent linkage by reaction with a corresponding nucleophile or electrophile, respectively, on the substrate of interest. Non-limiting examples of suitable electrophilic reactive groups may include, for example, esters including activated esters (such as, for example, succinimidyl esters), amides, acrylamides, acyl azides, acyl halides, acyl nitriles, aldehydes, ketones, alkyl halides, alkyl sulfonates, anhydrides, aryl halides, aziridines, boronates, carbodiimides, diazoalkanes, epoxides, haloacetamides, haloplatinates, halotriazines, imido esters, isocyanates, isothiocyanates, maleimides, phosphoramidites, silyl halides, sulfonate esters, sulfonyl halides, and the like. Non-limiting examples of suitable nucleophilic reactive groups may include, for example, amines, anilines, thiols, alcohols, phenols, hyrazines, hydroxylamines, carboxylic acids, glycols, heterocycles, and the like.

The disclosure provides a method of modifying genomic DNA in situ to comprise an attachment moiety. In some embodiments, the attachment moiety comprises a polymerizeable group. In some embodiments, the attachment moiety comprises a free radical polymerizeable group. In some embodiments, the attachment moiety comprises an amine, a thiol, an azide, an alkyne, or a click reactive group. In some embodiments, the attachment moiety is subsequently linked to a hydrogel in situ. In various embodiments, a hydrogel is formed in situ, incorporating the attachment moiety. In some embodiments, the attachment moiety is further used to preserve the absolute or relative spatial relationships among two or more molecules or fragments of genomic DNA within a sample.

The disclosure provides a method of further modifying genomic DNA in situ comprising the steps of, fragmenting the DNA, denaturing duplex DNA to form single-stranded DNA strand, modifying 3' and/or 5' ends of the DNA, adding an adapter sequence, circularizing the genomic DNA and amplifying the genomic DNA. In some embodiments, the amplification can be achieved by polymerase chain reaction (PCR) or rolling circle amplification (RCA).

The disclosure provides a method of further detecting all or part of the genomic DNA sequence in situ using nucleic acid sequencing. Exemplary sequencing methods can include sequencing by hybridization and sequencing by synthesizing a complementary strand using a polymerase or ligase (sequencing by synthesis, sequencing by ligation). In some embodiments, fluorescent signals are generated during sequencing.

The disclosure provides use of in situ genomic sequencing for detection of: mutations, including SNV, deletions, insertions, rearrangements, inversions, duplications, chromosomal fusions, and/or other genomic variation for diagnostic, prognostic, or therapeutic guidance in human diseases. Exemplary diseases include, but are not limited to cancer, immune and autoimmune diseases, and Mendelian diseases. The methods provided herein can also be used for detection of sequences relevant to acquired or innate immunity, including the products of V(D)J recombination, immunoglobulins, and immune cell receptors, e.g. T-cell receptors (TCR). In some embodiments, the methods provided herein can be used for detection of non-human genetic sequence within a human patient, including: species within a microbiome, such as skin, gut, oral, and vaginal microbiomes, and pathogens, including bacteria, fungi, and viruses. In some embodiments, the methods provided herein can be used to determine species of a biofilm. In some embodiments, the methods provided herein can be used to determine DNA elements, including transcribed genetic loci, protein coding region, non-protein coding region, enhancers, promoters, regulatory regions, topologically-associated domains (TADs), centromeres, telomeres and origins of replication. In some embodiments, the methods provided herein can be used to detect the spatial relationship among two or more such DNA elements and to detect the properties of DNA elements, including size, shape and volume.

The disclosure provides a kit or a system for forming a genomic DNA FISSEQ library, containing, a reagent comprising a DNA binding moiety and an attachment moiety, wherein the attachment moiety can be linked to a hydrogel; reagents for forming a hydrogel in situ; and/or a DNA oligonucleotide comprising an adapter sequence served as a priming site for further amplification.

The disclosure provides a kit or a system for fluorescent in situ sequencing of DNA, containing, more than one species of oligonucleotide conjugated to a fluorescent moiety; a DNA ligase; an imaging buffer suitable for FISSEQ assay; and/or an incorporation buffer suitable for sequencing.

The disclosure provides a kit or a system for fluorescent in situ sequencing of DNA, containing, more than one species of oligonucleotide conjugated to a fluorescent moiety; a DNA polymerase; an imaging buffer suitable for FISSEQ assay; and/or an incorporation buffer suitable for sequencing.

The disclosure provides a kit or a system for fluorescent in situ sequencing of DNA, containing, more than one species of metastable self-assembling DNA hairpins, e.g., hybridization chain reaction monomers, conjugated to a fluorescent moiety; more than one species of DNA oligonucleotides comprising sequences complementary to genomic sequence; an imaging buffer suitable for FISSEQ assay; a hybridization buffer suitable for nucleic acid hybridization; and/or an HCR amplification buffer.

Protein FISSEQ

Limitations of Traditional Protein Detection Assays

Like nucleic acid targets, proteins can be detected in situ. Various methods can be used to target proteins. For example, in situ protein detection can use the affinity binding properties of immunoproteins and aptamers.

Immunofluorescence techniques exploit the ability of antibodies (Ab), immunoglobulin (Ig) isoforms, or fragments thereof, to bind specifically to a target antigen. Antibodies used for in situ labeling are typically IgG or IgY isotypes, which are composed of four polypeptide chains. Fragments of the antibody (see e.g., Holliger, Philipp, and Peter J. Hudson. "Engineered antibody fragments and the rise of single domains." *Nature biotechnology* 23.9 (2005): 1126-1136), such as the "fragment antigen-binding" (Fab), or even single chains, referred to as nanobodies (see e.g., Gibbs, W. Wayt. "Nanobodies." *Scientific American* 293.2 (2005): 78-83) can be used to bind protein target as well.

Proteins are typically detected either by direct labeling of the antibody with a fluorescent dye, or by secondary labeling of the bound antibody using a fluorescent secondary antibody, which recognizes the constant region of the primary antibody. Use of secondary labeling can also be a form of signal amplification, as a number of secondary antibodies can bind to different domains of the primary antibody, and secondary antibodies can convey a number of fluorescent moieties. However, use of a secondary antibody may limit the multiplexity to the number of orthogonal primary-secondary antibody pairs, e.g., using Ig proteins from different species, or different Ig isotypes or subtype. See e.g., Tidman, N., et al. "Delineation of human thymocyte differentiation pathways utilizing double-staining techniques with monoclonal antibodies." *Clinical and experimental immunology* 45.3 (1981): 457. Antibody staining can also be done serially, although this only scales the multiplexity linearly with the number of cycles. See e.g., Lan, Hui Y., et al. "A novel, simple, reliable, and sensitive method for multiple immunoenzyme staining: use of microwave oven heating to block antibody crossreactivity and retrieve antigens." *Journal of Histochemistry & Cytochemistry* 43.1 (1995): 97-102; Gerdes, Michael J., et al. "Highly multiplexed single-cell analysis of formalin-fixed, paraffin-embedded cancer tissue." *Proceedings of the National Academy of Sciences* 110.29 (2013): 11982-11987. Antibodies can be multiplexed by serial sectioning, where immunofluorescent detection can be performed on individual sections which are then computationally combined. See e.g., Potts, Steven, et al. "Methods for feature analysis on consecutive tissue sections." U.S. Pat. No. 8,787,651. 22 Jul. 2014.

Using either primary or secondary labeling, in situ protein detection can be multiplexed to a limited extent. Using brightfield microscopy, chromogenic deposition can provide a number of visually distinct chromogens/enzyme pairs (van der Loos, Chris M. "Chromogens in multiple immunohistochemical staining used for visual assessment and spectral imaging: the colorful future." *Journal of Histotechnology* 33.1 (2010): 31-40). "Colorimetric" barcoding can also be used. See e.g., Stack, Edward C., et al. "Multiplexed immunohistochemistry, imaging, and quantitation: a review, with an assessment of Tyramide signal amplification, multispectral imaging and multiplex analysis." *Methods* 70.1 (2014): 46-58. Both of these techniques are limited by the co-localization of target proteins, which conflate the distinct colors required for identification. Multispectral imaging, using quantum dots, can be used to simultaneously image seven fluorescent signals (see e.g., Fountaine, Thomas J., et al. "Multispectral imaging of clinically relevant cellular targets in tonsil and lymphoid tissue using semiconductor quantum dots." *Modern Pathology* 19.9 (2006): 1181-1191).

Even using primary labeling, which can avoid the problem of secondary antibody specificity, it may be challenging to combine many antibodies together in a single assay. Antibodies typically require idiosyncratic sample treatment, referred to as antigen retrieval (AR). Common forms of AR can include high and low pH, high temperatures, or enzymatic treatments (see e.g., Taylor, Clive R. "Quantitative in situ proteomics; a proposed pathway for quantification of immunohistochemistry at the light-microscopic level." *Cell and tissue research* 360.1 (2015): 109-120). Unfortunately, these treatments can be difficult to combine or mutually exclusive, significantly limiting the composition of sets of antibodies that can be used simultaneously. Many AR treatments may be damaging to the other biomolecules of interest, such as RNA and DNA. For example, the depurination rate of DNA can increase with heat and under acidic conditions. Proteins from a single tissue section can be separated by size using layered membranes, enabling immunofluorescent detection of proteins of different sizes under different conditions and re-using fluorescent colors or secondary antibodies. See e.g., Park, Soon Sik, et al. "Multiplex layered immunohistochemistry to predict response of HER2-positive breast cancer patients to trastuzumab therapy." *ASCO Annual Meeting Proceedings*. Vol. 30. No. 27 suppl. 2012. Although this method can extend the multiplexity of immunofluorescence detection, it can only capture the 2D distribution of proteins within the sample, due to the reallocation of the third dimension to separation of proteins by size.

In addition to immunoproteins, protein detection in situ can be enabled by aptamers, which are oligonucleotides or peptides that can bind a specific target. See e.g., Ellington, Andrew D., and Jack W. Szostak. "In vitro selection of RNA molecules that bind specific ligands." *nature* 346.6287 (1990): 818-822; Tuerk, Craig, and Larry Gold. "Systematic evolution of ligands by exponential enrichment: RNA ligands to bacteriophage T4 DNA polymerase." *Science* 249.4968 (1990): 505-510. Despite some successful uses, aptamers may not be widely used for in situ protein detection due to both the wider availability of antibody reagents and the more favorable properties of antibody binding. Aptamers usually bind to the proteins less well than antibodies which can bind roughly 10~100-fold better than aptamers in many cases, and work consistently under a variety of conditions. Antibodies work better than aptamers may be because proteins have a larger chemical space available to exploit for improved affinity, such as the sulfur atom of Cysteine, hydrophobic interactions, and positive charged groups. However, aptamers may still be valuable in targeting proteins in some cases. Recent advances using chemically-modified nucleotides and use of a kinetic challenge to select for slow off-rates can produce aptamers with affinities matching antibodies (nM~pM). See e.g., Gold, Larry, et al. "Aptamer-based multiplexed proteomic technology for biomarker discovery." *PloS one* 5.12 (2010): e15004.

Using either immunoproteins or aptamers, protocols for protein labeling in situ typically may need extensive validation and fine-tuning to achieve accurate results. The complexity of these protocols may arise from the large diversity of biomolecular and macromolecular components and their modifications during sample fixation and processing. Moreover, neither immunoproteins nor aptamers may be used for detection of single molecules due to the limited signal amplification and high background.

Finally, a last class of protein affinity binding reagents include non-immunological peptides and proteins which have natural affinity for certain proteins. One example is wheat germ agglutinin, a 38 kDa lectin, or carbohydrate-binding protein, which can be used to label cell membranes and other tissue features such as cartilage. Another example is phalloidin, a bicyclic heptapeptide toxin that binds F-actin and is used to label cytoskeleton. The examples herein are not limiting.

Library-On-Library Selection of Affinity Binding Reagents for FISSEQ

In some embodiments, provided herein are methods of using library-on-library selection of affinity binding agents to be used for FISSEQ. In some embodiments, the library-on-library selection strategy may be to use single-molecular-interaction sequencing (SMI-seq). The strategy can be useful in selecting multiple binding agents for multiple protein targets that can work in the same buffer condition. In some embodiments, the binding agents selected in the methods provided herein can work in the same condition and do not interact with other. In some embodiments, the binding agents may have reduced reactivity with each other. The methods provided herein use the selected binding agent to detect proteins in 3-dimensionally fixed sample using FISSEQ.

Despite the limitations of these affinity binding reagents, there are methods for "library screening" of binders to simultaneously measure molecular binding affinity and specificity. For example, single-molecular-interaction sequencing (SMI-seq) uses FISSEQ in acrylamide to detect single-molecule interactions between a library of protein-ribosome-messenger-RNA-complementary-DNA (PRMC) complexes and a set of DNA-conjugated proteins. See e.g., Gu, Liangcai, et al. "Multiplex single-molecule interaction profiling of DNA-barcoded proteins." *Nature* 515.7528 (2014): 554-557. SMI-seq can enable screening and evolution of affinity binders, as from a library of scFv peptides. In the same way, in vitro selection of aptamers, called SELEX, can be used for screening and evolution of aptamers. See e.g., Blind, Michael, and Michael Blank. "Aptamer selection technology and recent advances." *Molecular Therapy—Nucleic Acids* 4.1 (2015): e223. Both of these methods enable rounds of selection from a large library of affinity binders (e.g., 1010) with diversification (e.g., by error-prone PCR), followed by DNA sequencing to determine the binding frequency and specificity, to characterize binders against a target analyte.

In order to enable discovery of affinity binders against a large number of target molecules, however, a library of binders needs to be screened against a library of targets, a technique known as "library-on-library". In some cases, SMI-seq can use DNA conjugation to barcode the target proteins. In some other cases, SMI-seq may use mRNA display to protein-ribosome-messenger-RNA-complementary-DNA (PRMC) complexes on both sides of the selection, as with an scFv library and a target library comprising the human ORFcome (ORFcome Collaboration. "The ORFcome Collaboration: a genome-scale human ORF-clone resource." Nature methods 13.3 (2016): 191-192). In the case of using mRNA display, a phage-scFv library specifically designed for diversity (via lox scrambling of heavy and light chain domains) and robust folding (a previously vexing failure mode) can be used. The estimated diversity of this strategy can be approximately 5e7 before recombination (~2.5e14 after).

Simultaneous selection of a library of PRMC binders, having known binding strength and specificity, can be useful for detection of proteins by FISSEQ. This method can allow us to avoid cross-reactivity and guarantee compatible binding conditions for our entire library. Since target peptides are translated, one can control the state of the target peptide to simulate or match the state of the proteins in the FISSEQ sample. For example, during FISSEQ formaldehyde fixation may be used and followed by treatment in urea or SDS to denature proteins. One can also prepare a barcoded ORFeome library using the same chemical treatments to match the epitope presentation of the biological sample.

In some cases, SMI-seq using aptamers to target our ORFeome target library of protein-ribosome-messenger-RNA-complementary-DNA (PRMC) can also be used for high-throughput selection of aptamers. Novel SELEX techniques may be developed using our barcoded target library. Although these approaches may solve the problems related to discovery and compatibility of a library of affinity binders, they may not solve the problems associated with detection of single molecules. Single molecule detection can be further developed based on two strategies. For example, one strategy may be to develop signal amplification methods, such as RCA and Cyclic HCR (CHCR), for detecting single binders, and the other may be to develop super-resolution microscopy methods, such as ExM, for resolving and localizing the single target proteins.

Direct Single-Protein Sequencing

In some embodiments, the methods provided herein further comprise identifying the protein sequence. In some embodiments, the protein sequence may be identified through Edman degration.

Peptide sequencing using the Edman degradation reaction may be a method of determining the ordered amino acid composition of a protein by cycles of specific cleavage and identification of the N-terminal residue. The N-terminal amino group may be reacted with phenyl issothiocyanite under mildly alkaline conditions, forming a cyclical phenyl-thiocarbamoyl derivative. By shifting the condition to acidic, this derivative may be cleaved, extracted into organic solvent, stabilized into the phenylthiohydantoin (PTH)-amino acid derivative, and identified using chromatography or electrophoresis. This process can be adapted to single-molecule protein sequencing in situ. Instead of using the Edman degradation reaction, which may not be compatible with DNA stability, enzymatic cleavage of the N-terminal residue can be used. See e.g., Borgo, Benjamin, and James J. Havranek. "Computer-aided design of a catalyst for Edman degradation utilizing substrate-assisted catalysis." *Protein Science* 24.4 (2015): 571-579. Rather than using chromatography or electrophoresis for detection of the cleaved N-terminal residue, an affinity binder, such as an N-terminal amino acid binding protein (NAAB) bearing a detectable label, can be used. For single-molecule detection, ideal detectable labels are those that afford signal amplification, such as by Cyclic HCR (CHCR) or DNA PAINT.

DNA PAINT can also enable super-resolution microscopy, which can be used to detect single N-termini among the crowded cellular environment. Other strategies can also be used to avoid convolution of diffraction-limited sequencing signals from multiple proteins. ExM with sufficiently large expansion factors can achieve physical separation of individual proteins beyond the diffraction limit. Similar to stochastic forms of super-resolution microscopy and digital partition microscopy, one can limit the sequencing reaction to random or targeted subsets of proteins, such as by covalently linking only a subset of proteins into the FISSEQ hydrogel, or as by proteolysis until only a fraction of the original proteins remain.

Figure 1B:
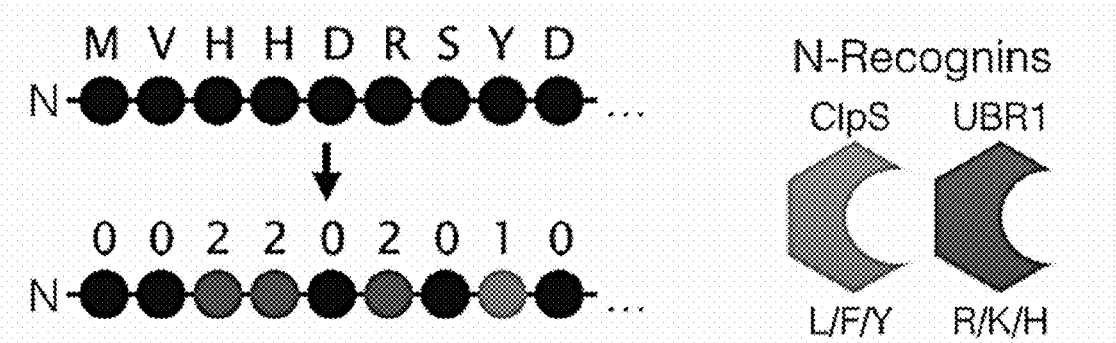
Figure 1C:
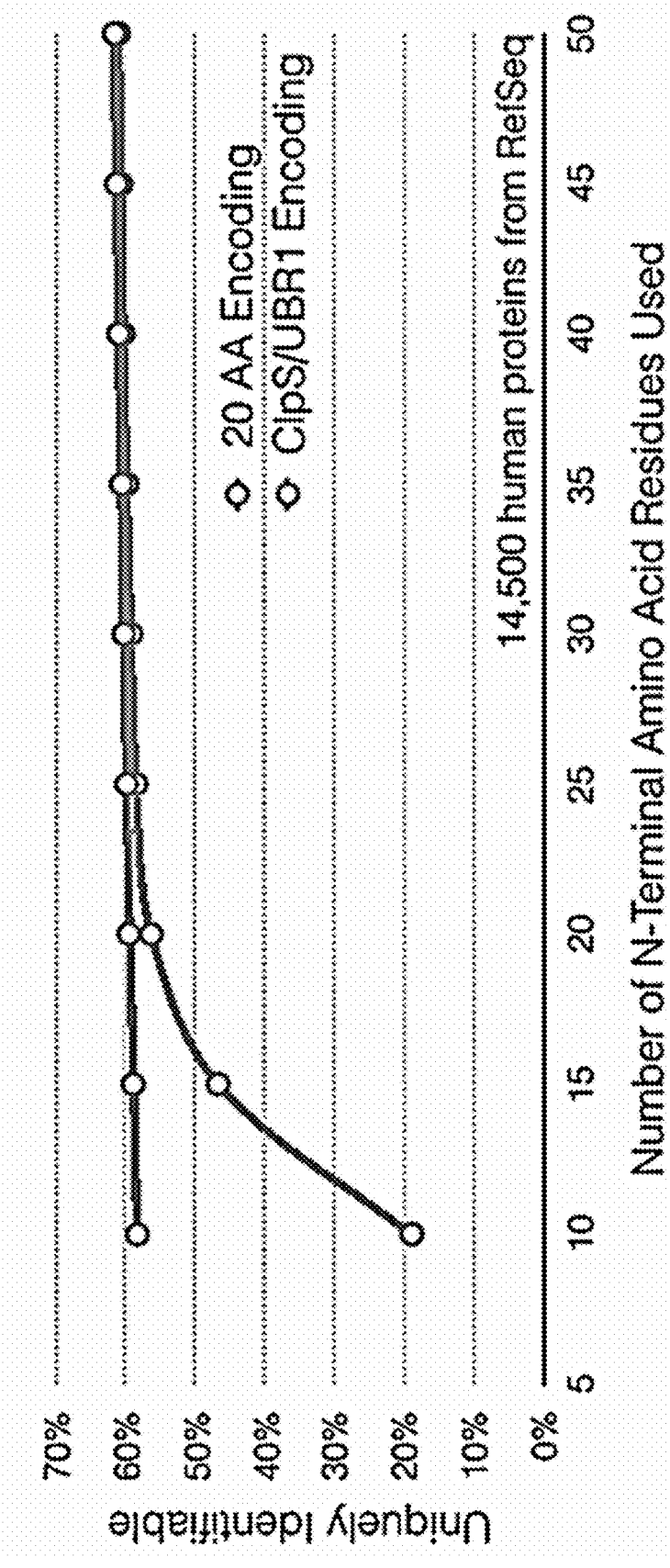

Other protein fingerprinting methods may enable identification without determining the ordered amino acid composition of the protein. For example, only using Clps and/or UBR1, which bind to L/F/Y and R/K/H, respectively, the number of uniquely identifiable proteins approaches the number using recognition of all 20 amino acids after determination of only 25 residues (FIGS. 1A-1C). See e.g., Erbse, A., et al. "ClpS is an essential component of the N-end rule pathway in *Escherichia coli.*" *Nature* 439.7077 (2006): 753-756; Varshavsky, Alexander. "The N-end rule: functions, mysteries, uses." *Proceedings of the National Academy of Sciences* 93.22 (1996): 12142-12149. More "colorimetric" approaches to protein identification can be developed (i.e., using the combination of signals rather than the ordered permutation). Exemplary colorimetric approach can be selectively hydrolyzing the peptide bonds between certain pairs of amino acids and counting the number of termini created.

The current disclosure provides methods of library-on-library screening for direct single-protein sequencing, by eliminating the need for nucleic-acid barcodes. In situ sequencing of single proteins also enables the selection of affinity binders directly on biological specimens, entirely avoiding the need for a synthetic target library. Measuring the abundance of mRNA alone gives limited insights into the state of the proteome. Massively multiplex detection of single proteins inside intact biological specimens can lead to a new era of quantitative proteomics. The protein FISSEQ provided herein can also be combined with RNA and DNA FISSEQ.

The present disclosure provides a method of modifying a protein in situ to comprise an attachment moiety. In some embodiments, the attachment moiety comprises a free radical polymerizeable group. In some embodiments, the attachment moiety comprises a polymerizeable group. In some embodiments, the attachment moiety comprises an amine, a thiol, an azide, an alkyne, a click reactive group. In some embodiments, the attachment moiety is subsequently linked to a hydrogel in situ. In some embodiments, a hydrogel is formed in situ, incorporating the attachment moiety. In some embodiments, the attachment moiety is further used to preserve the absolute or relative spatial relationships among two or more molecules or fragments of protein within a sample. The attachment moiety can be linked to protein target through conjugation chemistry. In some embodiments, the attached moiety is linked to native proteins without any intermediate chemicals or groups. In some embodiments, the attachment moiety is linked to a protein target through an intermediate chemicals or groups.

The disclosure provides a method of detecting two or more protein species within a hydrogel comprising binding two or more affinity binding reagents each comprising a moiety conferring affinity binding and also a unique DNA barcode. In some embodiments, the method further comprises detecting the DNA barcode in situ using nucleic acid sequencing. Exemplary sequencing methods include sequencing by hybridization and sequencing by synthesizing a complementary strand using a polymerase or ligase (e.g. sequencing by synthesis, sequencing by ligation). In some embodiments, the method comprises sequencing the DNA barcode, wherein fluorescent signals are generated.

The disclosure provides a method of detecting two or more protein species within a hydrogel comprising binding two or more affinity binding reagents each comprising a unique DNA barcode as well as an attachment moiety comprising a polymerizable group or a click reactive group. In some embodiments, the method further comprises attaching the DNA barcode to a hydrogel or incorporating the DNA barcode into a hydrogel formed in situ. In some embodiments, the method further comprises detecting the DNA barcode in situ using nucleic acid sequencing, such as by hybridization or by synthesizing a complementary strand using a polymerase or ligase (e.g. sequencing by synthesis, sequencing by ligation). In some embodiments, the method comprises a sequencing step, wherein fluorescent signals are generated.

The disclosure provides a method of library-on-library selection of affinity binding reagents to produce affinity binding reagents for FISSEQ, wherein a library of affinity binders comprises two or more binders. In some embodiments, the binders are aptamers. In some embodiments, the binders are comprised of nucleic acids, nucleic acid analogs, peptides, polypeptides, or proteins. In some embodiments, a target library comprises two or more target molecules, comprising nucleic acid, polypeptide, lipid, or small molecules. In some embodiments, each affinity binder and target within each library comprises an additional nucleic acid barcode.

The disclosure provides a method of in situ protein sequencing comprising immobilizing a protein within a hydrogel. In some embodiments, the method further comprises contacting a protein with an N-terminal or C-terminal binder. In some embodiments, the method further comprises detecting a fluorescent label associated with the binder. In some embodiments, the method further comprises contacting the protein with a reagent to cleave one or more N-terminal or C-terminal residues.

The disclosure provides use of in situ protein FISSEQ for detection of proteins and protein modifications for diagnostic, prognostic, or therapeutic guidance in human diseases. Exemplary diseases include, but are not limited to, cancer, immune and autoimmune diseases, neurological and brain diseases, inflammatory disease, cardiac disease (including disease of the heart and circulatory systems), disease of organs (including lung, liver, kidney, gut, bone, connective tissue, and skin), and Mendelian diseases. The disclosure provides use of in situ protein FISSEQ for detection of non-human proteins within a human patient, including: microbial proteins within a microbiome, such as skin, gut, oral, and vaginal microbiomes, and pathogenic proteins, including bacteria, fungi, and viruses. The disclosure provides use of in situ protein FISSEQ for detection of one or more proteins for the purpose of identifying cytological features, including; membranes, lyposome, endosome, mitochondria, golgi apparatus, nucleus, organelles, cytoskeleton, and granules including stress granules. The examples provided herein are not limiting.

The disclosure provides use of in situ protein FISSEQ for detection of one or more proteins for the purpose of identifying histological features, including: cell membranes, nuclei, stroma, epithelia, adipose, extracellular matrix, nerve fibers, blood cells, immune cells, and basement membrane. The examples provided herein are not limiting.

The disclosure provides use of in situ protein FISSEQ for detection of the spatial relationship among two or more protein species. The disclosure provides use of in situ protein FISSEQ for detection of the spatial relationship among two or more cytological or histological features. The disclosure provides use of in situ protein FISSEQ for detection of the properties of cytological or histological elements, including size, shape and volume.

The disclosure provides a kit or a system for forming a protein FISSEQ library comprising reagents for forming a hydrogel in situ. In some embodiments, the kit comprises a library of affinity binders, wherein each unique binder comprises a moiety conferring affinity binding and also a unique DNA barcode. In some embodiments, the kit comprises a buffer for binding the affinity binders. The disclosure provides a kit or a system for fluorescent in situ sequencing of a protein FISSEQ library comprising more than one species of oligonucleotide conjugated to a fluorescent moiety. In some embodiments, the kid comprises a DNA ligase. In some embodiments, the kit comprises an imaging buffer. In some embodiments, the kit comprises an incorporation buffer.

The disclosure provides a kit or a system for fluorescent in situ sequencing of a protein FISSEQ library comprising more than one species of dNTP analog conjugated to a fluorescent moiety. In some embodiments, the kit further comprises a DNA polymerase. In some embodiments, the kit further comprises an imaging buffer. In some embodiments, the kit comprises an incorporation buffer.

The disclosure provides a kit or a system for fluorescent in situ sequencing of a protein FISSEQ library comprising more than one species of metastable self-assembling DNA hairpins, e.g., hybridization chain reaction monomers, conjugated to a fluorescent moiety. In some embodiments, the kit comprises more than one species of DNA oligonucleotides comprising sequences complementary to affinity binder barcode sequence. In some embodiments, the kit comprises an imaging buffer. In some embodiments, the kit comprises a hybridization buffer. In some embodiments, the kit comprises an HCR amplification buffer.

Metabolite and Small Molecule Detection

In order to create a truly pan-omic in situ molecular detection technology, other classes of biomolecules in addition to nucleic acids and proteins can be targeted in the methods provided herein. Some traditional small molecule detection methods can be combined with FISSEQ provided herein. Metabolites are essentially any small molecules that interact with cellular biochemical processes, include vitamins, amino acids, nucleotides, organic acids, alcohols and polyols, lipids and fatty acids, etc. (Wishart, David S., et al. "HMDB: the human metabolome database." *Nucleic acids research* 35.suppl 1 (2007): D521-D526). Beyond their role as intermediates, products, and cofactors in metabolism, metabolites and other small molecules can play a role in biological systems as energy sources, signaling molecules, osmotic regulators, and enzyme inhibitors or activators. Metabolites also serve important functions at the scale of tissue, whole organism, populations, and ecology, as toxins, pigments, odorants, pheromones, etc. (Vining, Leo C. "Functions of secondary metabolites." *Annual Reviews in Microbiology* 44.1 (1990): 395-427). One particularly important class of metabolic products are lipids. The number of lipid species is roughly the same as the number of protein species, and lipids play diverse roles as structural and signaling molecules (Muro, Elconora, G. Ekin Atilla-Gokcumen, and Ulrike S. Eggert. "Lipids in cell biology: how can we understand them better?." *Molecular biology of the cell* 25.12 (2014): 1819-1823). All these small molecules can have complex spatial patterns of organization in a cell.

Metabolites are retained and transported by proteins (Mercer, Andrew C., and Michael D. Burkart. "The ubiquitous carrier protein—a window to metabolite biosynthesis." *Natural product reports* 24.4 (2007): 750-773). Metabolism itself can be highly spatially localized. For example, many metabolic processes can be localized to certain cell types; in fact, metabolic specialization may be a primary fitness driver for the evolution of multicellularity (Ispolatov, Jaroslav, Martin Ackermann, and Michael Docbeli. "Division of labour and the evolution of multicellularity." *Proceedings of the Royal Society of London B: Biological Sciences* (2011): rspb20111999).

Within cells, metabolism can be organized in to macro-compartments such as organelles, and micro compartments, on the order of the size of the metabolites themselves (Saks, Valdur, Nathalie Beraud, and Theo Wallimann. "Metabolic compartmentation—a system level property of muscle cells." *International journal of molecular sciences* 9.5 (2008): 751-767), to improve the efficiency of enzymes (Bonacci, Walter, et al. "Modularity of a carbon-fixing protein organelle." *Proceedings of the National Academy of Sciences* 109.2 (2012): 478-483), prevent cross-talk (Houslay, Miles D. "Compartmentalization of cyclic AMP phosphodiesterases, signalling 'crosstalk', desensitization and the phosphorylation of G i-2 add cell specific personalization to the control of the levels of the second messenger cyclic AMP." *Advances in enzyme regulation* 35 (1995): 303-338), and regulate flux (Klitgord, Niels, and Daniel Segrè. "The importance of compartmentalization in metabolic flux models: yeast as an ecosystem of organelles." *Genome Inform.* Vol. 22. 2010). Membranes are highly organized into "rafts" to compartmentalize signaling, biosynthetic, and endo- and exocytic pathways (see e.g., Simons, Kai, and Julio L. Sampaio. "Membrane organization and lipid rafts." *Cold Spring Harbor perspectives in biology* 3.10 (2011): a004697). Yet detection of these molecules in situ can be limited to use of fluorescent labeling, tracers, and mass spectrometry imaging (e.g., nanostructure-initiator mass spectrometry (NIMS) (Northen, Trent, Gary Siuzdak, and Anders Nordstrom. "Nanostructure-initiator mass spectrometry." U.S. patent application Ser. No. 11/852, 863).

Even low-multiplexity read-outs, such as using fluorescently labeled analogs or by staining (e.g., the Oil-Red-O stain for quantitation of triglyceride (O'Rourke, Eyleen J., et al. "*C. elegans* major fats are stored in vesicles distinct from lysosome-related organelles." *Cell metabolism* 10.5 (2009): 430-435)), can be useful for understanding certain metabolic pathways, inferring overall metabolic flux, and understanding the genetic basis of metabolic disease. Another low-multiplexity read-out that can be combined with FISSEQ may be calcium imaging, allowing us to acquire dynamic measurements of cellular activity, such as neuron firing, which can subsequently be combined with measurement of gene expression, genotype, or even neuronal connectivity. See e.g., Grienberger, Christine, and Arthur Konnerth. "Imaging calcium in neurons." *Neuron* 73.5 (2012): 862-885. Inorganic ions can be central to osmotic regulation, signaling, and cell-electrical activity, but given their size, solubility, and dynamics, they probably need to be quantified in vivo.

All these metabolites may be challenging to assay in situ, as their small size and solubility causes them to be easily washed from the sample during initial fixation. In addition, FISSEQ requires permeabilization to access intracellular molecules, many forms of which actually specifically remove small molecules and lipids. However, a higher multiplexity read-out mechanism for metabolites and biomolecules can be employed. As with protein detection by FISSEQ, a library of DNA-barcoded affinity binding reagents specific to metabolites can be generated (see the discussion of SMI-seq above). Another solution may be to develop dynamic small-molecule biosensors, which can undergo conformational changes in the presence of the target ligand. See e.g., Feng, Justin, et al. "A general strategy to construct small molecule biosensors in eukaryotes." *Elife* 4 (2015): e10606. Biosensors as used herein may refer to genetically encoded biosensors that modulate gene expression in response to the presence of a small molecule inducer. Biosensors may be a part of small molecule inducible systems comprising genetically encoded biosensors. Such biosensor system can transfer the activity or abundance of small molecules into the transcription level of certain RNA species through transcriptional repression or activation. For example, the biosensors can be proteins, wherein the proteins function as transcriptional repressors or activators. In some cases, the transcription repressors or activators can be regulated by small molecules, which in turn regulate RNA transcription. In such cases, the abundance and/or presence of certain RNA transcripts/species can be used to determine the level and/or presence of regulatory small molecules.

In order to retain the metabolites in situ for detection, chemistries to cross link small molecules to an expanding hydrogel matrix need to be developed, which enables permeabilization of the sample by dilution of the biomolecules during expansion. Moreover, as with calcium imaging. FISSEQ experiments that blur the line between in situ and in vivo can be designed. For example, fluorescent biosensors can be used to measure the dynamics of metabolite abundance and localization in vivo, which can be combined with a single time point measurement of gene expression or genotype in situ. Biosensors can also record the abundance and localization of small molecules into RNA, as by activating transcription upon binding, or by directly encoding this information into the genome, such as by using CRISPR/Cas9 genome editing technology. See e.g., Feng, Justin, et al. "A general strategy to construct small molecule biosensors in eukaryotes." *Elife* 4 (2015): e10606; Shipman, Seth L., et al. "Molecular recordings by directed CRISPR spacer acquisition." Science (2016): aaf1175. In the former case, the RNA molecules containing the information about the metabolite concentration in vivo may be detected in situ using FISSEQ. In the latter case, the modified genome sequence may be detected in situ using FISSEQ.

To summarize the metabolite and small molecule combination detection, the disclosure provides a method of modifying a molecule in situ to comprise an attachment moiety. In some embodiments, the attachment moiety comprises a free radical polymerizeable group. In some embodiments, the attachment moiety comprises a polymerizeable group. In some embodiments, the attachment moiety comprises an amine, a thiol, an azide, an alkyne, or a click reactive group. In some embodiments, the attachment moiety is subsequently linked to a hydrogel in situ. In some embodiments, a hydrogel is formed in situ, incorporating the attachment moiety. In some embodiment, the attachment moiety is further used to preserve the absolute or relative spatial relationships among two or more metabolites or small molecules within a sample.

The disclosure provides a method of detecting two or more biomolecular species within a hydrogel comprising binding two or more affinity binding reagents each comprising a moiety conferring affinity binding and also a unique DNA barcode. In some embodiments, the method further comprises detecting the DNA barcode in situ using nucleic acid sequencing, such as by hybridization or by synthesizing a complementary strand using a polymerase or ligase (sequencing by synthesis, sequencing by ligation). In some embodiments, the method comprises a sequencing step, wherein fluorescent signals are generated.

The disclosure provides a method of detecting one or more biomolecular species within a hydrogel comprising in vivo expression of one or more biosensors, each comprising a moiety conferring affinity binding and also a read-out moiety. In some embodiments, the read-out moiety is a transcriptional repressor. In some embodiments, the read-out moiety is a transcriptional activator. In some embodiments, the read-out moiety comprises genome editing activity. In some embodiments, the method further comprises detecting the product of the read-out moiety in situ using nucleic acid sequencing, such as by FISSEQ of one or more RNA species or one or more DNA loci, as by sequencing by hybridization or by synthesizing a complementary strand using a polymerase or ligase (e.g. sequencing by synthesis, sequencing by ligation). In some embodiments, the method comprises detecting fluorescent signals that are generated.

The FISSEQ methods provided herein can be combined with standard staining methods for target detection. The method according to the disclosure comprises the steps of contacting the sample with one or more stain(s), imaging the stain(s), constructing a FISSEQ library in situ within the sample for detection of RNA, DNA, and/or protein, sequencing the FISSEQ library, and integrating computationally the stain data with the FISSEQ data.

The disclosure provides a FISSEQ kit also containing one or more reagents with affinity for a biomolecule and also comprising a detectable label.

Molecular Interaction Detection Via FISSEQ

In some cases, interactions between biomolecules can be detected. There are a number of strategies for detecting and measuring the strength of molecular interactions, but can be generally classified into four themes: quantitation of binding to arrayed analytes, cross-linked purification, complementation assays, and single-molecule imaging.

Quantitation of binding to arrayed analytes involves synthesizing an ordered array of molecules, such as RNA, DNA, or proteins, adding a target molecule, and then measuring the binding profile, e.g., by using a fluorescently labeled target molecule and measuring the level of fluorescence at each spot on the array. See e.g., Mukherjee, Sonali, et al. "Rapid analysis of the DNA-binding specificities of transcription factors with DNA microarrays." *Nature genetics* 36.12 (2004): 1331-1339; Buenrostro, Jason D., et al. "Quantitative analysis of RNA-protein interactions on a massively parallel array reveals biophysical and evolutionary landscapes." *Nature biotechnology* 32.6 (2014): 562-568; Espina, Virginia, et al. "Protein microarray detection strategies: focus on direct detection technologies." *Journal of immunological methods* 290.1 (2004): 121-133. These methods can be limited to assaying one molecule at a time, although it may be possible to design library-on-library methods of assaying binding to arrayed analytes. For example, one could imagine using FISSEQ to detect nucleic acid molecules or DNA-barcoded proteins binding on an array of analytes, or mass spectrometry imaging to detect proteins directly. See e.g., van Hove, Erika R. Amstalden, Donald F. Smith, and Ron MA Heeren. "A concise review of mass spectrometry imaging." *Journal of chromatography* A 1217.25 (2010): 3946-3954. One can imagine other methods of library-on-library screening using arrayed analytes, such as via molecular barcoding (i.e., where the barcode of the target molecule, such as a protein-ribosome-messenger-RNA-complementary-DNA (PRMC) is linked to a barcode indicating the position of binding within the array or the identity of the binding partner). SMI-seq is a related form of quantitation of binding, but where the analytes are not arrayed but instead diluted and detected in place using FISSEQ. See e.g., Gu, Liangcai, et al. "Multiplex single-molecule interaction profiling of DNA-barcoded proteins." *Nature* 515.7528 (2014): 554-557; (also see above discussion on SMI-seq.

The cross-linked purification assay can be immunoprecipitation (IP), wherein a protein antigen is precipitated using an immunoprotein along with its binding partners, which are then detected. There are many variations on this theme, such as Chromatin IP (ChIP) for detecting protein-genome interactions (Jothi, Raja, et al. "Genome-wide identification of in vivo protein-DNA binding sites from ChIP-Seq data." Nucleic acids research 36.16 (2008): 5221-5231), and cross-linking and IP (CLIP) for detecting protein-RNA interactions (Ule, Jernej, et al. "CLIP: a method for identifying protein-RNA interaction sites in living cells." Methods 37.4 (2005): 376-386), both of which can use NGS for unbiased high-throughput detection of the nucleic acids interacting with the target protein. Co-immunoprecipitation and mass spectroscopy can be used to detect proteins bound to a target protein. See e.g., Free, R. Benjamin, Lisa A. Hazelwood, and David R. Sibley. "Identifying Novel Protein-Protein Interactions Using Co-Immunoprecipitation and Mass Spectroscopy." *Current Protocols in Neuroscience* (2009): 5-28. Another strategy may be to target a nucleic acid for purification, using hybridization to "pull-down" certain regions of chromatin, or certain RNA species, and then using mass spectroscopy to detect bound proteins. Déjardin, Jérôme, and Robert E. Kingston. "Purification of proteins associated with specific genomic Loci." *Cell* 136.1 (2009): 175-186; Butter, Falk, et al. "Unbiased RNA-protein interaction screen by quantitative proteomics." *Proceedings of the National Academy of Sciences* 106.26 (2009): 10626-10631. All of the chromatin conformation capture sequencing methods (see e.g., Dekker, Job, et al. "Capturing chromosome conformation." science 295.5558 (2002): 1306-1311) can be a version of cross-linked purification, wherein DNA molecules in close proximity are cross-linked and purified. In these methods, the chemical cross-link can be replaced with a covalent linkage via ligation, allowing the chemical cross-links, which impede amplification and sequencing, to be reversed and creating sequence junctions that can be detected by NGS. Similarly, psoralen analysis of RNA interactions and structures (PARIS) uses the psoralen-derivative 4'-aminomethyltrioxsalen (AMT) for reversible cross-linking, followed by ligation, to detect RNA-RNA interactions by NGS (Lu, Zhipeng, et al. "RNA Duplex Map in Living Cells Reveals Higher-Order Transcriptome Structure." Cell 165.5 (2016): 1267-1279). The reversible psoralen cross-linking technique can likely be extended to analysis of DNA-DNA and RNA-DNA interactions.

Complementation assays use a novel functionality generated by the proximity of molecular labels, which are subsets of a reporter system, to detect molecular interactions. Hybrid complementarity screening assays typically use a transcriptional reporter system comprising one or more transcription factor fragments and the target sequence. These components are attached to endogenous molecules, e.g., by creating fusion proteins. When the target molecules interact, the reporter system can be reconstituted and activates transcription of a selectable marker, such as an antibiotic resistance gene.

Some classic examples are bacterial one-hybrid DNA-protein interaction screening (Meng, Xiangdong, and Scot A. Wolfe. "Identifying DNA sequences recognized by a transcription factor using a bacterial one-hybrid system." *NATURE PROTOCOLS-ELECTRONIC EDITION*-1.1 (2006): 30), yeast two-hybrid protein-protein and protein-DNA screening (Chien, Cheng-Ting, et al. "The two-hybrid system: a method to identify and clone genes for proteins that interact with a protein of interest." *Proceedings of the National Academy of Sciences* 88.21 (1991): 9578-9582; Vidal, Marc, et al. "Reverse two-hybrid and one-hybrid systems to detect dissociation of protein-protein and DNA-protein interactions." *Proceedings of the National Academy of Sciences* 93.19 (1996): 10315-10320), and yeast three-hybrid protein-RNA interaction screening (Hook, Brad, et al. "RNA-protein interactions in the yeast three-hybrid system: Affinity, sensitivity, and enhanced library screening." *Rna* 11.2 (2005): 227-233). Other forms of complementation assays utilize fluorescence to detect molecule interactions in vivo. Fluorescence resonance energy transfer (FRET) enables the transfer of energy between a donor and acceptor fluorophore if they are within 10 nm proximity (see e.g., Jares-Erijman, Elizabeth A., and Thomas M. Jovin. "Imaging molecular interactions in living cells by FRET microscopy." *Current opinion in chemical biology* 10.5 (2006): 409-416), creating a detectable fluorescent signal. Bimolecular fluorescence complementation (BiFC) uses non-fluorescent fragments of fluorescent proteins, which temporarily reassemble and become fluorescent when they are in close proximity. See e.g., Magliery, Thomas J., et al. "Detecting protein-protein interactions with a green fluorescent protein fragment reassembly trap: scope and mechanism." *Journal of the American Chemical Society* 127.1 (2005): 146-157; Kerppola, Tom K. "Design and implementation of bimolecular fluorescence complementation (BiFC) assays for the visualization of protein interactions in living cells." *Nature protocols* 1.3 (2006): 1278-1286. These fluorescent techniques can also be used to visualize single interactions using super-resolution microscopy. See e.g., Liu, Zhen, et al. "Super-resolution imaging and tracking of protein-protein interactions in sub-diffraction cellular space." *Nature communications* 5 (2014).

Finally, the advent of super-resolution microscopy can enable direct visualization of individually labeled components forming a molecular complex. Super-resolution imaging by photoactivated localization microscopy (PALM) can be used in situ to determine the spatial distribution and co-localization of two proteins with 20 nm accuracy. See e.g., Sherman, Eilon, Valarie A. Barr, and Lawrence E. Samelson. "Resolving multi-molecular protein interactions by photoactivated localization microscopy." *Methods* 59.3 (2013): 261-269. Reflected light-sheet microscopy (RLSM) can be in vivo to measure transcription factor binding dynamics to DNA (the DNA target is not directly detected), and co-localization of two DNA binding proteins. Sec e.g., Gebhardt, J. Christof M., et al. "Single-molecule imaging of transcription factor binding to DNA in live mammalian cells." *Nature methods* 10.5 (2013): 421-426. While these methods may be technically challenging. ExM can be used to facilitate super-resolution detection of molecular interactions in situ using much simpler diffraction-limited imaging modalities. See e.g., Chen, Fei, Paul W. Tillberg, and Edward S. Boyden. "Expansion microscopy." *Science* 347.6221 (2015): 543-548.

In order to capture information about molecular interactions into the FISSEQ library, the proximity capture concepts from cross-linked purification and complementation assays can be used. For example, rather than immunoprecipitating or pulling down a protein or nucleic acid target, the target can be bound using a molecular probe in situ. The molecular probe can be a nucleic acid or bear a nucleic acid barcode. In some cases, the Proximity Ligation Assay (PLA) can be used to create a new hybrid sequence with nearby nucleic acids, which can then be detected by FISSEQ. See e.g., Söderberg, Ola, et al. "Direct observation of individual endogenous protein complexes in situ by proximity ligation." *Nature methods* 3.12 (2006): 995-1000. Proximity Ligation Assay (PLA) can also be used to detect proximity of endogenous nucleic acid sequences, for chromatin conformation capture sequencing, RNA duplex detection (PARIS), or detection of neuronal synapses using transgenic cellular barcodes (BOINC). Alternatively, as with complementation assays, the molecular probe may bear a component of an FISSEQ library construction reaction, such as an RT primer or an enzyme, localizing the library construction chemistry to sequences proximal to a target molecule.

Using ExM combined with FISSEQ, massively multiplex detection of molecular interactions by direct visualization can be achieved. Detection of co-localization can be used to infer interaction, as well as to estimate thermodynamic quantities such as binding free energies. See e.g., Helmuth, Jo A., Grégory Paul, and Ivo F. Sbalzarini. "Beyond co-localization: inferring spatial interactions between sub-cellular structures from microscopy images." *BMC bioinformatics* 11.1 (2010): 1; Herce, H. D., C. S. CASAS-DELUCCHI, and M. C. Cardoso. "New image colocalization coefficient for fluorescence microscopy to quantify (bio-) molecular interactions." *Journal of microscopy* 249.3 (2013): 184-194).

One benefit of using direct visualization compared to proximity ligation, can be that the latter is limited to detecting interactions that position the tags within a short distance, typically ~10 nm, which generally limits detection to pairwise or extremely proximal interactions. See e.g., Söderberg, Ola, et al. "Direct observation of individual endogenous protein complexes in situ by proximity ligation." *Nature methods* 3.12 (2006): 995-1000. Direct detection of these complexes can allows us to visualize the organization and spatial relationships between molecular complexes that are large, or involve many components. For example, the RNA splicing machinery comprises hundreds of proteins, as well as RNA molecules. Enumerating the constituent molecules and interactions can provide only abstract network graph representations of the population average states, which can be difficult to interpret or map to physical structures. See e.g., Zhou, Zhaolan, et al. "Comprehensive proteomic analysis of the human spliceosome." *Nature* 419.6903 (2002): 182-185; Dominguez, Daniel, and Christopher B. Burge. "Interactome analysis brings splicing into focus." *Genome biology* 16.1 (2015); Pires, Mathias M., et al. "The network organization of protein interactions in the spliceosome is reproduced by the simple rules of food-web models." *Scientific reports* 5 (2015). Progress towards determining the overall spatial organization of this complex, and the location of specific elements, has been mainly advanced by cryo-EM. Sec e.g., Newman, Andrew J., and Kiyoshi Nagai. "Structural studies of the spliceosome: blind men and an elephant." *Current opinion in structural biology* 20.1 (2010): 82-89. Direct visualization of molecular complexes with nanometer-scale resolution using panomic FISSEQ detection captures the best aspects of both of these approaches.

To summarize the molecular interaction detection, the disclosure provides use of two or more molecular probes for detection of a molecular interaction in situ, wherein each probe also comprises a DNA barcode. In some embodiments, the current disclosure provides methods of in situ sequencing, including sequencing by hybridization or by synthesizing a complementary strand uses a polymerase or ligase (e.g. sequencing by synthesis, sequencing by ligation). In some embodiments, the method comprises detecting fluorescent signals generated in sequencing. In some embodiments, the disclosure provides use of two or more nucleic acid barcodes linked in situ by proximity ligation. In some embodiments, the ligation junction serves as an identifier of the interaction.

In some embodiments, the present disclosure provides a method of preparing an in situ sequencing library. In some embodiments, the method comprises the step of ligating two or more nucleic acid barcodes when they are in close proximity.

In some embodiments, the method comprises preparing an in situ sequencing library, wherein the method comprises using one nucleic acid species to prime a nucleic acid polymerization reaction templated by a distinct nucleic acid species. In some embodiments, one or both of the nucleic acid species is a nucleic acid barcode representing a protein, RNA, DNA, or other biomolecule, and wherein one or both of the nucleic acid species is an endogenous nucleic acid molecule. The disclosure provides a method of inferring a molecular interaction by the spatial proximity of two FISSEQ identifications.

The disclosure provides a kit or a system for forming a molecular interaction FISSEQ library comprising reagents for forming a hydrogel in situ. In some embodiments, the kit comprises reagents for linking DNA, RNA, or other nucleic acid barcodes into the hydrogel in situ.

The disclosure provides a kit or a system for fluorescent in situ sequencing of a molecular interaction FISSEQ library comprising more than one species of oligonucleotide conjugated to a fluorescent moiety. In some embodiments, the kit comprises a DNA ligase. In some embodiments, the kit comprises an imaging buffer and/or an incorporation buffer.

The disclosure provides a kit or a system for fluorescent in situ sequencing of a molecular interaction FISSEQ library comprising more than one species of dNTP analog conjugated to a fluorescent moiety. In some embodiments, the kit comprises a DNA polymerase. In some embodiments, the kit comprises an imaging buffer and/or an incorporation buffer.

The disclosure provides a kit or a system for fluorescent in situ sequencing of a molecular interaction FISSEQ library comprising more than one species of metastable self-assembling DNA hairpins, e.g., hybridization chain reaction monomers, conjugated to a fluorescent moiety.

In some embodiments, the kit comprises more than one species of DNA oligonucleotides comprising sequences complementary to affinity binder barcode sequence. In some embodiments, the kit comprises an imaging buffer. In some embodiments, the kit comprises a hybridization buffer and/ or an HCR amplification buffer.

Cytological and Histological Stains

Staining can be an important technique for enhancing the contrast between aspects of a biological sample, typically by differential binding of some components of the sample. Since the discovery of synthetic aniline dyes, scientists have used chemical reactions and affinities between chemicals and tissue components to enhance the optical properties of tissue for visual or microscopic analysis of tissue architecture and chemical and molecular composition. One of the most well-known stains can be the combination of haematoxylin and eosin (H&E), which stain nucleic acids and cytoplasmic/extracellular tissue components, respectively. Other exemplary stains include toluidine blue, Masson's trichrome stain, Mallory's trichrome stain, Weigert's elastic stain, Heidenhain's AZAN trichrome stain, Silver stain, Wright's stain, Orcein stain, and periodic-acid Schiff stain (PAS). DAPI and other intercalating dyes can also be used to label nucleic acids and nuclei.

To summarize the staining plus FISSEQ, the method according to the disclosure comprises the steps of contacting the sample with one or more stain(s); imaging the stain(s); constructing a FISSEQ library in situ within the sample for detection of RNA, DNA, and/or protein; sequencing the FISSEQ library; and integrating computationally the stain data with the FISSEQ data.

The disclosure provides a FISSEQ kit also containing one or more cytological and/or histological stain reagents.

Super-Resolution Microscopy for Panomic FISSEQ

In some cases, higher resolution of imaging is needed. Within biological systems, most objects are on the order of nanometers in size. For example, the "B" form of the DNA helix is 23.7 angstroms wide and 34 angstroms long per 10 base pairs. See e.g., Watson, James D., and Francis HC Crick. "Molecular structure of nucleic acids." *Nature* 171.4356 (1953): 737-738. The smallest polypeptides are also on the order of several nanometers long. Therefore, "perfect resolution" with respect to biology can be on the order of several nanometers. Any number of strategies can be used to achieve this resolution for fluorescence imaging.

DNA PAINT, a form of stochastic super-resolution microscopy, has demonstrated sub-10-nm resolution. See e.g., Silverberg, Jesse L., et al. "DNA-Paint and Exchange-Paint for Multiplexed 3D Super-Resolution Microscopy." *Biophysical Journal* 108.2 (2015): 477a. Using this and other super-resolution modalities for FISSEQ may require development of single-molecule "sequencing" for detection and localization of single fluorophores. Although this would enable simultaneous sequencing of all molecules, imaging time for each cycle of sequencing may be long. Acquiring DNA PAINT images with sub-10 nm resolution requires hours of imaging per frame using high magnification, which also may limit the field of view per image.

Another approach may be to use signal amplification, as by RCA or Cyclic HCR (CHCR), together with digital partition microscopy. This could achieve sufficient resolution, but at the cost of localization, as the amplicons themselves are nearly two orders of magnitude larger than the target molecules. This method may also require serial sequencing of a number of partitions, which dramatically increases assay time. There may also be steric limitations; for example, it may not be possible to generate many RCA amplicons within the same physical volume.

ExM can be another strategy for achieving perfect resolution because it can use the low magnification and fast pixel acquisition rates of diffraction-limited microscopy to image with arbitrary resolution and excellent localization. (The localization accuracy of ExM may be limited by the density of molecular capture nodes during polymerization and isotropy of the resulting expanding hydrogel, as well as the physical size of the chemistry used to capture the target molecule or detectable label.) All the strategies discussed herein can be used to achieve panomic FISSEQ to ExM. After capturing this information into the gel, expansion with a linear expansion factor of several hundred can be sufficient to achieve single-nanometer resolution. Moreover, we can highly amplify the signal, as by RCA or Cyclic HCR (CHCR), since these amplicons are generally diffraction-limited in size and therefore will be both resolvable and physically separated.

The combination of ExM and FISSEQ combines the multiplexity, sensitivity, and accuracy of NGS and MS with resolution that can be scaled in an arbitrary manner by manipulating the composition of the hydrogel or by serial expansion.

In some cases, the hydrogel (e.g., three-dimensional matrix) can be made with aid of swelling agents that can be activated by an external stimulus. The present hydrogel systems described herein may comprise functional hydrogel matrices and/or solvent compositions that are capable of externally induced volume state transitions. Optionally, the hydrogels may not be an ionic polymer matrix that expands upon dialysis of salt via addition of liquid water.

Optionally, the hydrogel may comprise one or more swelling agents. Swelling agents as described herein may refer to any mechanism that partakes in and/or induces swelling of a three-dimensional matrix. Optionally, the swelling agent may be a functionality built into a polymer backbone. For example, the swelling agent may be mechanism within the three-dimensional matrix that, when activated by a stimulus (e.g., external stimulus) may induce a change in network topology of the matrix. In some instances, an external stimulus (e.g., electromagnetic radiation) may induce a breaking of cross-links between polymer chains in the matrix so as to swell the hydrogel. In such instances, the swelling agent may refer to a subset of cross-links of the polymer matrix. In some instances, an external stimulus (e.g., thermal stimulus) may induce a change in non-covalent linkages (e.g., breaking of such linkages) between polymer backbones so as to swell the hydrogel. In such instances, the swelling agent may refer to non-covalent linkages. In some instances, the swelling agent may be a programmable chelator within the matrix. In some instances, the three-dimensional matrix may undergo a structural rearrangement in response to a stimulus, and/or with aid of a swelling agent.

In some instances, the external stimulus is an electromagnetic stimulus, an electrochemical stimulus, or a thermal stimulus. The swelling agents can comprise chemical groups which are activatable by an external stimulus, such as an electromagnetic stimulus, an electrochemical stimulus, or a thermal stimulus. Electromagnetic stimulus can include light with different wavelengths. In some embodiments, the present disclosure provides a system or a method for detection or identification of one or more biomolecules of a biological sample, comprising a swelling agent, wherein said swelling agent is activatable upon application of a stimulus to increase in volume to yield a three-dimensional matrix comprising said biomolecules, wherein said stimulus is an electromagnetic stimulus, an electrochemical stimulus, or a thermal stimulus, wherein said three-dimensional matrix preserves an absolute or relative spatial relationship of said biomolecules within the biological sample. In some embodiments, the swelling agent further comprises an attachment moiety, wherein the biomolecules of interest can be linked to the swelling agent through the attachment moiety. In some embodiments, the application of an external stimulus to the swelling agent activates said swelling agent to form said three-dimensional polymer matrix, which three-dimensional polymer matrix preserves an absolute or relative spatial relationship of the biomolecules within a biological sample. In various embodiments, the swelling agents form a 3-dimensional hydrogel matrix. In some embodiments, the swelling agent can be a contracting agent, wherein the contracting agent can aid in contracting and/or shrinking of the three-dimensional matrix.

Optionally, the three-dimensional matrix may undergo a structural rearrangement in response to a stimulus, and/or with aid of a contracting agent so as to contract or shrink. The contracting, or shrinking agent may be mechanism within the three-dimensional matrix that, when activated by a stimulus (e.g., external stimulus) may induce a change in network topology of the matrix. Optionally, the contracting agent may be a functionality built into a polymer backbone. In some instances, an external stimulus (e.g., electromagnetic radiation) may induce a forming of cross-links between polymer chains in the hydrogel (e.g., matrix) so as to contract the hydrogel. In such instances, the contracting agent may refer to a subset of cross-links of the polymer matrix. In some instances, an external stimulus (e.g., thermal stimulus) may induce a change in non-covalent linkages (e.g., forming of such linkages) between polymer backbones so as to contract the hydrogel. In such instances, the swelling agent may refer to non-covalent linkages. In some instances, the swelling agent may be a programmable chelator within the matrix.

For example, the swelling/contracting agents may be activated to expand by a light with a certain wavelength, and may be activated to shrink by a light with a different wavelength. In some instances, with the stimulus, the contracting agent previously In some embodiments, the external stimulus is not liquid. Described herein the biological sample can include organs, tissues, cells, exosomes, blood, or a portion thereof. Cell samples may include any subcellular components or cell derivatives.

As one example, the hydrogel described herein may comprise a polyacrylamide-bisacrylamide (PA-BIS) copolymer with N,N'-Bis (acryloyl) cystamine (BAC) crosslinkers. The hydrogel may be polymerized at a certain size, and upon electrochemical induction by reduction of the disulfide, breaking a subset of cross-links within the hydrogel matrix, the hydrogel may expand in size. In such instances, only a subset of cross-links within the hydrogel matrix may be broken, such that after expansion or swelling, there is still a 3D hydrogel matrix present, to which biomolecules or biomolecular labels are attached.

In another example, the hydrogel may be a thermally induced hydrogel. The thermally induced hydrogel may undergo a volume transition in response to thermal stimuli. One example of a thermally induced hydrogel is a NIPAM gel. In such hydrogels, a volume transition may be caused by changes in the non-covalent linkages among the hydrogel backbone, analogous to electrochemically-induced change in disulfide bond-state among a PA-BIS-BAC hydrogel network.)

In another example, the hydrogel may be an ionic polymer hydrogel. An example of such a hydrogel may be an acrylamide-acrylate-bisacrylamide copolymer hydrogel, with a programmable chelator solute component, such as photocaged-EDTA. Activation or change of the conformation of the photo caged chelator element may trigger a change in the effective ionic strength of the solution within the hydrogel, as by absorbing (chelating) or releasing ions, which serve to modulate the wetting strength of the ionic polymer matrix, causing swelling and contraction.

To summarize the super resolution microscopy for panomic FISSEQ, the method of forming an expanding hydrogel in situ according to the disclosure comprises more than one detectable labels each corresponding to a biomolecular species, wherein the hydrogel swells causing expansion by a factor of from 2× to 3×, from 3× to 4×, from 4× to 5×, form 5× to 6×, from 6× to 7×, from 7× to 8×, from 8× to 9×, from 9× to 10×, or greater than 10× in linear dimension, and wherein the hydrogel is stabilized in the expanded state. In some embodiments, the hydrogel swells causing expansion by a factor of from 2× to 10×in linear dimension. In some instances, the hydrogel may swell due to existence of swelling agents. In some instances, the swelling agent may be activated by a stimulus as further described herein so as to yield a three-dimensional matrix (e.g., a gel). Optionally, the hydrogel may be configured to contract. For example, the hydrogel may contract with aid of contracting agents. Optionally, the swelling agents described herein may act as further contracting agents.

The present disclosure provides a method of forming an expanding hydrogel in situ comprising one or more endogenous nucleic acid species.

The present disclosure provides a method of forming an expanding hydrogel in situ comprising one or more nucleic acid barcode species serving as labels detectable by FISSEQ for certain biomolecular species.

The present disclosure provides a method of forming an expanding hydrogel in situ comprising one or more endogenous nucleic acid species and one or more nucleic acid barcode species. In some embodiments, the expanding hydrogel comprises a light activated swelling agent, including chelate counter-ions such as ortho-nitrobenzyl caged EDTA. In some embodiments, the swelling agent can expand when activated by one wavelength, and shrink/contract when activated by a different wavelength. In some embodiments, the swelling agent can shrink/contract to $\frac{1}{5}$~$\frac{1}{4}$, $\frac{1}{4}$~$\frac{1}{3}$, $\frac{1}{3}$~$\frac{1}{2}$ of the original expanded size. In some embodiments, the expanding hydrogel comprises an electrochemically activated swelling agent, including chelate counter-ions such as quinone-ester protected EDTA. In some embodiments, the expanding hydrogel comprises a thermally activated swelling agent, for example chelate counter-ions.

The hydrogel can be expanded or contracted for different detection purpose. For example, in some cases, the hydrogel are programmed to be expanded, making the targets of interest apart from each other so that they can be resolved during imaging step. In some cases, the hydrogel are programmed to be contracted after contacting with additional reagents, making targets of interest closer to each other for interaction detection. In some instances, the hydrogel may be expanded using a stimulus. The stimulus may be any type of stimulus, e.g., an electromagnetic stimulus, electrochemical stimulus, or a thermal stimulus. In some instances, the stimulus may not be a liquid. Optionally, the hydrogel may be contracted using another stimulus. The stimulus used for expansion and the another stimulus used for contraction, or shrinking, may be of a same type (e.g., both light). Optionally, the stimulus used for expansion and the another stimulus used for contraction, may be of different types (e.g., light and chemicals). In some cases, the hydrogel can be expanded upon an external stimulus, such as light at a first wavelength, and a reagent mixture may be flown through after the expansion, and then the hydrogel can be contracted subsequently with an external stimulus, such as light at a second wavelength, wherein the first and the second wavelengths are different.

Panomic FISSEQ Library Construction and Hydrogel Composition

Molecular and Probe Capture

In order to construct a panomic FISSEQ library, the original molecules or a detectable label representing the original molecule (i.e., a nucleic acid barcode) need to be captured into the hydrogel matrix for fluorescent detection via sequencing. The FISSEQ hydrogel functions to preserve the relative or absolute 3D spatial positional information of molecules during the steps of library construction and sequencing. The positional fidelity of the capture and interrogation can be determined by the density of capture nodes in the hydrogel, wherein capture nodes are linkages, either direct or indirect, between the matrix and the original molecule or representing label, as well as by the topological and/or spatial invariance of the hydrogel matrix itself. For example, topological invariance requires that the spatial relations between analytes are preserved (e.g., within/without relations, order relations). Spatial invariance may refer to preservation of either absolute or relative spatial relations, e.g., such that all nodes within the hydrogel matrix maintain a constant absolute or relative relationship with respect to other nodes or fiducial markers. In the case of ExM, the hydrogel may be expanding; although isotropic expansion of the hydrogel preserves the spatial information present by preserving the relative distances between nodes within the hydrogel. Alternatively, the hydrogel may exhibit hybrid properties, such as short-distance spatial invariance or isotropic expansion, but lose spatial relationships over longer-distances (although this may be mitigated by computational analysis or use of fiducial markers).

Information about the identity and localization of proteins can be captured by linking the protein itself into the gel, or by linking the DNA barcode from an antibody or probe, which may be itself attached or bound to the protein, or by an intermediate (e.g. primary, secondary, tertiary, or higher-order information transfer). See e.g., Tillberg, Paul W., et al. "Protein-retention expansion microscopy of cells and tissues labeled using standard fluorescent proteins and antibodies." *Nature Biotechnology* (2016); Chen, Fei, Paul W. Tillberg, and Edward S. Boyden. "Expansion microscopy." *Science* 347.6221 (2015): 543-548). The protein itself may be captured into the hydrogel by virtue of intrinsic properties of the protein target, e.g. covalent polymerization of the thiol present on cysteine residues of proteins, as well as N-terminal amines, the epsilon-amino of lysine, and the imidazole ring of histidine, among other groups, into a growing polyacrylamide chain, or by virtue of chemical modification of the protein to facilitate incorporation or covalent linkage of the protein into the hydrogel matrix during or after formation of the matrix. A probe (e.g. primary, secondary, or higher-order) may be linked into the FISSEQ hydrogel by virtue of bearing a chemical moiety that specifically or non-specifically interacts with the hydrogel matrix during or after formation (e.g., polymerization) of the hydrogel matrix. In the case of immunoproteins and other types of synthetically expressed peptide probes, expression of these probes in the presence and incorporation of non-natural amino acids into the peptide, as in an in vitro or in vivo expression system, for the purpose of directly incorporating a chemical moiety that can be linked into the hydrogel matrix, or to incorporate a chemical moiety that can be further modified in vivo or in vitro to form a chemical moiety capable of being covalently linked to the hydrogel matrix. In the case of immunoproteins and other types of synthetically expressed peptide probes, expression of these probes may be used to chemically link the probe to a nucleic acid sequence, which serves as the nucleic acid barcode or label, e.g. by mRNA display or ribosome display to link a RNA molecule to the protein, or by further localizing a cognate DNA or cDNA molecule to the probe, e.g. by reverse transcription.

Information about the sequence and localization of nucleic acids can be captured by linking the nucleic acid itself, as by using our novel LabelX reagent, or by linking some kind of nucleic acid probe, such as an OligoPaint, padlock probe, or MIP. The LabelX reagent is comprised of a nitrogen mustard reactive group and modular reactive amine linker of Label-IT Amine (MirusBio), and further enables development of other attachment chemistries beside free-radical polymerization of acryloyl into polyacrylamide. For example, an NHS-ester-azide compound could be conjugated to Label-IT Amine to create a new linker capable of tethering nucleic acids into a PEG-click hydrogel. On the other hand, we can use the hydrogel attachment moiety, such as the AcX 6-((Acryloyl)amino) hexanoic acid (Life Technologies) component of LabelX, to create other attachment chemistries to diverse target molecules. Nitrogen mustard is effective at reacting with nucleic acids, but the reactive alkyne also reacts non-specifically with other heteroatoms. Any number of new linkers can be generated with other reactive properties, or enhanced specificity for covalent capture of a particular class of target molecules into the FISSEQ hydrogel. Other types of chemistries for specifically linking nucleic acids into the hydrogel matrix include reagents capable of intercalating into double-stranded nucleic acids and bearing a chemical moiety capable of linking into the hydrogel matrix. These reagents may also bear other functional moieties, such as for establishing a covalent linkage with the nucleic acid after being specifically directed to the nucleic acid via intercalation. Another chemistry for specifically linking nucleic acids into the hydrogel matrix includes the nucleic acid mercuration reaction, by which mercury atoms react with nucleic acids to form a complex further reactive to sulfhydryl groups. Such a chemistry may involve the steps of contacting the nucleic acid with a solution of mercury salt, optionally removing complexed but un-reacted mercury, such as with hydrogen cyanide, and finally reacting with a compound containing both sulfhydryl group and a hydrogel linkage group, such as a free-radical polymerizable group including acryloyl, click group, or other group reactive for the purpose of conjugation to the hydrogel matrix.

Hydrogel Composition, Molecular Incorporation and Exclusion

To form the FISSEQ hydrogel, certain properties can be desired, such as: compatibility with enzymes, rapid diffusion, thermal, physical, photo-, and chemical stability, optical clarity, facile chemistry for establishing covalent linkages with nucleic acids, a method of attachment to a solid support substrate, bioorthogonality, and a uniform nanoscale network architecture.

The composition and formation chemistry of the FISSEQ hydrogel can partially determine the types of molecules and chemical moieties incorporated into the FISSEQ hydrogel. For example, free-radical polymerization of a polyacrylamide-bisacrylamide hydrogel can chemically incorporate certain groups capable of participating in free radical polymerization into the hydrogel. Other polymers formed from bi- or multi-functional monomers, or copolymers of acrylamide, bisacrylamide, and other bi- or poly-functional monomers, such as click-monomers, can provide a functional hydrogel after polymerization by virtue of the additional functionality. For example, click-functional propargyl acrylamide (PAm) monomers comprise additional conjugation functionality via the clickable acetylene groups in the resulting polymer. Other types of hydrogels, such as those formed by PEG-click chemistry, in which n-armed PEG polymers, which are end-functionalized with alkynes or azides, can be assembled into a hydrogel matrix via "click" chemistry.

PEG-click gels are hydrogels formed by the covalent linking of multi-armed PEG molecules using "click chemistry". Azide-alkyne cycloaddition, and Copper-Catalyzed Azide-Alkyne Cycloaddition (CuAAC) in particular, are exemplary click chemistry. CuAAC works in aqueous solvent over a wide range of pH and temperatures, and is largely bioorthogonal, meaning the click-functionalized PEG monomers may not react with proteins or nucleic acids. Therefore, the resulting hydrogel can exhibit uniform and even ideal nanoscale network architecture under certain conditions. PEG may be compatible with enzymatic reactions—in fact PEG is a common additive to enhance the reaction kinetics. PEG-click hydrogels can be optically clear. Both the triazole linkage resulting from CuAAC and the PEG spacer are chemically stable, and would likely withstand the thermal, physical, chemical, and phototoxic stresses of sequencing. Nucleic acids can be modified to incorporate into PEG-click gels, enabling tethering of RNA and DNA into the hydrogel; proteins and other types of molecules can also be modified to incorporate into PEG-click gels. Finally, the PEG-click hydrogel can be further functionalized with other linkage groups, ideally along the backbone in a "bottle-brush" topology, providing chemical handles for cross-linking molecules synthesized after formation of the hydrogel, such as the RCA amplicon. Expanding PEG-click hydrogels can be synthesized, wherein the PEG backbone may be functionalized with charged or hydrophilic groups. In some embodiments, the hydrogel can be linked with an attachment moiety or reactive group with target or probe, wherein the attachment group or reactive group are functioned to capture targets of interest or probes. In some embodiments, the hydrogel can be PEG-click hydrogels, wherein the PEG-click hydrogel are formed in situ with or without a biological sample. In some embodiments, a liquid mixture may be flowed through the formed hydrogel such as PEG-click hydrogel, wherein the attachment moiety or reactive group can capture additional molecules in the liquid mixture that is flowed through. In some cases, the method of detecting biomolecules using the polymerized three-dimensional matrix can comprise providing the polymerized three-dimensional matrix, flowing in probes which can bind to the targets to the polymerized three-dimensional matrix, and capturing the probes in the polymerized three-dimensional matrix. In some cases, flowing in the probes comprises flowing in the probes which are coupled to biomolecules to be detected by the probes. In some cases, probes can be captured via attachment moieties.

An appropriate chemical conjugation group can be incorporated into the backbone of the polymer hydrogel network to be used for capturing targets. Exemplary conjugation groups can include primary amine, sulfhydryl, and "Click" chemical groups (e.g. azide, alkyne).

Functional groups can be incorporated at appropriate concentration in order to achieve a functional capture node density in 3D space required for spatial precision. In some embodiments, the average capture node density can be greater than one node per cubic micron, between 1-1000 per cubic nanometer, from 500 to 600 per cubic nanometer, from 600 to 700 per cubic nanometer, from 700 to 800 per cubic nanometer, from 800 to 900 per cubic nanometer, from 900 to 1000 per cubic nanometer, from 1000 to 1200 per cubic nanometer, from 1200 to 1500 per cubic nanometer, from 1500 to 1800 per cubic nanometer, or from 1800 to 2000 per cubic nanometer. In some embodiments, the capture node density can be at least 1000 per cubic nanometer, at least 2000 per cubic nanometer, at least 3000 per cubic nanometer, at least 4000 per cubic nanometer, or at least 5000 per cubic nanometer.

To increase the efficiency and spatial homogeneity of FISSEQ, only the sequencing templates may be specifically cross-linked into the hydrogel, while all other types of biomolecules that may create inhomogeneity in the hydrogel matrix may be removed. For example, cross-linked biomolecules may reduce the effective pore size of the matrix, resulting in inhomogeneous diffusion rates of reagents into the gel, or even create local regions inaccessible to large macromolecules. Cross-linked biomolecules can also interact non-specifically with the oligonucleotides, enzymes, and other reagents introduced during FISSEQ. For example, non-specific binding of capture oligonucleotides to proteins can increase background signal or generate false-positives.

Numerous methods exist for hydrolyzing or washing biomolecules out of biological samples. The methods that do not perturb the FISSEQ hydrogel can be used. Those methods are expected to be orthogonal to nucleic acids (specifically the nucleic acids of interest that are incorporated into the in situ sequencing library and the nucleic acids comprising the sequencing templates). Common permeabilization reagents, mainly comprising organic solvents such as methanol and acetone, and detergents such as Saponin, Triton X-100 and Tween-20, can remove lipids and also some proteins. Proteins can be hydrolyzed enzymatically or chemically. Enzymatic hydrolysis of proteins can be accomplished using a wide array of proteinases, including pepsin, trypsin, erepsin, and proteinase K. Denaturants, such as guanidine HCl and SDS, and reducing agents, such as DTT and beta-mercaptoethanol, can aid by breaking down tight protein structures resistant to enzymatic digestion. Acid hydrolysis of proteins, while effective, may cause degradation of RNA and depurination of DNA, and therefore may not be suitable for FISSEQ. Other chemical methods of peptide bond hydrolysis, however, such as by Pd (II) complexes at neutral pH, may be possible in situ.

Most small molecules and ions can be easily washed from the hydrogel. However, larger carbohydrates like glycosaminoglycans and the proteoglycans, especially present in the ECM, may present a challenge. These compact, crystal-like structures can be difficult to break down, and many are charged, such as heparin, chondroitin, and keratin sulfates, and hyuralonic acid. Many enzymes can have the ability to degrade specific ECM components, including hyuralonases, collagenases, while other enzymes, such as MMPs, exhibit broad-spectrum ECM hydrolysis activity.

In addition to utilizing alternative FISSEQ hydrogel formation chemistries, each with its own characteristics for incorporation of biomolecules and for specific linkage of biomolecules or identifying labels, one can also modulate the reactivity of biomolecules to the hydrogel formation chemistry for the purpose of establishing specific or non-specific linkage as well as for avoiding the formation of certain linkages. The former is discussed above. As an example of the latter, thiol groups on proteins may incorporate into free-radical polymerizing polyacrylamide hydrogels; therefore, passivation of thiols present on biomolecules, as by reaction with maleimide or iodoacetamide, prior to hydrogel formation can specifically prevent these groups from interacting with the hydrogel.

To summarize the panomic FISSEQ hydrogel method, the disclosure provides a method of chemically modifying RNA, DNA, protein, or other biomolecules with attachment moieties for capture into a hydrogel formed in situ.

The disclosure provides a hydrogel material capable of forming covalent linkages with certain biomolecules or attachment moieties. In some embodiments, the method includes treatments to passivate biomolecules from incorporation into the hydrogel, such as acylation of free amino groups, amination of carboxylic acid groups, or alkylation of thiol groups. In other embodiments, the method includes treatments to remove certain types of biomolecules from the hydrogel comprising physically washing away the unwanted biomolecules, treating with SDS/detergents, inducing proteolysis, inducing lipolysis, using enzymatic or chemical degradation of biological structures such as extra-cellular matrix, and/or inducing solubilization and subsequent washing away with organic solvents.

In certain embodiments, the method includes treatments to reduce the auto-fluorescence of molecules covalently linked into the hydrogel for the purpose of enhancing detection via in situ sequencing, such as reduction of carbonyls with sodium borohydride.

Panomic Sequencing In Situ

Sequencing is the process of acquiring a set of ordered signals that function as a rich digital label with effectively unlimited unique identities. Chemistries for determining the sequence of bases within a nucleic acid molecule, or for generating an ordered set of fluorescent signals using a nucleic acid, include but are not limited to sequencing by hybridization (SBH), sequencing by ligation (SBL), and sequencing by synthesis (SBS).

Sequencing for detection of molecular identity may involve detection of endogenous sequence or native nucleic acid sequence, e.g. RNA and DNA molecules present inside a biological specimen at the time of analysis. Those nucleic acid molecules can include the ones that have been modified by any library construction steps, e.g. adapter ligation, circularization, second and additional strand synthesis, amplification (e.g. PCR and RCA). Alternatively, sequencing may be for the detection of nucleic acid labels introduced via probes, such as those linked to immunoproteins, sensors, affinity binding reagents, nucleic acid capture probes (e.g. OligoPaint, MIP, padlock probe), etc. Finally, sequencing may be for detection of both nucleic acid sequences and synthetic barcodes, in serial or in parallel.

Figure 2:
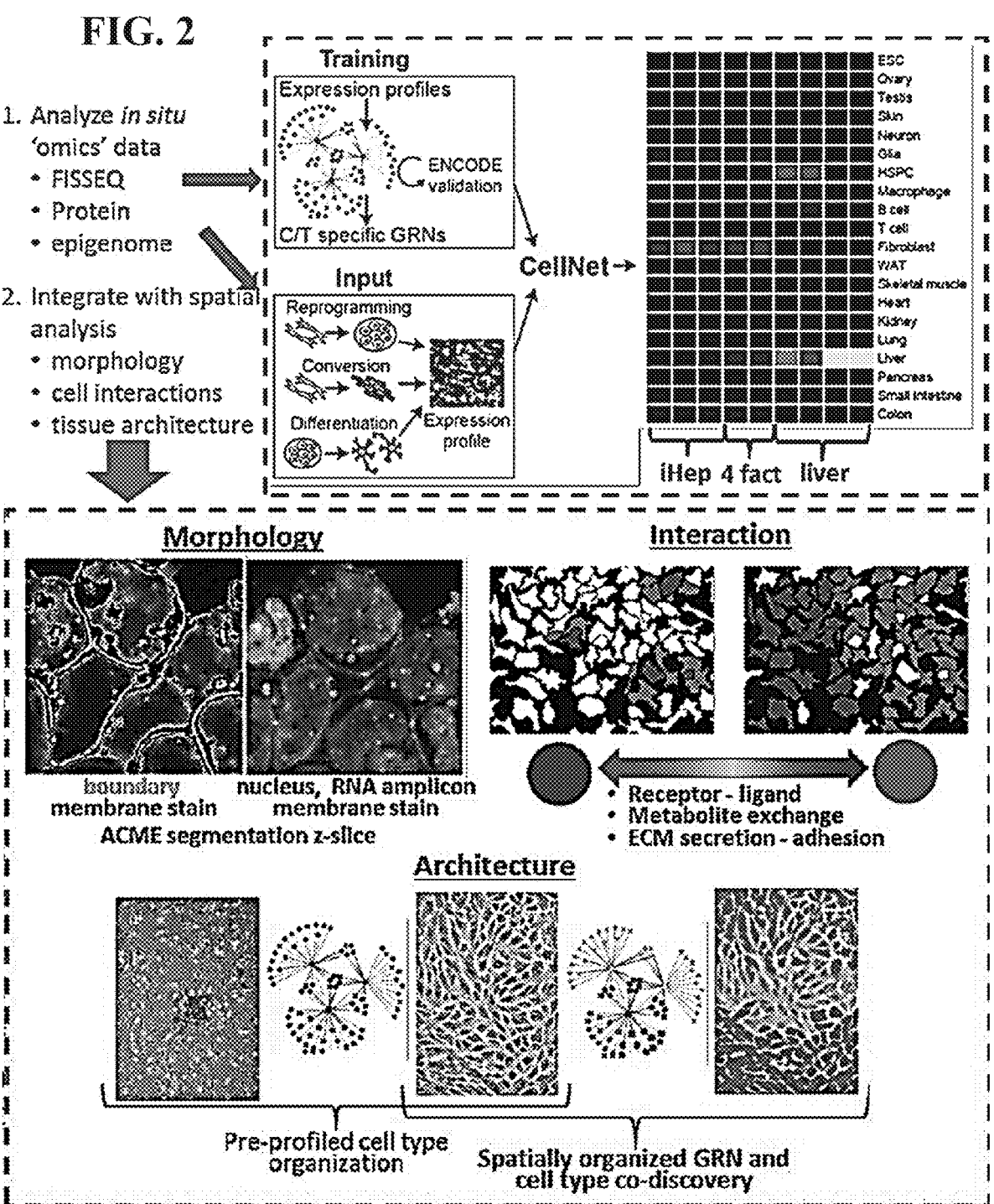
FIG. 2 depicts goals for co-analysis of spatial information from in situ single cell "omics" data on tissues, in accordance with embodiments.

In the case of panomic FISSEQ, sequencing for detection of molecular identity, nucleic acid sequence, or of a nucleic acid label, may be performed for all target molecules simultaneously, i.e. in parallel, or for subsets of molecules in series (FIG. 2). In particular, sequencing for detection of molecular identity may be performed on subsets of molecules within or between "omes", e.g. for transcriptome, genome, proteome, virome, metabolome, lipome, lineageome, etc. Partitioning of the sequencing reactions among the molecular labels and sequences may be achieved by a wide array of techniques, including use of sequencing-reaction-orthogonal conditions, selective priming, and partial labeling. Orthogonal sequencing-reactions refer to sequencing reactions that are carried out under mutually exclusive conditions, such that during any one particular reaction, only a subset of the potential templates can be detected. Selective priming can be relevant to SBS and SBL chemistries, in which the sequencing reactions are "primed" using a short double-stranded nucleic acid from which synthesis of the new complementary nucleic acid is initiated. Priming events are sequence-dependent, i.e. among all molecules being detected, subsets may utilize distinct priming sequences, such that only a subset of sequencing reactions are primed by the introduction of any one sequencing primer. Partial labeling refers to the selective introduction and localization of the fluorescent moieties to a subset of molecules or labels being detected, which is especially relevant to SBH, SBL, and CHCR chemistries. E.g. during interrogation of DNA-conjugated antibodies for detection of proteins using SBH, only a subset of fluorescent probes complementary to the antibody labels may be introduced at any one time.

To summarize the panomic FISSEQ sequencing method, the disclosure provides a 3D hydrogel containing detectable labels corresponding to more than one type of biological polymer, wherein the detectable labels are nucleic acid sequences.

The disclosure provides a method of identifying biomolecules and measuring the absolute or relative spatial relationship between two or more biomolecules within a 3D hydrogel.

The disclosure provides a method of generating a set of ordered fluorescent signals in situ for detection, as by sequencing by sequencing by hybridization or by synthesizing a complementary strand using a polymerase or ligase (sequencing by synthesis, sequencing by ligation).

The disclosure provides a method of serial detection of subsets of molecular species or detectable labels within a FISSEQ library, comprising RNA, DNA, proteins, and/or other types of biomolecules, wherein two or more species of molecules are detected in each step comprising the serial detection process.

The disclosure provides a method of simultaneous detection of molecular species or detectable labels within a FISSEQ library, comprising RNA, DNA, proteins, and/or other types of biomolecules.

The disclosure provides a kit or a system for fluorescent in situ sequencing of a FISSEQ library comprising more than one species of oligonucleotide conjugated to a fluorescent moiety. In some embodiments, the kit comprises a DNA ligase. In some embodiments, the kit further comprises an imaging buffer and/or an incorporation buffer.

The disclosure provides a kit or a system for fluorescent in situ sequencing of a FISSEQ library comprising more than one species of dNTP analog conjugated to a fluorescent moiety. In some embodiments, the kit comprises a DNA polymerase. In some embodiments, the kit comprises an imaging buffer and/or an incorporation buffer.

The disclosure provides a kit or a system for fluorescent in situ sequencing of a FISSEQ library comprising more than one species of metastable self-assembling DNA hairpins, e.g., hybridization chain reaction monomers, conjugated to a fluorescent moiety. In some embodiments, the kit comprises more than one species of DNA oligonucleotides comprising sequences complementary to affinity binder barcode sequence. In some embodiments, the kit comprises an imaging buffer. In some embodiments, the kit comprises a hybridization buffer. In some embodiments, the kit further comprises an HCR amplification buffer.

Computational Identification

Panomic FISSEQ can generate a type of data characterized by a set of images corresponding to the same physical space within and constituting the sample.

For some of this image data, such as that generated by single-identity SBH and stains, a single image can contain all the information necessary for identification and localization of the target molecule, in which case the information about the "image cycle" and corresponding chemical interrogation is digitally linked to the image data during acquisition, and is sufficient for identification. This information may be linked in image metadata, or otherwise associated with the image data, as by timestamps, unique image identifiers, image file paths, database annotations, etc.

For other aspects of the image data, objects can be identified and linked to a set of time-ordered fluorescent signals, e.g. a sequencing read. To process this type of raw image data into molecular identifications and localizations, it may be necessary to process the raw image data into "reads", which are high-dimensional vectors used for identification, typically comprised of an ordered set of identifiers such as nucleobase identities, integers, or other symbols (e.g. "ACTCTA", "0102010120", and so on). The sequencing read may also have accompanying information, including a reference to a spatial coordinate and other spatial or image-based properties, quality data, etc. In certain cases, construction of the sequencing read constitutes the totality of molecular identification, such as for sequencing genomic DNA. In other cases, the ordered signals are mapped to a reference dictionary, which is generically referred to in the bioinformatics community as "alignment".

For panomic sequencing, all reads may be aligned simultaneously to a unified look-up dictionary, known as a reference, such as a database of known RNA or DNA sequences, or a dictionary of synthetic barcodes, or a hybrid reference containing multiple sources and types of identifiers. Alternatively, part of the sequencing read used to direct the look-up dictionary look-up, e.g. using a part of the sequencing read as an address to determine which type of molecule is being identified, for the purpose of selecting an appropriate reference database. Alternatively, reads may be analyzed in serial against a number of references. Assignment of identities to reads may be probabilistic, in the case that a read matches more than one possible identifiers.

In the case of barcode sequencing, barcodes may be constructed for the purpose of enhancing robustness of detection, e.g. by incorporating features of error detecting and/or error correcting codes into the barcode sequence. For example, synthetic barcodes may be separated by a certain Hamming distance, allowing a number of sequencing errors to accrue without causing mis-identification.

To summarize the computational analysis, the disclosure provides a method of annotating image data, as in image metadata, or otherwise by annotations associated with the image data, as by timestamps, unique image identifiers, image file paths, database annotations, etc., such that the image data is linked to the nature of the detectable label(s) being detected.

The disclosure provides a method of analyzing multi-omic or pan-omic FISSEQ data comprising the steps of aligning sequencing reads to one or more databases of molecular identifiers or molecular barcode sequences.

The disclosure provides a method of computationally designing molecular identifiers or molecular barcode sequences by incorporating error-detection or error-correction informatics. Terms and symbols of nucleic acid chemistry, biochemistry, genetics, and molecular biology used herein follow those of standard treatises and texts in the field, e.g., Komberg and Baker, DNA Replication, Second Edition (W. H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like.

Computer Control Systems

Figure 3:
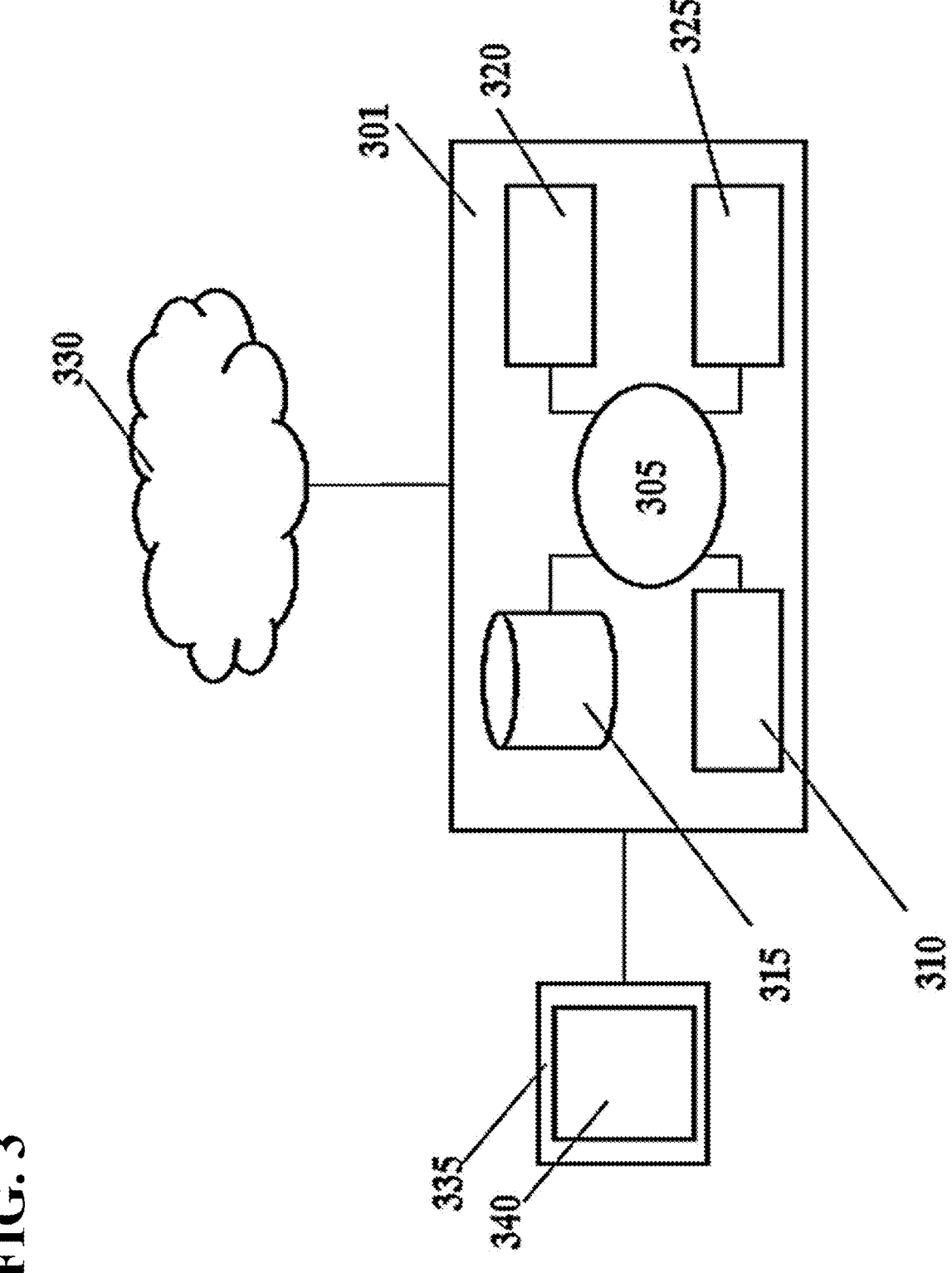
FIG. 3 shows a computer control system that is programmed or otherwise configured to implement methods provided herein.

The present disclosure provides computer control systems that are programmed to implement methods of the disclosure. FIG. 3 shows a computer system 301 that is programmed or otherwise configured to aid in detection or identification of biomolecules, substantially as described throughout. The computer system 301 can regulate various aspects of components and/or devices of the present disclosure utilized in detection of biomolecules, such as, for example, light sources, detectors (e.g., light detectors), devices or components utilized for releasing agents, devices or components utilized in providing conditions for reactions (e.g., hybridization, sequencing, enzymatic reactions), etc. The computer system 301 can be an electronic device of a user or a computer system that is remotely located with respect to the electronic device. The electronic device can be a mobile electronic device.

The computer system 301 includes a central processing unit (CPU, also "processor" and "computer processor" herein) 305, which can be a single core or multi core processor, or a plurality of processors for parallel processing. The computer system 301 also includes memory or memory location 310 (e.g., random-access memory, read-only memory, flash memory), electronic storage unit 315 (e.g., hard disk), communication interface 320 (e.g., network adapter) for communicating with one or more other systems, and peripheral devices 325, such as cache, other memory, data storage and/or electronic display adapters. The memory 310, storage unit 315, interface 320 and peripheral devices 325 are in communication with the CPU 305 through a communication bus (solid lines), such as a motherboard. The storage unit 315 can be a data storage unit (or data repository) for storing data. The computer system 301 can be operatively coupled to a computer network ("network") 330 with the aid of the communication interface 320. The network 330 can be the Internet, an internet and/or extranet, or an intranet and/or extranet that is in communication with the Internet. The network 330 in some cases is a telecommunication and/or data network. The network 330 can include one or more computer servers, which can enable distributed computing, such as cloud computing. The network 330, in some cases with the aid of the computer system 301, can implement a peer-to-peer network, which may enable devices coupled to the computer system 301 to behave as a client or a server.

The CPU 305 can execute a sequence of machine-readable instructions, which can be embodied in a program or software. The instructions may be stored in a memory location, such as the memory 310. The instructions can be directed to the CPU 305, which can subsequently program or otherwise configure the CPU 305 to implement methods of the present disclosure. Examples of operations performed by the CPU 305 can include fetch, decode, execute, and writeback.

The CPU 305 can be part of a circuit, such as an integrated circuit. One or more other components of the system 301 can be included in the circuit. In some cases, the circuit is an application specific integrated circuit (ASIC).

The storage unit 315 can store files, such as drivers, libraries and saved programs. The storage unit 315 can store user data, e.g., user preferences and user programs. The computer system 301 in some cases can include one or more additional data storage units that are external to the computer system 301, such as located on a remote server that is in communication with the computer system 301 through an intranet or the Internet.

The computer system 301 can communicate with one or more remote computer systems through the network 330. For instance, the computer system 301 can communicate with a remote computer system of a user (e.g., a user detecting biomolecules of the present disclosure). Examples of remote computer systems include personal computers (e.g., portable PC), slate or tablet PC's (e.g., Apple® iPad, Samsung Galaxy Tab), telephones, Smart phones (e.g., Apple® iPhone, Android-enabled device, Blackberry®), or personal digital assistants. The user can access the computer system 301 via the network 330.

Methods as described herein can be implemented by way of machine (e.g., computer processor) executable code stored on an electronic storage location of the computer system 301, such as, for example, on the memory 310 or electronic storage unit 315. The machine executable or machine readable code can be provided in the form of software. During use, the code can be executed by the processor 305. In some cases, the code can be retrieved from the storage unit 315 and stored on the memory 310 for ready access by the processor 305. In some situations, the electronic storage unit 315 can be precluded, and machine-executable instructions are stored on memory 310.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 301, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 301 can include or be in communication with an electronic display 335 that comprises a user interface (UI) 340 for providing, for example, at least portions of a container or three-dimensional matrix of the present disclosure for detecting biomolecules. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 305. The algorithm can, for example, be executed so as to detect a plurality of biomolecules utilizing methods and systems disclosed in the present disclosure. The plurality of biomolecules may be of different types of described herein. Optionally, the algorithms may be executed so as to control or effect operation of a component (e.g., light source, detector, etc) of the systems described herein to effect detection of a biomolecule.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising." or "includes" and/or "including." when used in this specification, specify the presence of stated features, regions, integers, steps, operations, elements and/or components, but do not preclude the presence or addition of one or more other features, regions, integers, steps, operations, elements, components and/or groups thereof.

Furthermore, relative terms, such as "lower" or "bottom" and "upper" or "top" may be used herein to describe one element's relationship to other elements as illustrated in the figures. It will be understood that relative terms are intended to encompass different orientations of the elements in addition to the orientation depicted in the figures. For example, if the element in one of the figures is turned over, elements described as being on the "lower" side of other elements would then be oriented on the "upper" side of the other elements. The exemplary term "lower" can, therefore, encompass both an orientation of "lower" and "upper," depending upon the particular orientation of the figure. Similarly, if the element in one of the figures were turned over, elements described as "below" or "beneath" other elements would then be oriented "above" the other elements. The exemplary terms "below" or "beneath" can, therefore, encompass both an orientation of above and below.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Numerous different combinations of embodiments described herein are possible, and such combinations are considered part of the present disclosure. In addition, all features discussed in connection with any one embodiment herein can be readily adapted for use in other embodiments herein. It is intended that the following claims define the scope of the invention and that methods and structures within the scope of these claims and their equivalents be covered thereby.

Examples

Example 1—Exemplary Direct Single-Protein
Sequencing

FIGS. 1A-1C depicts a schematic of direct single-protein sequencing, in accordance with embodiments. FIG. 1A shows that the ordered sequence of amino acid residues may be determined by cycles of N-recognin binding, single-molecule fluorescence detection, such as using cyclic hybridization chain reaction (CHCR), and enzymatic cleavage of the N-terminal residue. FIG. 1B shows that finger-printing using Clps and UBR1, which bind to L/F/Y and R/K/H, respectively, maps the peptide sequence to a low-dimensional fingerprint. FIG. 1C shows an exemplary experimental data that using proteins from RefSeq, this fingerprinting method achieves parity in identification with a full sequencing method after determination of only ~25 residues. Identification likely appears asymptotic at ~60% due to multiple entries, such as protein isoforms, present in the RefSeq database.

Example 2—Co-Analysis of Spatial Information
from In Situ Single Cell "Omics" Data On Tissues FIG. 2 depicts goals for co-analysis of spatial information from in situ single cell "omics" data on tissues. Top: Goals (left) and CellNet functionality (black dashed box, right). CellNet develops gene regulatory network (GRN) profiles for many cell types (nCTs) by systematic analysis of expression data. Expression profiles from engineered tissues (cCTs) are then matched against these profiles to identify correspondences and differences (dashed black box, left). An example of CellNet analysis from of fibroblasts reprogrammed to hepatocyte-like cells using the method of is shown (dashed black box, right). Although these "iHep" lines satisfy marker and functional tests (including animal complementation) for hepatocytes, CellNet shows that they continue to strongly express a fibroblast vs. liver identity. Expression of additional transcription factors (4 total) improves liver matching but does not eliminate the fibroblast identity ("4 fact"). CellNet analyses of fetal and adult liver are also shown; fetal liver exhibits hematopoietic stem cell (HSPC) as well as hepatic identity consistent with its role in fetal hematopoiesis. CellNet indicates that iHep lines also express intestinal identity to a small degree (Colon). Use of CellNet analyses for factors improving colon identity resulted in cells that could functionally engraft colon, suggesting that iHeps are actually bipotent endodermal progenitors. A first step is to adjust CellNet processing to accept in situ "omics" data starting with FISSEQ RNA expression data (Top left, item 1, arrows), then integrate spatial and GRN analysis (Top left, item 2, arrow), anticipated examples of which are depicted (Bottom, dashed box). Cell morphology can be analyzed in the single cells of the tissue and correlated with CT/GRN profile. A preliminary test of image segmentation of cells prepared for FISSEQ using the ACME method is shown (left, segmentation; right, stain overlay). Interactions can be detected by finding cells matched to different CTs in spatial proximity or other spatial structures whose CT GRNs produce products that interact or regulate each other. Interactions and morphology may be more directly observable with single cell in situ protein profiles. These co-analyses of spatial and GRN information are not deeply integrated because they rely on pre-profiled nCTs that are compared to sample "omics" data using current CellNet logic (black box, top). This logic identifies GRN networks associated with specific nCTs that can then be analyzed spatially (Architecture, left, circled GRN represents specific CT). Deeply integrated spatial/GRN analyses may discover cell type or subtype GRNs not previously profiled, by unsupervised clustering of cells in a sample by their "omics"-detected GRN profiles and detecting spatial organization of the clusters (Architecture, right, circled GRN corresponds to spatially organized cell clusters in sample).

What is claimed is:

1. A system for processing multiple biomolecules within a biological sample, comprising: a three-dimensional (3D) polymer matrix comprising
   (i) a swelling agent; and
   (ii) said multiple biomolecules within said biological sample, wherein said multiple biomolecules are covalently attached to said 3D polymer matrix,
   wherein said 3D polymer matrix preserves a relative 3D spatial relationship of said multiple biomolecules within said biological sample; and a source configured to apply a stimulus to said swelling agent, wherein application of said stimulus yields an expanded 3D polymer matrix comprising said multiple biomolecules, wherein said stimulus is an electromagnetic radiation stimulus, an electrochemical stimulus, or a thermal stimulus.

2. The system of claim 1, wherein: (i) said 3D polymer matrix comprises attachment moieties comprising an amine, a thiol, an azide, an alkyne, or a click-reactive group, and (ii) said multiple biomolecules are coupled to said 3D polymer matrix via said attachment moieties.

3. The system of claim 1, wherein said stimulus is light.

4. The system of claim 1, wherein said multiple biomolecules comprise a nucleic acid molecule.

5. The system of claim 1, wherein said 3D polymer matrix is configured to swell by a factor of between 1.1 and 10 upon application of said stimulus to said swelling agent.

6. The system of claim 1, wherein said swelling agent or said 3D polymer matrix comprises non-covalent linkages, and said swelling agent or said 3D polymer matrix is configured such that said non-covalent linkages change upon application of said stimulus to said swelling agent.

7. The system of claim 1, wherein said 3D polymer matrix comprises cross-links, and said 3D polymer matrix is configured such that said cross-links break upon application of said stimulus to said swelling agent.

8. The system of claim 1, wherein said 3D polymer matrix is configured such that a disulfide bond state of said 3D polymer matrix changes upon application of said stimulus to said swelling agent.

9. The system of claim 1, wherein said swelling agent comprises chelation functionality.

10. The system of claim 1, wherein said swelling agent comprises ethylenediaminetetraacetic acid (EDTA).

11. The system of claim 1, further comprising one or more computer processors operatively coupled to said source, wherein said one or more computer processors are individually or collectively programmed to direct said source to apply said stimulus to said swelling agent, thereby activating said swelling agent to yield said expanded 3D polymer matrix.

12. The system of claim 11, wherein said source is a light source.

13. The system of claim 1, comprising a probe coupled to a biomolecule of said multiple biomolecules.

14. The system of claim 13, wherein said probe comprises a nucleic acid sequence.

15. The system of claim 14, wherein said expanded 3D polymer matrix is configured to couple to said probe.

16. The system of claim 1, wherein said biological sample comprises a cell comprising said multiple biomolecules.

17. The system of claim 1, wherein said biological sample is a tissue.

18. The system of claim 1, wherein said multiple biomolecules comprise a protein molecule or a small molecule.

19. The system of claim 1, wherein said 3D polymer matrix comprises a hydrogel.

20. A system for processing multiple biomolecules within a biological sample, comprising: a hydrogel matrix comprising (i) a swelling agent; and (ii) said multiple biomolecules within said biological sample, wherein said multiple biomolecules are covalently attached to said hydrogel matrix, wherein said hydrogel matrix preserves a relative 3D spatial relationship of said multiple biomolecules within said biological sample; a source configured to apply a stimulus to said swelling agent, wherein application of said stimulus yields an expanded hydrogel matrix comprising said multiple biomolecules, wherein said stimulus is an electromagnetic radiation stimulus, an electrochemical stimulus, or a thermal stimulus; and a probe coupled to a biomolecule of said multiple biomolecules.

* * * * *